United States Patent
Chanduszko et al.

(10) Patent No.: US 8,430,903 B2
(45) Date of Patent: Apr. 30, 2013

(54) EMBOLUS BLOOD CLOT FILTER AND DELIVERY SYSTEM

(75) Inventors: Andrzej J. Chanduszko, Chandler, AZ (US); David Micky Graves, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/300,469

(22) Filed: Nov. 18, 2011

(65) Prior Publication Data

US 2012/0065663 A1    Mar. 15, 2012

Related U.S. Application Data

(63) Continuation of application No. 11/997,832, filed as application No. PCT/US2006/017890 on May 9, 2006, now Pat. No. 8,062, 327.

(60) Provisional application No. 60/706,596, filed on Aug. 9, 2005.

(51) Int. Cl.
  *A61F 2/01*        (2006.01)
(52) U.S. Cl.
  USPC .......................................................... 606/200
(58) Field of Classification Search .................. 600/200,
  600/108, 191, 198; 128/831, 841, 843; 606/213,
  606/215, 200, 108, 191, 198, 159; 604/104–107,
  604/164.01, 164.1, 164.11, 165.01, 165.02,
  604/191
See application file for complete search history.

(56) References Cited

U.S. PATENT DOCUMENTS

| | | | |
|---|---|---|---|
| 893,055 | A | 7/1908 | Conner |
| 2,212,334 | A | 8/1940 | Wallerich |
| 2,767,703 | A | 10/1956 | Nieburgs |
| 3,334,629 | A | 8/1967 | Cohn |
| 3,472,230 | A | 10/1969 | Fogarty |
| 3,540,431 | A | 11/1970 | Mobin-Uddia |
| 3,579,798 | A | 5/1971 | Henderson |
| 3,620,212 | A | 11/1971 | Fannon, Jr. et al. |
| 3,657,744 | A | 4/1972 | Ersek |
| 3,875,928 | A | 4/1975 | Angelchik |
| 3,885,562 | A | 5/1975 | Lampkin |
| 3,952,747 | A | 4/1976 | Kimmell, Jr. |
| 4,000,739 | A | 1/1977 | Stevens |
| 4,041,931 | A | 8/1977 | Elliott et al. |
| 4,198,960 | A | 4/1980 | Utsugi et al. |
| 4,256,132 | A | 3/1981 | Gunter |

(Continued)

FOREIGN PATENT DOCUMENTS

| | | |
|---|---|---|
| CA | 2173118 A1 | 4/1995 |
| CA | 2648325 A1 | 4/2000 |

(Continued)

OTHER PUBLICATIONS

C.R. Bard Simon Nitinol Filter: For Use in the Vena Cava: Instructions for Use (1995, 1997).

(Continued)

*Primary Examiner* — Elizabeth Houston
(74) *Attorney, Agent, or Firm* — Rutan & Tucker, LLP

(57) ABSTRACT

A blood filter delivery system for delivering a filter into a vein includes an introducer and a push rod with a spline member disposed along the push rod. The spline member has a main body, and first and second boss portions spaced apart along the longitudinal axis to provide a gap for retaining anchor member of the filter during delivery via the introducer.

10 Claims, 13 Drawing Sheets

U.S. PATENT DOCUMENTS

| | | | |
|---|---|---|---|
| 4,282,876 A | 8/1981 | Flynn | |
| 4,283,447 A | 8/1981 | Flynn | |
| 4,317,446 A | 3/1982 | Ambrosio et al. | |
| 4,334,536 A | 6/1982 | Pfleger | |
| 4,343,048 A | 8/1982 | Ross et al. | |
| 4,411,655 A | 10/1983 | Schreck | |
| 4,419,095 A | 12/1983 | Nebergall et al. | |
| 4,425,908 A | 1/1984 | Simon | |
| 4,494,531 A | 1/1985 | Gianturco | |
| 4,562,596 A | 1/1986 | Kornberg | |
| 4,572,186 A | 2/1986 | Gould et al. | |
| 4,586,501 A | 5/1986 | Claracq et al. | |
| 4,588,399 A | 5/1986 | Nebergall et al. | |
| 4,590,938 A | 5/1986 | Segura et al. | |
| 4,611,594 A | 9/1986 | Grayhack et al. | |
| 4,619,246 A | 10/1986 | Molgaard-Nielsen et al. | |
| 4,643,184 A | 2/1987 | Mobin-Uddin | |
| 4,655,219 A | 4/1987 | Petruzzi | |
| 4,655,771 A | 4/1987 | Wallsten | |
| 4,657,024 A | 4/1987 | Coneys | |
| 4,665,906 A | 5/1987 | Jervis | |
| 4,680,573 A | 7/1987 | Ciordinik et al. | |
| 4,688,553 A | 8/1987 | Metals et al. | |
| 4,710,192 A | 12/1987 | Liotta et al. | |
| 4,722,344 A | 2/1988 | Cambron et al. | |
| 4,727,873 A | 3/1988 | Mobin-Uddin | |
| 4,735,616 A | 4/1988 | Eibl et al. | |
| 4,781,177 A | 11/1988 | Lebigot et al. | |
| 4,793,348 A | 12/1988 | Palmaz | |
| 4,798,591 A | 1/1989 | Okada et al. | |
| 4,817,600 A | 4/1989 | Herms et al. | |
| 4,832,055 A | 5/1989 | Palestrant | |
| 4,838,879 A | 6/1989 | Tanabe et al. | |
| 4,857,062 A | 8/1989 | Russell | |
| 4,863,442 A | 9/1989 | DeMello et al. | |
| 4,873,978 A | 10/1989 | Ginsburg | |
| 4,886,506 A | 12/1989 | Lovgren et al. | |
| 4,888,506 A | 12/1989 | Umehara et al. | |
| 4,898,591 A | 2/1990 | Jang et al. | |
| 4,915,695 A | 4/1990 | Koobs | |
| 4,922,905 A | 5/1990 | Strecker et al. | |
| 4,943,297 A | 7/1990 | Saveliev et al. | |
| 4,950,227 A | 8/1990 | Savin et al. | |
| 4,957,501 A | 9/1990 | Lahille et al. | |
| 4,969,891 A | 11/1990 | Gewertz | |
| 4,990,151 A | 2/1991 | Wallsten | |
| 4,990,156 A | 2/1991 | Lefebvre | |
| 5,045,072 A | 9/1991 | Castillo et al. | |
| 5,059,205 A | 10/1991 | El-Nounou et al. | |
| 5,067,957 A | 11/1991 | Jervis | |
| 5,074,867 A | 12/1991 | Wilk | |
| 5,098,440 A | 3/1992 | Hillstead | |
| 5,108,418 A | 4/1992 | Lefebvre et al. | |
| 5,114,408 A | 5/1992 | Fleischhaker et al. | |
| 5,120,308 A | 6/1992 | Hess | |
| 5,133,733 A | 7/1992 | Rasmussen et al. | |
| 5,147,378 A | 9/1992 | Markham | |
| 5,147,379 A | 9/1992 | Sabbaghian et al. | |
| 5,152,777 A | 10/1992 | Goldberg et al. | |
| 5,171,232 A | 12/1992 | Castillo et al. | |
| 5,188,616 A | 2/1993 | Nadal et al. | |
| 5,190,546 A | 3/1993 | Jervis | |
| 5,203,776 A | 4/1993 | Durfee | |
| 5,219,358 A | 6/1993 | Bendel et al. | |
| 5,234,416 A | 8/1993 | Macaulay et al. | |
| 5,234,458 A | 8/1993 | Metais et al. | |
| 5,242,462 A | 9/1993 | El-Nounou et al. | |
| 5,292,331 A | 3/1994 | Boneau | |
| 5,300,086 A | 4/1994 | Gory et al. | |
| 5,304,156 A | 4/1994 | Sylvanowicz et al. | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,398 A | 9/1994 | Pavcnik et al. | |
| 5,358,493 A | 10/1994 | Schweich, Jr. et al. | |
| 5,370,657 A | 12/1994 | Irie | |
| 5,375,612 A | 12/1994 | Cottenceau et al. | |
| 5,383,887 A | 1/1995 | Nadal et al. | |
| 5,397,310 A | 3/1995 | Chu et al. | |
| 5,397,355 A | 3/1995 | Marin et al. | |
| 5,413,586 A | 5/1995 | Dibie et al. | |
| 5,421,832 A | 6/1995 | Lefebvre et al. | |
| 5,423,851 A | 6/1995 | Samuels | |
| 5,443,497 A | 8/1995 | Venbrux | |
| 5,464,408 A | 11/1995 | Duc | |
| 5,485,667 A | 1/1996 | Kleshinski | |
| 5,514,154 A | 5/1996 | Lau et al. | |
| 5,531,788 A | 7/1996 | Dibie et al. | |
| 5,545,151 A | 8/1996 | O'Connor et al. | |
| 5,545,210 A | 8/1996 | Hess et al. | |
| 5,549,576 A | 8/1996 | Patterson et al. | |
| 5,549,626 A | 8/1996 | Miller et al. | |
| 5,554,181 A | 9/1996 | Das | |
| 5,558,652 A | 9/1996 | Henke | |
| 5,562,698 A | 10/1996 | Parker | |
| 5,562,728 A | 10/1996 | Lazarus et al. | |
| 5,591,197 A | 1/1997 | Orth et al. | |
| 5,593,417 A | 1/1997 | Rhodes | |
| 5,593,434 A | 1/1997 | Williams | |
| 5,597,378 A | 1/1997 | Jervis | |
| 5,601,568 A | 2/1997 | Chevillon et al. | |
| 5,601,595 A | 2/1997 | Smith | |
| 5,603,721 A | 2/1997 | Lau et al. | |
| 5,624,508 A | 4/1997 | Flomenblit et al. | |
| 5,626,605 A | 5/1997 | Irie et al. | |
| 5,630,822 A | 5/1997 | Hermann et al. | |
| 5,634,942 A | 6/1997 | Chevillon et al. | |
| 5,641,364 A | 6/1997 | Golberg et al. | |
| 5,649,906 A | 7/1997 | Gory et al. | |
| 5,669,879 A | 9/1997 | Duer et al. | |
| 5,669,933 A | 9/1997 | Simon et al. | |
| 5,672,153 A | 9/1997 | Lax et al. | |
| 5,672,158 A | 9/1997 | Okada et al. | |
| 5,674,278 A | 10/1997 | Boneau | |
| 5,681,347 A | 10/1997 | Cathcart et al. | |
| 5,683,411 A | 11/1997 | Kavteladze et al. | |
| 5,695,518 A | 12/1997 | Laerum et al. | |
| 5,695,519 A | 12/1997 | Summers et al. | |
| 5,702,370 A | 12/1997 | Sylvanowicz et al. | |
| 5,704,910 A | 1/1998 | Humes | |
| 5,704,926 A | 1/1998 | Sutton | |
| 5,704,928 A | 1/1998 | Morita et al. | |
| 5,707,376 A | 1/1998 | Kavteladze et al. | |
| 5,709,704 A | 1/1998 | Nott et al. | |
| 5,720,762 A | 2/1998 | Bass | |
| 5,720,764 A | 2/1998 | Naderlinger | |
| 5,720,776 A | 2/1998 | Chuter et al. | |
| 5,725,550 A | 3/1998 | Nadal et al. | |
| 5,746,767 A | 5/1998 | Smith | |
| 5,755,790 A | 5/1998 | Chevillon et al. | |
| 5,759,192 A | 6/1998 | Saunders | |
| 5,769,816 A | 6/1998 | Barbut et al. | |
| 5,775,790 A | 7/1998 | Ohtake | |
| 5,776,162 A | 7/1998 | Kleshinski | |
| 5,776,181 A | 7/1998 | Lee et al. | |
| 5,780,807 A | 7/1998 | Saunders | |
| 5,800,457 A | 9/1998 | Gelbfish | |
| 5,800,515 A | 9/1998 | Nadal et al. | |
| 5,800,526 A | 9/1998 | Anderson et al. | |
| 5,830,222 A | 11/1998 | Makower | |
| 5,836,968 A | 11/1998 | Simon et al. | |
| 5,836,969 A | 11/1998 | Kim et al. | |
| 5,843,164 A | 12/1998 | Frantzen et al. | |
| 5,843,167 A | 12/1998 | Dwyer et al. | |
| 5,853,420 A | 12/1998 | Chevillon et al. | |
| 5,879,382 A | 3/1999 | Boneau | |
| 5,891,190 A | 4/1999 | Boneau | |
| 5,893,867 A | 4/1999 | Bagaoisan et al. | |
| 5,893,869 A | 4/1999 | Barnhart et al. | |
| 5,896,869 A | 4/1999 | Maniscalco et al. | |
| 5,897,497 A | 4/1999 | Fernandez | |
| 5,911,704 A | 6/1999 | Humes | |
| 5,919,224 A | 7/1999 | Thompson et al. | |
| 5,928,261 A | 7/1999 | Ruiz | |
| 5,935,162 A | 8/1999 | Dang | |
| 5,938,683 A | 8/1999 | Lefebvre | |
| 5,944,728 A | 8/1999 | Bates | |

| | | | |
|---|---|---|---|
| 5,951,585 A | 9/1999 | Cathcart et al. |
| 5,954,741 A | 9/1999 | Fox et al. |
| 5,961,546 A | 10/1999 | Robinson et al. |
| 5,968,052 A | 10/1999 | Sullivan, III et al. |
| 5,968,071 A | 10/1999 | Chevillon et al. |
| 5,972,019 A | 10/1999 | Engelson et al. |
| 5,976,172 A | 11/1999 | Homsma et al. |
| 5,984,947 A | 11/1999 | Smith |
| 5,989,266 A | 11/1999 | Foster |
| 6,001,118 A | 12/1999 | Daniel et al. |
| 6,004,347 A | 12/1999 | McNamara et al. |
| 6,007,558 A | 12/1999 | Ravenscroft et al. |
| 6,013,093 A | 1/2000 | Nott et al. |
| 6,036,723 A | 3/2000 | Anidjar et al. |
| 6,051,015 A | 4/2000 | Maahs |
| 6,059,814 A | 5/2000 | Ladd |
| 6,059,825 A | 5/2000 | Hobbs et al. |
| 6,066,158 A | 5/2000 | Engelson et al. |
| 6,068,638 A | 5/2000 | Makower |
| 6,068,645 A | 5/2000 | Tu |
| 6,071,292 A | 6/2000 | Makower et al. |
| 6,071,307 A | 6/2000 | Rhee et al. |
| 6,077,297 A | 6/2000 | Robinson et al. |
| 6,077,880 A | 6/2000 | Castillo et al. |
| 6,080,178 A | 6/2000 | Meglin |
| 6,099,534 A | 8/2000 | Bates et al. |
| 6,099,549 A | 8/2000 | Bosma et al. |
| 6,102,932 A | 8/2000 | Kurz |
| 6,113,608 A | 9/2000 | Monroe et al. |
| 6,126,645 A | 10/2000 | Thompson |
| 6,126,673 A | 10/2000 | Kim et al. |
| 6,131,266 A | 10/2000 | Saunders |
| 6,132,388 A | 10/2000 | Fleming et al. |
| 6,146,404 A | 11/2000 | Kim et al. |
| 6,156,055 A | 12/2000 | Ravenscroft |
| 6,159,225 A | 12/2000 | Makower |
| 6,162,357 A | 12/2000 | Pakki et al. |
| 6,165,179 A | 12/2000 | Cathcart et al. |
| 6,165,200 A | 12/2000 | Tsugita et al. |
| 6,171,297 B1 | 1/2001 | Pedersen et al. |
| 6,190,353 B1 | 2/2001 | Makower et al. |
| 6,193,739 B1 | 2/2001 | Chevillon et al. |
| 6,193,748 B1 | 2/2001 | Thompson et al. |
| 6,206,888 B1 | 3/2001 | Bicek et al. |
| 6,214,025 B1 | 4/2001 | Thistle et al. |
| 6,217,600 B1 | 4/2001 | DiMatteo |
| 6,228,052 B1 | 5/2001 | Pohndorf |
| 6,231,581 B1 | 5/2001 | Shank et al. |
| 6,231,587 B1 | 5/2001 | Makower |
| 6,231,588 B1 | 5/2001 | Zadno-Azizi |
| 6,231,589 B1 | 5/2001 | Wessman et al. |
| 6,235,045 B1 | 5/2001 | Barbut et al. |
| 6,241,738 B1 | 6/2001 | Dereume |
| 6,241,746 B1 | 6/2001 | Bosma et al. |
| 6,245,012 B1 | 6/2001 | Kleshinski |
| 6,245,099 B1 | 6/2001 | Edwin et al. |
| 6,251,122 B1 | 6/2001 | Tsukernik |
| 6,254,609 B1 | 7/2001 | Vrba et al. |
| 6,254,633 B1 | 7/2001 | Pinchuk et al. |
| 6,258,026 B1 | 7/2001 | Ravenscroft et al. |
| 6,258,101 B1 | 7/2001 | Blake, III |
| 6,264,664 B1 | 7/2001 | Avellanet |
| 6,264,671 B1 | 7/2001 | Stack et al. |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,280,451 B1 | 8/2001 | Bates et al. |
| 6,280,459 B1 | 8/2001 | Doble |
| 6,282,222 B1 | 8/2001 | Wieser et al. |
| 6,283,983 B1 | 9/2001 | Makower et al. |
| 6,287,317 B1 | 9/2001 | Makower et al. |
| 6,287,332 B1 | 9/2001 | Bolz et al. |
| 6,287,335 B1 | 9/2001 | Drasler et al. |
| 6,290,710 B1 | 9/2001 | Cryer et al. |
| 6,302,875 B1 | 10/2001 | Makower et al. |
| 6,302,891 B1 | 10/2001 | Nadal et al. |
| 6,306,163 B1 | 10/2001 | Fitz |
| 6,322,541 B2 | 11/2001 | West et al. |
| 6,325,790 B1 | 12/2001 | Trotta |
| 6,328,755 B1 | 12/2001 | Marshall |
| 6,331,183 B1 | 12/2001 | Suon |
| 6,336,934 B1 | 1/2002 | Gilson et al. |
| 6,342,062 B1 | 1/2002 | Suon et al. |
| 6,342,063 B1 | 1/2002 | DeVries et al. |
| 6,344,053 B1 | 2/2002 | Boneau |
| 6,355,056 B1 | 3/2002 | Pinheiro |
| 6,361,546 B1 | 3/2002 | Khosravi |
| 6,383,193 B1 | 5/2002 | Cathcart et al. |
| 6,383,195 B1 | 5/2002 | Richard |
| 6,383,206 B1 | 5/2002 | Gillick et al. |
| 6,391,045 B1 | 5/2002 | Kim et al. |
| 6,402,771 B1 | 6/2002 | Palmer et al. |
| 6,416,530 B2 | 7/2002 | DeVries et al. |
| 6,425,909 B1 | 7/2002 | Dieck et al. |
| 6,428,559 B1 | 8/2002 | Johnson |
| 6,432,127 B1 | 8/2002 | Kim et al. |
| 6,436,120 B1 | 8/2002 | Meglin |
| 6,436,121 B1 | 8/2002 | Blom |
| 6,440,077 B1 | 8/2002 | Jung et al. |
| 6,442,413 B1 | 8/2002 | Silver |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,458,145 B1 | 10/2002 | Ravenscroft et al. |
| 6,468,290 B1 | 10/2002 | Weldon et al. |
| 6,482,222 B1 | 11/2002 | Bruckheimer et al. |
| 6,485,500 B1 | 11/2002 | Kokish et al. |
| 6,485,501 B1 | 11/2002 | Green |
| 6,485,502 B2 | 11/2002 | Don Michael et al. |
| 6,488,662 B2 | 12/2002 | Sirimanne |
| 6,497,709 B1 | 12/2002 | Heath |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,503 B1 | 1/2003 | Burkett et al. |
| 6,517,559 B1 | 2/2003 | O'Connell |
| 6,517,573 B1 | 2/2003 | Pollock et al. |
| 6,527,962 B1 | 3/2003 | Nadal |
| 6,537,294 B1 | 3/2003 | Boyle et al. |
| 6,537,295 B2 | 3/2003 | Petersen |
| 6,537,296 B2 | 3/2003 | Levinson et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,280 B1 | 4/2003 | Daniel et al. |
| 6,551,303 B1 | 4/2003 | Van Tassel et al. |
| 6,551,340 B1 | 4/2003 | Konya et al. |
| 6,551,342 B1 | 4/2003 | Shen et al. |
| 6,558,404 B2 | 5/2003 | Tsukernik |
| 6,558,405 B1 | 5/2003 | McInnes |
| 6,558,406 B2 | 5/2003 | Okada et al. |
| 6,563,080 B2 | 5/2003 | Shapovalov et al. |
| 6,569,183 B1 | 5/2003 | Kim et al. |
| 6,569,184 B2 | 5/2003 | Huter |
| 6,572,605 B1 | 6/2003 | Humes |
| 6,575,997 B1 | 6/2003 | Palmer et al. |
| 6,579,314 B1 | 6/2003 | Lombardi et al. |
| 6,582,447 B1 | 6/2003 | Patel et al. |
| 6,589,266 B2 | 7/2003 | Whitcher et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,602,226 B1 | 8/2003 | Smith et al. |
| 6,602,273 B2 | 8/2003 | Marshall |
| 6,607,553 B1 | 8/2003 | Healy et al. |
| 6,610,077 B1 | 8/2003 | Hancock et al. |
| 6,616,680 B1 | 9/2003 | Thielen |
| 6,616,681 B2 | 9/2003 | Hanson et al. |
| 6,620,183 B2 | 9/2003 | DiMatteo |
| 6,623,450 B2 | 9/2003 | Dutta |
| 6,623,506 B2 | 9/2003 | McGuckin, Jr. et al. |
| 6,629,993 B2 | 10/2003 | Voinov et al. |
| 6,638,293 B1 | 10/2003 | Makower et al. |
| 6,640,077 B2 | 10/2003 | Suzuki et al. |
| 6,641,590 B1 | 11/2003 | Palmer et al. |
| 6,645,152 B1 | 11/2003 | Jung et al. |
| 6,645,224 B2 | 11/2003 | Gilson et al. |

| | | | | | |
|---|---|---|---|---|---|
| 6,652,555 B1 | 11/2003 | VanTassel et al. | 7,749,246 B2 | 7/2010 | McGuckin, Jr. et al. |
| 6,652,556 B1 | 11/2003 | VanTassel et al. | 7,766,932 B2 | 8/2010 | Melzer et al. |
| 6,652,558 B2 | 11/2003 | Patel et al. | 7,794,472 B2 | 9/2010 | Eidenschink et al. |
| 6,652,692 B2 | 11/2003 | Pedersen et al. | 7,799,049 B2 | 9/2010 | Ostrovsky et al. |
| 6,656,203 B2 | 12/2003 | Roth et al. | 7,887,580 B2 | 2/2011 | Randall et al. |
| 6,660,021 B1 | 12/2003 | Palmer et al. | 7,967,838 B2 | 6/2011 | Chanduszko et al. |
| 6,660,031 B2 | 12/2003 | Tran et al. | 7,972,353 B2 | 7/2011 | Hendriksen et al. |
| 6,663,650 B2 | 12/2003 | Sepetka et al. | 7,993,362 B2 | 8/2011 | Lowe et al. |
| 6,679,902 B1 | 1/2004 | Boyle et al. | 8,029,529 B1 | 10/2011 | Chanduszko |
| 6,679,903 B2 | 1/2004 | Kurz | 8,062,327 B2 | 11/2011 | Chanduszko et al. |
| 6,682,540 B1 | 1/2004 | Sancoff et al. | 8,075,606 B2 | 12/2011 | Dorn |
| 6,685,722 B1 | 2/2004 | Rosenbluth et al. | 8,133,251 B2 | 3/2012 | Ravenscroft et al. |
| 6,685,738 B2 | 2/2004 | Chouinard et al. | 8,241,350 B2 | 8/2012 | Randall et al. |
| 6,689,150 B1 | 2/2004 | VanTassel et al. | 2001/0000799 A1 | 5/2001 | Wessman et al. |
| 6,695,813 B1 | 2/2004 | Boyle et al. | 2001/0001317 A1 | 5/2001 | Duerig et al. |
| 6,696,667 B1 | 2/2004 | Flanagan et al. | 2001/0016770 A1 | 8/2001 | Allen et al. |
| 6,702,834 B1 | 3/2004 | Boylan et al. | 2001/0020175 A1 | 9/2001 | Yassour et al. |
| 6,702,843 B1 | 3/2004 | Brown et al. | 2001/0023358 A1 | 9/2001 | Tsukernik |
| 6,706,054 B2 | 3/2004 | Wessman et al. | 2001/0027339 A1 | 10/2001 | Boatman et al. |
| 6,712,834 B2 | 3/2004 | Yassour et al. | 2001/0039431 A1 | 11/2001 | DeVries et al. |
| 6,716,208 B2 | 4/2004 | Humes | 2002/0002401 A1 | 1/2002 | McGuckin et al. |
| 6,719,717 B1 | 4/2004 | Johnson et al. | 2002/0004060 A1 | 1/2002 | Heublein et al. |
| 6,719,772 B2 | 4/2004 | Trask et al. | 2002/0010350 A1 | 1/2002 | Tatsumi et al. |
| 6,726,621 B2 | 4/2004 | Suon et al. | 2002/0022853 A1 | 2/2002 | Swanson et al. |
| 6,730,108 B2 | 5/2004 | Van Tassel et al. | 2002/0032461 A1 | 3/2002 | Marshall |
| 6,736,842 B2 | 5/2004 | Healy et al. | 2002/0038097 A1 | 3/2002 | Corvi et al. |
| 6,752,819 B1 | 6/2004 | Brady et al. | 2002/0042626 A1 | 4/2002 | Hanson et al. |
| 6,755,846 B1 | 6/2004 | Yadav | 2002/0045918 A1 | 4/2002 | Suon et al. |
| 6,761,732 B2 | 7/2004 | Burkett et al. | 2002/0052626 A1 | 5/2002 | Gilson et al. |
| 6,773,448 B2 | 8/2004 | Kusleika et al. | 2002/0055767 A1 | 5/2002 | Forde et al. |
| 6,776,770 B1 | 8/2004 | Trerotola | 2002/0072764 A1 | 6/2002 | Sepetka et al. |
| 6,776,774 B2 | 8/2004 | Tansey, Jr. et al. | 2002/0116024 A1 | 8/2002 | Goldberg et al. |
| 6,783,538 B2 | 8/2004 | McGuckin, Jr. et al. | 2002/0123720 A1 | 9/2002 | Kusleika et al. |
| 6,792,979 B2 | 9/2004 | Konya et al. | 2002/0138097 A1 | 9/2002 | Ostrovsky et al. |
| 6,793,665 B2 | 9/2004 | McGuckin, Jr. et al. | 2002/0193825 A1 | 12/2002 | McGuckin et al. |
| 6,818,006 B2 | 11/2004 | Douk et al. | 2002/0193826 A1 | 12/2002 | McGuckin et al. |
| 6,837,898 B2 | 1/2005 | Boyle et al. | 2002/0193827 A1 | 12/2002 | McGuckin et al. |
| 6,840,950 B2 | 1/2005 | Stanford et al. | 2002/0193828 A1 | 12/2002 | Griffin et al. |
| 6,843,798 B2 | 1/2005 | Kusleika et al. | 2003/0004540 A1 | 1/2003 | Linder et al. |
| 6,849,061 B2 | 2/2005 | Wagner | 2003/0004541 A1 | 1/2003 | Linder et al. |
| 6,852,076 B2 | 2/2005 | Nikolic et al. | 2003/0004946 A1 | 1/2003 | VanDenAvond et al. |
| 6,872,217 B2 | 3/2005 | Walak et al. | 2003/0028241 A1 | 2/2003 | Stinson |
| 6,881,218 B2 | 4/2005 | Beyer et al. | 2003/0055812 A1 | 3/2003 | Williams et al. |
| 6,884,259 B2 | 4/2005 | Tran et al. | 2003/0071285 A1 | 4/2003 | Tsukernik |
| 6,887,256 B2 | 5/2005 | Gilson et al. | 2003/0093106 A1 | 5/2003 | Brady et al. |
| 6,972,025 B2 | 12/2005 | WasDyke | 2003/0093110 A1 | 5/2003 | Vale |
| 6,989,021 B2 | 1/2006 | Bosma et al. | 2003/0097145 A1 | 5/2003 | Goldberg et al. |
| 6,991,641 B2 | 1/2006 | Diaz et al. | 2003/0109824 A1 | 6/2003 | Anderson et al. |
| 6,991,642 B2 | 1/2006 | Petersen | 2003/0109897 A1 | 6/2003 | Walak et al. |
| 7,001,424 B2 | 2/2006 | Patel et al. | 2003/0114735 A1 | 6/2003 | Silver et al. |
| 7,011,094 B2 | 3/2006 | Rapacki et al. | 2003/0114880 A1 | 6/2003 | Hansen et al. |
| 7,033,376 B2 | 4/2006 | Tsukernik | 2003/0130680 A1 | 7/2003 | Russell |
| 7,041,117 B2 | 5/2006 | Suon et al. | 2003/0139765 A1 | 7/2003 | Patel et al. |
| 7,052,511 B2 | 5/2006 | Weldon et al. | 2003/0153945 A1 | 8/2003 | Patel et al. |
| 7,056,286 B2 | 6/2006 | Ravenscroft et al. | 2003/0158595 A1 | 8/2003 | Randall et al. |
| 7,147,649 B2 | 12/2006 | Thomas | 2003/0163159 A1 | 8/2003 | Patel et al. |
| 7,163,550 B2 | 1/2007 | Boismier | 2003/0171771 A1 | 9/2003 | Anderson et al. |
| 7,179,275 B2 | 2/2007 | McGuckin, Jr. et al. | 2003/0176888 A1 | 9/2003 | O'Connell |
| 7,232,462 B2 | 6/2007 | Schaeffer | 2003/0176912 A1 | 9/2003 | Chuter et al. |
| 7,261,731 B2 | 8/2007 | Patel et al. | 2003/0191516 A1 | 10/2003 | Weldon et al. |
| 7,279,000 B2 | 10/2007 | Cartier et al. | 2003/0195554 A1 | 10/2003 | Shen et al. |
| 7,303,571 B2 | 12/2007 | Makower et al. | 2003/0195556 A1 | 10/2003 | Stack et al. |
| 7,314,477 B1 | 1/2008 | Ravenscroft et al. | 2003/0199918 A1 | 10/2003 | Patel et al. |
| 7,323,003 B2 | 1/2008 | Lowe | 2003/0208227 A1 | 11/2003 | Thomas |
| 7,331,992 B2 | 2/2008 | Randall et al. | 2003/0208229 A1 | 11/2003 | Kletschka |
| 7,338,512 B2 | 3/2008 | McGuckin, Jr. et al. | 2003/0208253 A1 | 11/2003 | Beyer et al. |
| 7,534,251 B2 | 5/2009 | WasDyke | 2003/0220683 A1 | 11/2003 | Minasian et al. |
| 7,544,202 B2 | 6/2009 | Cartier et al. | 2004/0006364 A1 | 1/2004 | Ladd |
| 7,572,289 B2 | 8/2009 | Sisken et al. | 2004/0006369 A1 | 1/2004 | DiMatteo |
| 7,582,100 B2 | 9/2009 | Johnson et al. | 2004/0059373 A1 | 3/2004 | Shapiro et al. |
| 7,625,390 B2 | 12/2009 | Hendriksen et al. | 2004/0068288 A1 | 4/2004 | Palmer |
| 7,699,867 B2 | 4/2010 | Hendriksen et al. | 2004/0073252 A1 | 4/2004 | Goldberg et al. |
| 7,704,266 B2 | 4/2010 | Thinnes, Jr. et al. | 2004/0082966 A1 | 4/2004 | WasDyke |
| 7,704,267 B2 | 4/2010 | Tessmer | 2004/0087999 A1 | 5/2004 | Bosma et al. |
| 7,722,635 B2 | 5/2010 | Beyer et al. | 2004/0088000 A1 | 5/2004 | Muller |
| 7,722,638 B2 | 5/2010 | Deyette, Jr. et al. | 2004/0088001 A1 | 5/2004 | Bosma et al. |
| 7,736,383 B2 | 6/2010 | Bressler et al. | 2004/0088002 A1 | 5/2004 | Boyle et al. |
| 7,736,384 B2 | 6/2010 | Bressler et al. | 2004/0093015 A1 | 5/2004 | Ogle |
| 7,749,244 B2 | 7/2010 | Brucheimer et al. | 2004/0093064 A1 | 5/2004 | Bosma |

| | | |
|---|---|---|
| 2004/0116959 A1 | 6/2004 | McGuckin et al. |
| 2004/0138693 A1 | 7/2004 | Eskuri et al. |
| 2004/0153110 A1 | 8/2004 | Kurz et al. |
| 2004/0153118 A1 | 8/2004 | Clubb et al. |
| 2004/0153119 A1 | 8/2004 | Kusleika et al. |
| 2004/0158267 A1 | 8/2004 | Sancoff et al. |
| 2004/0158273 A1 | 8/2004 | Weaver et al. |
| 2004/0158274 A1 | 8/2004 | WasDyke |
| 2004/0167568 A1 | 8/2004 | Boyle et al. |
| 2004/0172042 A1 | 9/2004 | Suon et al. |
| 2004/0176672 A1 | 9/2004 | Silver et al. |
| 2004/0186510 A1 | 9/2004 | Weaver |
| 2004/0186512 A1 | 9/2004 | Bruckheimer et al. |
| 2004/0193209 A1 | 9/2004 | Pavcnik et al. |
| 2004/0199240 A1 | 10/2004 | Dorn |
| 2004/0199270 A1 | 10/2004 | Wang et al. |
| 2004/0220610 A1 | 11/2004 | Kreidler et al. |
| 2004/0220611 A1 | 11/2004 | Ogle |
| 2004/0230220 A1 | 11/2004 | Osborne |
| 2004/0243173 A1 | 12/2004 | Inoue |
| 2005/0004596 A1 | 1/2005 | McGuckin et al. |
| 2005/0015111 A1 | 1/2005 | McGuckin et al. |
| 2005/0019370 A1 | 1/2005 | Humes |
| 2005/0021075 A1 | 1/2005 | Bonnette et al. |
| 2005/0021076 A1 | 1/2005 | Mazzocchi et al. |
| 2005/0021152 A1 | 1/2005 | Ogle et al. |
| 2005/0027314 A1 | 2/2005 | WasDyke |
| 2005/0027345 A1 | 2/2005 | Horan et al. |
| 2005/0049609 A1 | 3/2005 | Gunderson et al. |
| 2005/0055045 A1 | 3/2005 | DeVries et al. |
| 2005/0055046 A1 | 3/2005 | McGuckin et al. |
| 2005/0059990 A1 | 3/2005 | Ayala et al. |
| 2005/0059993 A1 | 3/2005 | Ramzipoor et al. |
| 2005/0065591 A1 | 3/2005 | Moberg et al. |
| 2005/0070794 A1 | 3/2005 | Deal et al. |
| 2005/0070821 A1 | 3/2005 | Deal et al. |
| 2005/0080447 A1 | 4/2005 | McGuckin et al. |
| 2005/0080449 A1 | 4/2005 | Mulder |
| 2005/0085847 A1 | 4/2005 | Galdonik et al. |
| 2005/0090858 A1 | 4/2005 | Pavlovic |
| 2005/0101982 A1 | 5/2005 | Ravenscroft et al. |
| 2005/0107822 A1 | 5/2005 | WasDyke |
| 2005/0115111 A1 | 6/2005 | Yamashita et al. |
| 2005/0131451 A1 | 6/2005 | Kleshinski et al. |
| 2005/0131452 A1 | 6/2005 | Walak et al. |
| 2005/0159771 A1 | 7/2005 | Petersen |
| 2005/0165441 A1 | 7/2005 | McGuckin et al. |
| 2005/0165442 A1 | 7/2005 | Thinnes et al. |
| 2005/0171473 A1 | 8/2005 | Gerdts et al. |
| 2005/0182439 A1 | 8/2005 | Lowe |
| 2005/0222604 A1 | 10/2005 | Schaeffer |
| 2005/0234503 A1 | 10/2005 | Ravenscroft et al. |
| 2005/0251199 A1 | 11/2005 | Osborne et al. |
| 2005/0267512 A1 | 12/2005 | Osborne et al. |
| 2005/0267513 A1 | 12/2005 | Osborne et al. |
| 2005/0267514 A1 | 12/2005 | Osborne et al. |
| 2005/0267515 A1 | 12/2005 | Oliva et al. |
| 2005/0288703 A1 | 12/2005 | Beyer et al. |
| 2005/0288704 A1 | 12/2005 | Cartier et al. |
| 2006/0004402 A1 | 1/2006 | Voeller et al. |
| 2006/0015137 A1 | 1/2006 | WasDyke et al. |
| 2006/0016299 A1 | 1/2006 | Chen |
| 2006/0030875 A1 | 2/2006 | Tessmer |
| 2006/0036279 A1 | 2/2006 | Eidenschink et al. |
| 2006/0041271 A1 | 2/2006 | Bosma et al. |
| 2006/0047300 A1 | 3/2006 | Eidenschink |
| 2006/0047341 A1 | 3/2006 | Trieu |
| 2006/0069405 A1 | 3/2006 | Schaeffer et al. |
| 2006/0069406 A1 | 3/2006 | Hendriksen et al. |
| 2006/0079928 A1 | 4/2006 | Cartier et al. |
| 2006/0079930 A1 | 4/2006 | McGuckin et al. |
| 2006/0095068 A1 | 5/2006 | WasDyke et al. |
| 2006/0106417 A1 | 5/2006 | Tessmer et al. |
| 2006/0155320 A1 | 7/2006 | Bressler et al. |
| 2006/0157889 A1 | 7/2006 | Chen |
| 2006/0203769 A1 | 9/2006 | Saholt et al. |
| 2006/0206138 A1 | 9/2006 | Eidenschink |
| 2006/0259067 A1 | 11/2006 | Welch et al. |
| 2006/0259068 A1 | 11/2006 | Eidenschink |
| 2007/0005095 A1 | 1/2007 | Osborne et al. |
| 2007/0005104 A1 | 1/2007 | Kusleika et al. |
| 2007/0005105 A1 | 1/2007 | Kusleika et al. |
| 2007/0039432 A1 | 2/2007 | Cutler |
| 2007/0043419 A1 | 2/2007 | Nikolchev et al. |
| 2007/0060944 A1 | 3/2007 | Boldenow et al. |
| 2007/0088381 A1 | 4/2007 | McGuckin et al. |
| 2007/0100372 A1 | 5/2007 | Schaeffer |
| 2007/0112373 A1 | 5/2007 | Carr et al. |
| 2007/0167974 A1 | 7/2007 | Cully et al. |
| 2007/0173885 A1 | 7/2007 | Cartier et al. |
| 2007/0185524 A1 | 8/2007 | Diaz et al. |
| 2007/0191878 A1 | 8/2007 | Segner et al. |
| 2007/0191880 A1 | 8/2007 | Cartier et al. |
| 2007/0198050 A1 | 8/2007 | Ravenscroft et al. |
| 2007/0213685 A1 | 9/2007 | Bressler et al. |
| 2007/0219530 A1 | 9/2007 | Schaeffer |
| 2007/0250106 A1 | 10/2007 | Kim |
| 2008/0014078 A1 | 1/2008 | Suciu et al. |
| 2008/0033479 A1 | 2/2008 | Silver |
| 2008/0039891 A1 | 2/2008 | McGuckin et al. |
| 2008/0091230 A1 | 4/2008 | Lowe |
| 2008/0097518 A1 | 4/2008 | Thinnes et al. |
| 2008/0103582 A1 | 5/2008 | Randall et al. |
| 2008/0119867 A1 | 5/2008 | Delaney |
| 2008/0183206 A1 | 7/2008 | Batiste |
| 2008/0221609 A1 | 9/2008 | McGuckin et al. |
| 2008/0221656 A1 | 9/2008 | Hartley et al. |
| 2008/0255605 A1 | 10/2008 | Weidman |
| 2008/0262506 A1 | 10/2008 | Griffin et al. |
| 2008/0275486 A1 | 11/2008 | Dwyer et al. |
| 2008/0275488 A1 | 11/2008 | Fleming |
| 2008/0294189 A1 | 11/2008 | Moll et al. |
| 2008/0300621 A1 | 12/2008 | Hopkins et al. |
| 2009/0005803 A1 | 1/2009 | Batiste |
| 2009/0043332 A1 | 2/2009 | Sullivan et al. |
| 2009/0069840 A1 | 3/2009 | Hallisey |
| 2009/0105747 A1 | 4/2009 | Chanduszko et al. |
| 2009/0131970 A1 | 5/2009 | Chanduszko et al. |
| 2009/0163926 A1 | 6/2009 | Sos |
| 2009/0192543 A1 | 7/2009 | WasDyke |
| 2009/0198270 A1 | 8/2009 | McGuckin, Jr. et al. |
| 2009/0264915 A1 | 10/2009 | WasDyke |
| 2009/0299403 A1 | 12/2009 | Chanduszko et al. |
| 2009/0299404 A1 | 12/2009 | Chanduszko et al. |
| 2009/0318951 A1 | 12/2009 | Kashkarov et al. |
| 2010/0030253 A1 | 2/2010 | Harris et al. |
| 2010/0030254 A1 | 2/2010 | Chanduszko et al. |
| 2010/0049239 A1 | 2/2010 | McGuckin, Jr. et al. |
| 2010/0063535 A1 | 3/2010 | Bressler et al. |
| 2010/0076545 A1 | 3/2010 | Kleshinski et al. |
| 2010/0160956 A1 | 6/2010 | Hendriksen et al. |
| 2010/0174310 A1 | 7/2010 | Tessmer |
| 2010/0222772 A1 | 9/2010 | Kleshinski et al. |
| 2010/0256669 A1 | 10/2010 | Harris et al. |
| 2010/0312269 A1 | 12/2010 | McGuckin, Jr. et al. |
| 2010/0318115 A1 | 12/2010 | Chanduszko et al. |
| 2011/0118823 A1 | 5/2011 | Randall et al. |
| 2011/0257677 A1 | 10/2011 | Carr, Jr. et al. |
| 2012/0184985 A1 | 7/2012 | Ravenscroft et al. |

FOREIGN PATENT DOCUMENTS

| | | |
|---|---|---|
| DE | 3633527 A1 | 4/1988 |
| EP | 0145166 A2 | 6/1985 |
| EP | 0188927 A2 | 7/1986 |
| EP | 0712614 A1 | 5/1996 |
| EP | 1042996 A2 | 10/2000 |
| EP | 1092401 A1 | 4/2001 |
| EP | 1336393 A2 | 8/2003 |
| EP | 1475110 A1 | 11/2004 |
| FR | 2567405 A1 | 1/1986 |
| FR | 2718950 A1 | 10/1995 |
| FR | 2781143 A1 | 1/2000 |
| FR | 2791551 A1 | 10/2000 |
| JP | 08257031 | 10/1996 |
| JP | 2002525183 A | 8/2002 |
| JP | 2003521970 A | 7/2003 |
| JP | 2005503199 A | 2/2005 |
| JP | 4851522 B2 | 1/2012 |

| | | |
|---|---|---|
| JP | 5102201 | 10/2012 |
| SV | 07A000025 | 4/1997 |
| WO | 9509567 A1 | 4/1995 |
| WO | 9534339 A1 | 12/1995 |
| WO | 9612448 A1 | 5/1996 |
| WO | 9617634 A2 | 6/1996 |
| WO | 9729794 A1 | 8/1997 |
| WO | 9802203 A1 | 1/1998 |
| WO | 9823322 A1 | 6/1998 |
| WO | 9925252 A1 | 5/1999 |
| WO | 0012011 A1 | 3/2000 |
| WO | 0018467 A1 | 4/2000 |
| WO | 0056390 A1 | 9/2000 |
| WO | 0076422 A1 | 12/2000 |
| WO | 0117457 A1 | 3/2001 |
| WO | 0204060 A1 | 1/2002 |
| WO | 02055125 A2 | 7/2002 |
| WO | 02102436 A2 | 12/2002 |
| WO | 03003927 A1 | 1/2003 |
| WO | 03004074 A3 | 1/2003 |
| WO | 03073961 A1 | 9/2003 |
| WO | 2004012587 A2 | 2/2004 |
| WO | 2004049973 A1 | 6/2004 |
| WO | 2004098459 A1 | 11/2004 |
| WO | 2004098460 A1 | 11/2004 |
| WO | 2005009214 A2 | 2/2005 |
| WO | 2005072645 A1 | 8/2005 |
| WO | 2005102212 A1 | 11/2005 |
| WO | 2005102437 A2 | 11/2005 |
| WO | 2005102439 A2 | 11/2005 |
| WO | 2006036457 A2 | 4/2006 |
| WO | 2006055174 A2 | 5/2006 |
| WO | 2006124405 A2 | 11/2006 |
| WO | 2007021340 A1 | 2/2007 |
| WO | 2007079410 A2 | 7/2007 |
| WO | 2007100619 A2 | 9/2007 |
| WO | 2007106378 A2 | 9/2007 |
| WO | 2007143602 A2 | 12/2007 |
| WO | 2008051294 A2 | 5/2008 |
| WO | 2008076970 A1 | 6/2008 |
| WO | 2008077067 A2 | 6/2008 |
| WO | 2008109131 A2 | 9/2008 |

OTHER PUBLICATIONS

CA 2648325 filed Sep. 23, 1999 Office Action dated Apr. 26, 2011.
Cook "Bird's Nest" Vena Cava Filter, Cook Incorporated, a Cook Group Company, Nov. 1982.
Cook, "Gunther Tulip Vena Cava Mreye.TM. Filter" Sales Brochure (2001).
Cragg et al., "Nonsurgical Placement of Arterial Endoprostheses: A New Technique Using Nitinol Wire" Radiology 147:261-263 (Apr. 1983).
Cynamon et al., "Percutaneous Removal of a Titanium Greenfield Filter" AJR 159:777-778 (Oct. 1992).
Dotter et al., "Transluminal Expandable Nitinol Coil Stent Grafting: Preliminary Report" Radiology 147:259-260 (Apr. 1983).
Engmann and Asch, "Clinical Experience with the Antecubital Simon Nitinol IVC Filter" JVIR 9:774-778 (1998).
Epstein et al., "Experience with the Amplatz Retrievable Vena Cava Filter" Radiology 175:105-110 (1989).
Greenfield et al., "Results of a Multicenter Study of the Modified Hook-Titanium Greenfield Filter" Journal of Vascular Surgery 14:253-257 (Sep. 1991).
Hansen, James, "Metals that Remember", Science 81, vol. 2, No. 5, pp. 44-47, Jun. 1981.
Kim et al., "Insertion of the Simon Nitinol Caval Filter: Value of the Antecubital Vein Approach" AJR 157:521-522 (Sep. 1991).
Kim et al., "Perforation of the Inferior Vena Cava with Aortic and Vetebral Penetration by a Suprarenal Greenfield Filter" Radiology 172:721-723 (1989).
Kim et al., "The Simon Nitinol Filter: Evaluation by MR and Ultrasound" Angiology 43:541-548 (Jul. 1992).
Kim et al., "Vena Cava Filter Placement Via the External Jugular Vein" AJR 155:898-899 (Oct. 1990).
Malden et al., "Transvenous Retreival of Misplaced Stainless Steel Greenfield Filters" JVIR 3:703-708 (1992).

McCowan et al., "Complications of the Nitinol Vena Cava Filter" JVIR 3:401-408 (1992).
Millward, "Temporary and Retrievable Inferior Vena Cava Filters: Current Status" JVIR 9:381-387 (1998).
Nakagawa et al., "A Retrievable Nitinol Vena Cava Filter: Experimental and Initial Clinical Results" JVIR 5:507-512 (1994).
Neuerburg et al., "New Retrievable Percutaneous Vena Cava Filter: Experimental In Vitro and In Vivo Evaluation" Cardiovasc. Intervent. Radiol. 16:224-229 (1993).
Palastrant et al., "Comparative In Vitro Evaluation of the Nitinol Inferior Vena Cava Filter" Radiology 145:351-355 (Nov. 1982).
PCT/US1999/020883 filed Sep. 23, 1999 Search Report dated Jan. 20, 2000.
PCT/US2006/017890 filed May 9, 2006 Preliminary Report on Patentability dated Feb. 12, 2008.
PCT/US2006/017890 filed May 9, 2006 Search Report dated Nov. 2, 2006.
PCT/US2006/017890 filed May 9, 2006 Written Opinion dated Nov. 2, 2006.
Prince et al., "Local Intravascular Effects of the Nitinol Wire Blood Clot Filter" Investigative Radiology 23:294-390 (Apr. 1988).
Prince et al., "The Diameter of the Inferior Vena Cava and Its Implications for the Use of Vena Cava Filters" Radiology 149:687-689 (1983).
Putnam et al., "Placement of Bilateral Simon Nitinol Filters for an Inferior Vena Cava Duplication through a Single Groin Access" JVIR 10:431-433 (1999).
Qian et al., "In Vitro and In Vivo Experimental Evaluation of a New Vena Cava Filter" JVIR 5:513-518 (1994).
Salamipour et al., "Percutaneous Transfemoral Retrieval of a Partially Deployed Simon-Nitinol Filter Misplaced into the Ascending Lumbar Vein" JVIR 7:917-919 (1996).
Sequeira et al., "A Safe Technique for Introduction of the Kimray-Greenfield Filter" Radiology 133:799-800 (Dec. 1979).
Siegel and Robertson, "Percutaneous Tranfemoral Retrieval of a Free-Floating Titanium Greenfield Filter with an Amplatz Goose Neck Snare" JVIR 4:565-568 (1993).
Simon et al., "A Vena Cava Filter Using Thermal Shape Memory Alloy", Radiology, vol. 125, No. 1, Oct. 1977, pp. 89-94.
Simon et al., "Simon Nitinol Inferior Vena Cava Filter: Initial Clinical Experience" Radiology 172:99-103 (1989).
Simon et al., "Transvenous Devices for the Management of Pulmonary Embolism", CardioVascular and Interventional Radiology, 3:308-313, 1980, pp. 112-120.
Simon, "Vena Cava Filters: Prevalent Misconceptions" JVIR 10:1021-1024 (1999).
U.S. Appl. No. 11/150,661, filed Jun. 10, 2005 Final Office Action dated May 27, 2010.
U.S. Appl. No. 11/150,661, filed Jun. 10, 2005 Non-Final Office Action dated Jul. 22, 2011.
U.S. Appl. No. 11/150,661, filed Jun. 10, 2005 Non-Final Office Action dated Nov. 5, 2009.
U.S. Appl. No. 11/334,829, filed Jan. 19, 2006 Non-Final Office Action dated Aug. 18, 2008.
U.S. Appl. No. 11/997,832, filed Aug. 20, 2008 Non-Final Office Action dated Aug. 16, 2010.
U.S. Appl. No. 12/303,545, filed Jun. 29, 2009 Non-Final Office Action dated Jun. 8, 2012.
U.S. Appl. No. 12/336,454, filed Dec. 12, 2008 Non-Final Office Action dated Jan. 24, 2011.
Vesley et al., "Preliminary Investigation of the Irie Inferior Vena Cava Filter" JVIR 7:529-535 (1996).
Zwaan et al., "Clinical Experience with Temporary Vena Cava Filters" JVIR 9:594-601 (1998).
Bovyn, G. et al., "The Tempofilter®: A Multicenter Study of a New Temporary Caval Filter Implantable for up to Six Weeks", Annals of Vascular Surgery, 1997, 11:520-528.
Bracale, G. et al., "Spontaneous Rupture of the Iliac Vein", The Journal of Cardiovascular Surgery, 1999, 40:871-875.
Brasel, K.J. et al., "Cost-Effective Prevention of Pulmonary Embolus in High-Risk Trauma Patients", The Journal of Trauma: Injury, Infection, and Critical Care, Mar. 1997, vol. 42, No. 3, pp. 456-462.

Bravo, S. M. et al., "Percutaneous Venous Interventions", Vascular Medicine, 1998, 3:61-66.

Bridges, G.G. et al., "Expedited Discharge in Trauma Patients Requiring Anticoagulation for Deep Venous Thrombosis Prophylaxis: The LEAP Program", The Journal of Trauma: Injury, Infection and Critical Care, Feb. 2003, vol. 54, No. 2, pp. 232-235.

Brolin, R.E., "Laparoscopic Verses Open Gastric Bypass to Treat Morbid Obesity", Annals of Surgery, Apr. 2004, vol. 239, No. 4, pp. 438-440.

Brountzos, E. N. et al., "A New Optional Vena Cava Filter: Retrieval at 12 Weeks in an Animal Model", Journal of Vascular and Interventional Radiology, Jun. 2003, 14:763-772.

Brown, D. R. et al., "Gadolinium, Carbon Dioxide, and Iodinated Contrast Material for Planning Inferior Vena Cava Filter Placement: a Prospective Trial", Journal of Vascular and Interventional Radiology, Aug. 2003, 14:1017-1022.

Browne, R. J. et al., "Guidewire Entrapment During Greenfield Filter Deployment", Journal of Vascular Surgery, Jan. 1998, 27:174-176.

Bruckheimer, E. et al., "In Vitro Evaluation of a Retrievable Low-Profile Nitinol Vena Cava Filter", Journal of Vascular and Interventional Radiology, Apr. 2003, 14:469-474.

Bucker, A. et al., "Real-Time MR Guidance for Inferior Vena Cava Filter Placement in an Animal Model", Journal of Vascular and Interventional Radiology, Jun. 2001, 12:753-756.

Buerger, P.M. et al., "Risk of Pulmonary Emboli in Patients With Pelvic Fractures", The American Surgeon, Aug. 1993, vol. 59, pp. 505-508.

Burbridge, B. E. et al., "Incorporation of the Gunther Temporary Inferior Vena Cava Filter Into the Caval Wall", Journal of Vascular and Interventional Radiology, Mar.-Apr. 1996, 7:289-290.

Cahn, M. D. et al., "Long Term Follow-up of Greenfield Inferior Vena Cava Filter Placement in Children", Journal of Vascular Surgery, Nov. 2001, 34:820-825.

Cain Jr., J.E. et al., "The Morbidity of Heparin Therapy After Development of Pulmonary Embolus in Patients Undergoing Thoracolumbar or Lumbar Spinal Fusion", Spine, vol. 20, No. 14, 1995, pp. 1600-1603.

Campbell, J. J. et al., "Aortic Pseudoaneurysm From Aortic Penetration With a Bird's Nest Vena Cava Filter", Journal of Vascular Surgery, Sep. 2003, 38:596-599.

Capella, J.F. et al., An Assessment of Vertical Banded Gastroplasty-Roux-en-Y Gastric Bypass for the Treatment of Morbid Obesity.

Carabasi III, R. A. et al., "Complications Encountered With the Use of the Greenfield Filter", The American Journal of Surgery, Aug. 1987, Vo. 154, pp. 163-168.

Carlin, A. M. et al., "Prophylactic and Therapeutic Inferior Vena Cava Filters to Prevent Pulmonary Emboli in Trauma Patients", Archives of Surgery, May 2002, vol. 137, p. 521.

Carman, Teresa L. et al., Outpatient treatment of deep venous thrombosis, Chest; Nov. 1999; 116, 5; Health & Medical Complete, pp. 1492-1493.

Carter, Y. et al., "Deep Venous Thrombosis and ABO Blood Group Are Unrelated in Trauma Patients", The Journal of Trauma: Injury, Infection, and Critical Care, 2002, 52:112-116.

Castaneda, F. et al., "Catheter-Directed Thrombolysis in Deep Venous Thrombosis With Use of Reteplase: Immediate Results and Complications From a Pilot Study", Journal of Vascular and Interventional Radiology, 2002, 13:577-580.

Ceelen, W. et al., "Surgical Treatment of Severe Obesity With a Low-Pressure Adjustable Gastric Band, Experimental Data and Clinical Results in 625 Patients", Annals of Surgery, 2003, 237(1):10-16.

Chanduszko, A., "Determination of Nitinol Transition Temperatures Using a Dynamical Mechanical Analyzer", The International Conference on Shape Memory and Superelastic Technology, 2000 Conference Proceedings, 2001, pp. 375-381.

Chaturvedi, R. R. et al., "Intraoperative Apical Ventricular Septal Defect Closure Using a Modified Rashkind Double Umbrella", Heart, Oct. 1996, vol. 76, No. 4, pp. 367-369.

Chengelis, D.L. et al., "Progression of Superficial Venous Thrombosis to Deep Vein Thrombosis", Journal of Vascular Surgery, 1996, 24:745-749.

Cherian, J. et al., "Recurrent Pulmonary Embolism Despite Inferior Vena Cava Filter Placement in Patients With the Antiphospholipid Syndrome", Journal of Clinical Rheumatology, Feb. 2005, vol. 11, No. 1, pp. 56-58.

Cho, K. J. et al., "Evaluation of a New Percutaneous Stainless Steel Greenfield Filter", Journal of Vascular and Interventional Radiology, Mar.-Apr. 1997, 8:181-187.

Choban, P.S. et al., "The Impact of Obesity on Surgical Outcomes: A Review," Journal of the American College of Surgeons, Dec. 1997, vol. 185, pp. 593-603.

Chung, J.W. et al., "Acute Iliofemoral Deep Vein Thrombosis: Evaluation of Underlying Anatomic Abnormalities by Spiral CT Venography", Journal of Vascular and Interventional Radiology, 2004, 15:249-256.

Clarke, C.S. et al., "Puerperal Ovarian Vein Thrombosis With Extension Into the Inferior Vena Cava", The American Surgeon, Feb. 1999, vol. 65, No. 2, pp. 147-150.

Conners III, M. S et al., "Duplex Scan-Directed Placement of Inferior Vena Cava Filters: A Five-year Institutional Experience", Journal of Vascular Surgery, Feb. 2002, vol. 35, No. 2, pp. 286-291.

Consensus Conference, "Prevention of Venous Thrombosis and Pulmonary Embolism", JAMA, Aug. 8, 1986, vol. 256, No. 6, pp. 744-749.

Cooper, S.G. et al., "Distal Retraction and Inversion of the Simon Nitinol Filter During Surgical Venous Procedures: Report of Two Cases", Journal of Vascular and Interventional Radiology, 1997, 8:433-435.

Cottam, D.R. et al., "Laparoscopic Era of Operations for Morbid Obesity", Archives of Surgery, Apr. 2003, 138(4):367-375.

Couch, G. G. et al., "An In Vitro Comparison of the Hemodynamics of Two Inferior Vena Cava Filters", Journal of Vascular Surgery, Mar. 2000, 31:539-549.

Couch, G. G. et al., "In Vitro Assessment of the Hemodynamic Effects of a Partial Occlusion in a Vena Cava Filter", Journal of Vascular Surgery, Apr. 1997, vol. 25, No. 4, pp. 663-672.

Cragg, A. et al., "A New Percutaneous Vena Cava Filter", American Journal of Roentgenology, Sep. 1983, 141:601-604.

Criado, Enrique, Letters to the Editor, Journal of the American College of Surgeons, Mar. 1996, vol. 182, pp. 279-280.

Critical Care Medicine, vol. 32, No. 12 (Suppl.), pp. A181-A188, 2004.

Crochet, D. et al., "Evaluation of the LGM Vena-Tech Infrarenal Vena Cava Filter in an Ovine Venous Thromboembolism Model", Journal of Vascular Interventional Radiology, Jun. 2001, 12:739-745.

Crochet, D. P. et al., "Long-Term Follow-Up of Vena Tech-LGM Filter: Predictors and Frequency of Caval Occlusion", Journal of Vascular Interventional Radiology, Feb. 1999, 10:137-142.

Crochet, D. P. et al., "Vena Tech-LGM Filter: Long-Term Results of a Prospective Study", Radiology, 1993, 188:857-860.

Cvoro, V. et al., "Inferior Vena Caval Filters or Anticoagulation for Patients With Haemorrhagic Stroke Complicated by Venouse Thromboembolism?", Age and Ageing, Mar. 2002, vol. 32, No. 2, Research Library, pp. 85-86.

Dabbagh, A. et al., "Late Complication of a Greenfield Filter Associating Caudal Migration and Perforation of the Abdominal Aorta by a Ruptured Strut", Journal of Vascular Surgery, Aug. 1995, vol. 22, No. 2, pp. 182-187.

Dake, M.D. et al., "Thrombolytic Therapy in Venous Occlusive Disease", Journal of Vascular and Interventional Radiology, 1995, 6:73S-77S.

Dalman, R. et al., "Cerebrovascular Accident After Greenfield Filter Placement for Paradoxical Embolism", Journal of Vascular Surgery, Mar. 1989, vol. 9, No. 3, pp. 452-454.

Danetz, J. S. et al., "Selective Venography Versus Nonselective Venography Before Vena Cava Filter Placement: Evidence for More, Not Less", Journal of Vascular Surgery, Nov. 2003, vol. 38, No. 5, pp. 928-934.

Danikas, Dimitrios et al., "Use of a Fogarty Catheter to Open an Incompletely Expanded Vena Tech-LGM Vena Cava Filter", Angiology, Apr. 2001, vol. 52, No. 4, pp. 283-286.

Darcy, M.D. et al., "Short-Term Prophylaxis of Pulmonary Embolism by Using a Retrievable Vena Cava Filter", American Journal of Roentgenology, 1986, 147:836-838.

U.S. Appl. No. 12/095,700, filed Jun. 17, 2010 Final Office Action dated Sep. 28, 2012.
U.S. Appl. No. 12/095,991, filed Jul. 31, 2008 Advisory Action dated Sep. 20, 2012.
U.S. Appl. No. 12/095,991, filed Jul. 31, 2008 Notice of Abandonment dated Nov. 23, 2012.
U.S. Appl. No. 12/846,680, filed Jul. 29, 2010 Final Office Action dated Nov. 30, 2012.
"Staff Development Special, Get the Edge on Deep Vein Thrombosis", Nursing Management, Jan. 2004, pp. 21-29.
AbuRahma, A.F. et al., "Endovascular Caval Interruption in Pregnant Patients With Deep Vein Thrombosis of the Lower Extremity", Journal of Vascular Surgery, 2001, 33:375-378.
AbuRahma, A.F. et al., "Management of Deep Vein Thrombosis of the Lower Extremity in Pregnancy: A Challenging Dilemma", The American Surgeon, Feb. 1999, vol. 65, No. 2, pp. 164-167A.
AbuRahma, F. et al., "Etiology of Peripheral Arterial Thromboembolism in Young Patients", The American Journal of Surgery, vol. 176, Aug. 1998, pp. 158-161.
Adams, E. et al., "Retrievable Inferior Vena Cava Filter for Thrombolic Disease in Pregnancy", British Journal of Obstetrics and Gynaecology, Sep. 1998, vol. 105, pp. 1039-1042.
Adye, B. A., "Case Report: Errant Percutaneous Greenfield Filter Placement Into the Retroperitoneum", Journal of Vascular Surgery, Jul. 1990, vol. 12, No. 1.
Ahearn, G.S. et al., "Massive Pulmonary Embolism During Pregnancy Successfully Treated With Recombinant Tissue Plasminogen Activator", Archives of Interal Medicine, Jun. 10, 2002, 162(11):1221-1227.
Aklog, L. et al., "Acute Pulmonary Embolectomy", Circulation, 2002, 105:1416-1419.
Alexander, J. J. et al., "Is the Increasing Use of Prophylactic Percutaneous IVC Filters Justified?", The American Journal of Surgery, Aug. 1994, vol. 168, pp. 102-106.
Allen, T.L. et al., "Retrievable Vena Cava Filters in Trauma Patients for High-Risk Prophylaxis and Prevention of Pulmonary Embolism", The American Journal of Surgery, 2005, 189:656-661.
American Gastroenterological Association Clinical Practice Committee, "Technical Review on Obesity," Sep. 2002 123:883-932.
Anderson, J.T. et al., "Bedside Noninvasive Detection of Acute Pulmonary Embolism in Critically Ill Surgical Patients", Archives of Surgery, Aug. 1999, 134(8):869-875.
Andrews, R. T. et al., "Entrapment of J-Tip Guidewires by Venatech and Stainless-Steel Greenfield Vena Cava Filters During Central Venous Catheter Placement: Percutaneous Management in Four Patients", Correspondence to R.T. Andrews, M.D., The Dotter Interventional Institute, Oregon Heal Sciences University, Portland, OR, pp. 424-427.
Anthone, G.J. et al., The Duodenal Switch Operation for the Treatment of Morbid Obesity, Annals of Surgery, Oct. 2003, 238(4):618-628.
Arcasoy, S.M. et al., "Thrombolytic Therapy of Pulmonary Embolism", Chest, 1999, 115:1695-1707.
Arcelus, J.I. et al, "The Management and Outcome of Acute Venous Thromboembolism: A Prospective Registry Including 4011 Patients", Journal of Vascular Surgery, 2003, 38:916-922.
Arjomand, H. et al., "Right Ventricular Foreign Body: Percutaneous Transvenous Retrieval of a Greenfield Filter From the Right Ventricle", Angiology, 2003, vol. 54, No. 1, pp. 109-113.
Arnold, D.M. et al., "Missed Opportunities for Prevention of Venous Thromboembolism", Chest, 2001, 120:1964-1971.
Ascer, E. et al., "Superior Vena Caval Greenfield Filters: Indications, Techniques, and Results", Journal of Vascular Surgery, Mar. 1996, vol. 23, No. 3.
Asch, M. R., "Initial Experience in Humans With a New Retrievable Inferior Vena Cava Filter", Radiology, 2002, 225:835-844.
Ascher, E. et al., "Lessons Learned From a 6-Year Clinical Experience With Superior Vena Cava Greenfield Filters", Journal of Vascular Surgery, Nov. 2000, 32:881-887.
Ashley, D.W. et al., "Accurate Deployment of Vena Cava Filters: Comparison of Intravascular Ultrasound and Contrast Venography", The Journal of Trauma Injury, Infection, and Critical Care, Jun. 2001, vol. 50, No. 6, pp. 975-981.

Aswad, M. A. et al., "Early Duplex Scan Evaluation of Four Venal Interruption Devices", Journal of Vascular Surgery, 1996, 24:809-818.
Athanasoulis, C.A. et al., "Inferior Venal Caval Filters: Review of a 26-Year Single-Center Clinical Experience", Radiology, 2000, 216:54-66.
Authors' Abstract, "Abstracts of Current Literature", Journal of Vascular and Interventional Radiology, Mar. 2000, vol. 11, No. 3, pp. 401-407.
Authors' Abstract, "Abstracts of Current Literature", Journal of Vascular and Interventional Radiology, Oct. 2003, vol. 14, No. 10, pp. 1351-1357.
Authors' Abstract, "Abstracts of Current Literature," Journal of Vascular and Interventional Radiology, Oct. 2002, 13(10):1062-1068.
Authors' Abstracts, "Abstracts of Current Literature", Journal of Vascular and Interventional Radiology, Apr. 2002, vol. 13, No. 4, pp. 433-440.
Authors' Abstracts, "Abstracts of Current Literature", Journal of Vascular and Interventional Radiology, Apr. 2004, pp. 408-415.
Avery, M. et al., "Reverse Engineering of Nitinol Vena Cava Filters", Material Science 102 Semester Project, Nov. 21, 2000.
Baker, R. J., "Treatment Considerations for Inherited Thrombophilia and Pulmonary Embolus", Archives of Surgery, Feb. 2001, 136,2:237.
Balshi, J. D. et al., "Original Articles Complications of Caval Interruption by Greenfield Filter in Quadriplegics", Journal of Vascular Surgery, Apr. 1989, vol. 9, No. 4.
Barraco, R. D. et al., "Dislodgment of Inferior Vena Cava Filters During Central Line Placement: Case Report", The Journal of Trauma, Injury, Infection and Critical Care, 2000, vol. 48, No. 1, pp. 140-142.
Barreras, J. R. et al., "Recurrent Pulmonary Embolism Despite the Use of a Greenfield Filter", Clinical Nuclear, Dec. 2001, vol. 26, No. 12, pp. 1040-1041.
Barton, A. L. et al., "Caval Filter Placement for Pulmonary Embolism in a Patient With a Deep Vein Thrombosis and Primary Intracerebral Haemorrhage", Age and Ageing, Mar. 2002, 31,2:144-146.
Bass, B.L., "What's New in General Surgery: Gastrointestinal Conditions", The Journal of American College Surgeons, Dec. 2002, vol. 195, No. 6, pp. 835-854.
Becker, D. M. et al., "Inferior Vena Cava Filters", Archives of Internal Medicine, Oct. 1992, vol. 152, pp. 1985-1994.
Bendick, P.J. et al., Serial Duplex Ultrasound Examination for Deep Vein Thrombosis in Patients With Suspected Pulmonary Embolism, Journal of Fascular Surgery, Nov. 1996, vol. 24, No. 5, pp. 732-737.
Benjamin, M. E. et al., Duplex Ultrasound Insertion of Inferior Vena Cava Filters in Multitrauma Patients:, American Journal of Surgery, Aug. 1999, vol. 178, pp. 92-97.
Bessoud, B. et al., Experience at a Single Institution With Endovascular Treatment of Mechanical Complications Caused by Implanted Central Venous Access Devices in Pediatric and Adult Patients, American Journal of Roentgenology, Feb. 2003, 180:527-532.
Bevoni, L., "Management of Adult Obesity", Clinician Reviews, May 2003, 13(5):56-62.
Biertho, L. et al., "Laparoscopic Gastric Bypass Versus Laparoscopic Adjustable Gastric Banding: A Comparative Study of 1,200 Cases", Journal of the American Colloge of Surgeons, Oct. 2003, vol. 197, No. 4, pp. 536-545.
Binkert, C. A. et al., "Inferior Vena Cava Filter Removal After 317-Day Implantation", Journal of Vascular Radiology, Mar. 2005, 16:393-398.
Bjarnason, H. et al., "In Vitro Metal Fatigue Testing of Inferior Vena Cava Filters", Investigative Radiology, 1994, vol. 29, No. 9, pp. 817-821.
Blachar A. et al., "Gastrointestinal Complications of Laparoscopic Roux-en-Y Gastric Bypass Surgery in Patients Who Are Morbidly Obese: Findings on Radiography and CT", American Journal of Roentgenology, Dec. 2002, 179:1437-1442.
Blachar, A. et al., "Gastrointestinal Complications of Laparoscopic Roux-en-Y Gastric Bypass Surgery: Clinical and Imaging Findings", Radiology, 2002, 223:625-632.

Blaszyk, H. et al., "Factor V Leiden and Morbid Obesity in Fatal Postoperative Pulmonary Embolism", Archives of Surgery, Dec. 2000, 135(12):1410-1413.

Blebea J. et al., "Deep Venous Thrombosis After Percutaneous Insertion of Vena Caval Filters", Journal of Vascular Surgery, Nov. 1999, 30:821:829.

Bochenek, K. M. et al., Right Atrial Migration and Percutaneous Retrieval of a Gunther Tulip Inferior Vena Cava Filter, Journal of Vascular Interventional Radiology, Sep. 2003, 14:1207-1209.

Bochicchio, G. V. et al., "Acute Caval Perforation by an Inferior Vena Cava Filter in a Multitrauma Patient: Hemostatic Control With a New Surgical Hemostat", The Journal of Trauma Injury, Infection and Critical Care, 2001, 51:991-993.

Marston, W.A. et al., "Re: Comparison of the AngioJet Rheolytic Catheter to Surgical Thrombectomy for the Treatment of Thrombosed Hemodialysis Grafts", Journal of Vascular and Interventional Radiology (Letters to the Editor), Sep. 2000, vol. 11, No. 8, pp. 1095-1099.

Matteson, B. et al., "Role of Venous Duplex Scanning in Patients With Suspected Pulmonary Embolism", The Journal of Vascular Surgery, 1996, 24:768-773.

Matthews, B. D. et al., "Inferior Vena Cava Filter Placement: Preinsertion Inferior Vena Cava Imaging", The American Surgeon, Aug. 2003, vol. 69, No. 8, pp. 649-653.

Mattos, M.A. et al., "Prevalence and Distribution of Calf Vein Thrombosis in Patients With Symptomatic Deep Venous Thrombosis: A Color-Flow Duplex Study", Journal of Vascular Surgery, 1996, 24:738-744.

Maxwell, R.A. et al., "Routine Prophylactic Vena Cava Filtration is Not Indicated After Acute Spinal Cord Injury", The Journal of Trauma: Injury, Infection, and Critical Care, 2002, 52:902-906.

McCowan, T.C. et al., "Complications of the Nitinol Vena Caval Filter", Journal of Vascular and Interventional Radiology, 1992, 3:401-408.

McMurtry, A.L. et al., "Increased Use of Prophylactic Vena Cava Filters in Trauma Patients Failed to Decrease Overall Incidence of Pulmonary Embolism", Journal of the American College of Surgeons, 1999, 189:314-320.

Meissner, M.H. et al., Venous Thromoembolism in Trauma: A Local Manifestation of Systemic Hypercoagulability?, The Journal of Trauma: Injury, Infection, and Critical Care, Feb. 2003, vol. 54, No. 2, pp. 224-231.

Melinek, J. et al., "Autopsy Findings Following Gastric Bypass Surgery for Morbid Obesity", Arch Path Lab Med, 2002 126:1091-1095.

Mihara, H. et al., "Use of Temporary Vena Cava Filters After Catheter-Directed Fragmentation and Thrombolysis in Patients With Acute Pulmonary Thromboembolism", Japanese Circulartion Journal, Jun. 1998, vol. 62, pp. 462-464.

Miller, A. C., "British Thoracic Society Guidelines for the Management of Suspected Acute Pulmonary Embolism", Thorax, Jun. 2003, 58(6): 470-483.

Miller, Karl E., "Indications for Vena Cava Filters for Recurrent DVT", American Family Physician, Feb. 1, 2003, vol. 67, No. 3, p. 593.

Millward, S., "Temporary IVC Filtration Before Patent Foramen Ovale Closure in a Patient With Paradoxic Embolism", Letter to the Editor, p. 937.

Millward, S.F. et a l., "Preliminary Clinical Experience with the Gunther Temporary Inferior Vena Cava Filter", Journal of Vascular and Interventional Radiology, 1994, 5:863-868.

Millward, S.F. et al., "Gunther Tulip Filter Preliminary Clinical Experience With Retrieval", Journal of Vascular and Interventional Radiology, 2000, 11:75-82.

Millward, S.F. et al., "Gunther Tulip Retrievable Vena Cava Filter: Results From the Registry of the Canadian Interventional Radiology Association", Journal of Vascular and Interventional Radiology, 2001, 12:1053-1058.

Millward, S.F. et al., "LGM (Vena Tech), Vena Caval Filter: Clinical Experience in 64 Patients", Journal of Vascular and Interventional Radiology, Nov. 1991, 2:429-433.

Millward, S.F. et al., "LGM (Vena Tech), Vena Caval Filter: Experience at a Single Institution", Journal of Vascular and Interventional Radiology, Mar.-Apr. 1994, 5:351-356.

Millward, S.F. et al., "Reporting Standards for Inferior Venal Caval Filter Placement and Patient Follow-Up: Supplement for Temporary and Retrievable/Optional Filters", Journal of Vascular and Interventional Radiology, Apr. 2005, 16:441-443.

Millward, S.F., "Gunther Tulip Retrievable Filter Why, When and How?", JACR, Jun. 2001, vol. 52, No. 3, pp. 188-192.

Millward, S.F., "Temporary and Retrievable Inferior Vena Cava Filters Current Status", Journal of Vascular and Interventional Radiology, May-Jun. 1998, vol. 9, No. 3, pp. 381-387.

Mobin-Uddin, K. et al., "Evolution of a New Device for the Prevention of Pulmonary Embolism", The American Journal of Surgery, vol. 168, Oct. 1994, pp. 330-334.

Mohan, C.R. et al., "Comparative Efficacy and Complications of Vena Caval Filters", Journal of Vascular Surgery, 1995, 21:235-236.

Montessuit, M. et al., "Screening for Patent Foramen Ovale and Prevention of Paradoxical Embolus", Ann Fasc Surg, 1997, 11:168-172.

Montgomery, K.D. et al., The Detection and Management of Proximal Deep Venous Thrombosis in Patients With Acute Acetabular Fractures: A Follow-up Report:, Journal of Orthopedic Trauma, Jul. 1997, 1(5):330-336.

Mortele, K. J. et al., "The Swedish Laparoscopic Adjustable Gastric Banding for Morbid Obesity: Radiologic Findings in 218 Patients", American Journal of Roentgenology, 2001, 177:77-84.

Munir, M.A. et al., "An In Situ Technique to Retrieve an Entrapped J-Tip Guidewire From an Inferior Vena Cava Filter", Anesth Analo, 2002, 95:308-309.

Murakami, M. et al., "Deep Venous Thrombosis Prophylaxis in Trauma: Improved Compliance With a Novel Miniaturized Pneumatic Compression Device", Journal of Vascular Surgery, 2003, 38:923-927.

Nakagawa, N. et al., "A Retrievable Nitinol Vena Cava Filter: Experimental and Initial Clinical Results", Journal of Vascular and Interventional Radiology, 1994, 5:507-512.

Nakajima, Osamu et al., "Massive Deep Vein Thrombosis After Cesarean Section Treated With a Temporary Inferior Vena Cava Filter: A Case Report", J Cardioi 2000; 36(5): pp. 337-342.

Napolitano, L. M. et al., "Asymptomatic Deep Venous Thrombosis in the Trauma Patient: Is an Aggressive Screening Protocol Justified?", The Journal of Trauma: Injury, Infection, and Critical Care, 1997, vol. 39, No. 4, pp. 651-659.

Nazario, R. et al., "Treatment of Venous Thromboembolism", Cardiology in Review, 2002, 10(4):249-259.

Neeman, Z. et al., "Metastatic Involvement of a Retrieved Inferior Vena Cava Filter", (Clinical Center) and National Cancer Institute, National Institutes of Health, Bethesda, MD), p. 1585.

Neill, A. M. et al., "Retrievable Inferior Vena Caval Filter for Thromboembolic Disease in Pregnancy", British Journal of Obstetrics and Gynaecology, Dec. 1997, vol. 104, pp. 1416-1418.

Neri, E. et al., "Protected Iliofemoral Venous Thrombectomy in a Pregnant Woman With Pulmonary Embolism and Ischemic Venous Thrombosis", Texas Heart Institute Journal, 2002, vol. 29, No. 2, pp. 130-132.

Neuerburg, J.M. et al., "Percutaneous Retrieval of the Tulip Vena Cava Filter: Feasibility, Short- and long-Term Changes—An Experimental Study in Dogs", Cardiovascular and Interventionai Radiology, 2001, 24:418-423.

Neuerburg, Jorg et al., "Developments in Inferior Vena Cava Filters: A European Viewpoint", Seminars in Interventional Radiology, vol. 11, No. 4, Dec. 1994, pp. 349-357.

Nguyen, N. T. et al., "A Comparison Study of Laparoscopic Versus Open Gastric Bypass for Morbid Obesity", Journal of the American College of Surgeons, Aug. 2000, vol. 191, No. 2, pp. 149-155.

Nguyen, N. T. et al., "Comparison of Pulmonary Function and Postoperative Pain After Laparoscopic Versus Open Gastric Bypass: A Randomized Trial", Journal of Americal College of Surgeons, 2001, 192:469-477.

Norwood, S. H. et al., "A Potentially Expanded Role for Enoxaparin in Preventing Venous Thromboembolism in High Risk Blunt Trauma Patients", Journal of the American College of Surgeons, 2001, 192:161-167.

Nunn, C. R. et al., "Cost-Effective Method for Bedside Insertion of Vena Caval Filters in Trauma Patients," The Journal of Trauma, Nov. 1997, vol. 43, No. 5, pp. 752-758.

Nutting, Charles et al., "Use of a TrapEase Device as a Temporary Caval Filter", Journal of Vascular Interventional Radiology, Aug. 2001, 12:991-993.

O'Brien, P. E. et al., "Laparoscopic Adjustable Gastric Banding in the Treatment of Morbid Obesity", Archives of Surgery, Apr. 2003, 138(4):376-382.

O'Malley, K. F. et al., "Prevention of Pulmonary Embolism After Pelvic Fracture: Rational Use of Inferior Vena Caval Filters", (Cooper Hospital/University Medical Center), Jan. 1996, vol. 40.

O'Sullivan, G. J. et al., "Endovascular Management of Iliac Vein Compression (May-Thurner) Syndrome", Journal of Vascular and Interventional Radiology, 2000, 11:823-836.

Offner, P. J. et al., "The Role of Temporary Inferior Vena Cava Filters in Critically Ill Surgical Patients", Archives of Surgery, Jun. 2003, vol. 138, pp. 591-595.

Olearchyk, A. S., "Insertion of the Inferior Vena Cava Filter Followed by Iliofemoral Venous Thrombectomy for Ischemic Venous Thrombosis", Journal of Vascular Surgery, Apr. 1987, vol. 5, No. 4, pp. 645-647.

Olin, J. W., "Pulmonary Embolism", Reviews in Cardiovascular Medicine, 2002, 3(2):S68-S75.

Oppat, W. F. et al., "Intravascular Ultrasound-Guided Vena Cava Filter Placement", Journal of Endovascular Surgery, 1999, 6:285-287.

Ornstein, D. L. et al., "Cancer, Thrombosis, and Anticoagulants", Current Opinion in Pulmonary Medicine, 2000, 6:301-308.

Henkle, G. et al., "Patterns of Referral for Inferior Vena Caval Filtration: Delays and Their Impact", American Journal of Roentgenology, Oct. 2004, 183:1021-1024.

Hicks, M.E. et al., "Prospective Anatomic Study of the Inferior Vena Cava and Renal Veins: Comparison of Selective Renal Venography With Cavography and Relevance in Filter Placement", Journal of Vascular and Interventional Radiology, 1995, 6:721-729.

Higa, K.D. et al., "Laparoscopic Roux-en-Y Gastric Bypass for Morbid Obesity", Archives of Surgery, Sep. 2000, vol. 135, No. 9, pp. 1029-1034.

Hill, S.L. et al., "Deep Venous Thrombosis in the Trauma Patient", The American Surgeon, Jun. 1994, vol. 60, pp. 405-408.

Hingorani, A. et al., "Upper Extremity Deep Venous Thrombosis and Its Impact on Morbidity and Mortality Rates in a Hospital-Based Population", Journal of Vascular Surgery, Nov. 1997, 26:853-860.

Hirsch, D. R. et al., "Prevalence of Deep Venous Thrombosis Among Patients in Medical Intensive Care", JAMA, Jul. 26, 1995, 274(4):335337.

Hirsch, S. B. et al., Case Reports: Accidental Placement of the Greenfield Filter in the Heart: Report of Two Cases et al., Journal of Vascular Surgery, Dec. 1987, vol. 6, No. 6.

Hoff, W. S. et al., "Early Experience With Retrievable Inferior Vena Cava Filters in High-Risk Trauma Patients", Journal of the American College of Surgeons, Dec. 2004, vol. 199, No. 6, pp. 869-874.

Holtzman, R.B. et al., "Comparison of Carbon Dioxide and Iodinated Contrast for Cavography Prior to Inferior Vena Cava Filter Placement", The American Journal of Surgery, 2003, 185:364-368.

Hosaka, J. et al., "Placement of a Spring Filter During Interventional Treatment of Deep Venous Thrombosis to Reduce the Risk of Pulmonary Embolism", Acta Radiologica, 1999, 40:545-551.

Hughes, G.C. et al., "The Use of a Temporary Vena Caval Interruption Device in High-Risk Trauma Patients Unable to Receive Standard Venous Thromboembolism Prophylaxis", Investigative Radiology, Feb. 1999, vol. 46, No. 2, pp. 246-249.

Hunter, D.W. et al., "Retrieving the Amplatz Retrievable Vena Cava Filter", Cardiovascular and Interventional Radiology, 1987, 10:32-36.

Hyers, T. M. et al., "Antithrombotic Therapy for Venous Thromboembolic Disease", Chest, Jan. 2001, 119(1):176S-193S.

Ihnat, D. M. et al., "Treatment of Patients With Venous Thromboembolism and Malignant Disease: Should Vena Cava Filter Placement Be Routine?", Journal of Vascular Surgery, Nov. 1998, vol. 28, No. 8, pp. 800-807.

Inge, T. H. et al., "Bariatric Surgery for Severely Overweight Adolescents: Concerns and Recommendations", Pediatrics, Jul. 2004, vol. 114, No. 1, pp. 217-223.

Izutani, H. et al., "Migration of an Inferior Vena Cava Filter to the Right Ventricle and Literature Review", Can J Cardiol, Feb. 2004, vol. 20, No. 2, pp. 233-235.

Jackson Slappy, A.L. et al., "Delayed Transcaval Renal Penetration of a Greenfield Filter Presenting as Symptomatic Hydronephrosis", The Journal of Urology, Apr. 2002, vol. 167, pp. 1778-1779.

Jacobs, D. G. et al., "The Role of Vena Caval Filters in the Management of Venous Thromboembolism" The American Surgeon, Aug. 2003, vol. 69, No. 8, pp. 635-642.

Jacobs, D. G. et al., Letters to the Editor, The Journal of Trauma, Dec. 1997, vol. 43, No. 6, pp. 988-989.

Jaeger, H.J. et al., "A Physiologic In Vitro Model of the Inferior Vena Cava With a Computer-Controlled Flow System for Testing of Inferior Vena Cava Filters", Investigative Radiology, Sep. 1997, vol. 32, No. 9, pp. 511-522.

Jain, V. et al., "Preoperative Vena Caval Interruption for Venous Thrombosis Associated With Ovarian Malignancy", Acta Obstetricia Et Gynecologica Scandinavica.

James Kevin V. et al., "Tricuspid Insufficiency After Intracardiac Migration of a Greenfield Filter: Case Report and Review of the Literature", Journal of Vascular Surgery, Sep. 1996, vol. 24, No. 3, pp. 494-498.

Jarrett B.P. et al., Inferior Vena Cava Filters in Malignant Disease, Journal of Vascular Surgery, 2002, 36:704-707.

Joels, C. S. et al., "Complications of Inferior Vena Cava Filters", The American Surgeon, Aug. 2003, vol. 69, No. 8, pp. 654-659.

Johnson, M.S., "Current Strategies for the Diagnosis of Pulmonary Embolus", Journal of Vascular and Interventional Radiology, 2002, 13:13-23.

Johnson, S.P. et al., "Single Institution Prospective Evaluation of the Over-The-Wire Greenfield Vena Caval Filter", Journal of Vascular and Interventional Radiology, 1998, 9:766-773.

Jones, A.L. et al., "Case Report: Use of an IVC Filter in the Management of IVC Thrombosis Occurring as a Complication of Acute Pancreatitis", Clinical Radiology, 1998, 53:462-464.

Joshi, A. et al., "Filter-Related, Thrombotic Occlusion of the Inferior Vena Cava Treated With a Gianturco Stent", Journal of Vascular and Interventional Radiology, 2003, 14:381-385.

JP 2008-543433 filed May 30, 2008 Office Action dated Jan. 11, 2012.

Kaplan, S. et al., "Surgical Management of Renal Cell Carcinoma With Inferior Vena Cava Tumor Thrombus", The American Journal of Surgery, 2002, 183:292-299.

Karmy-Jones, R. et al., "Surgical Management of Cardiac Arrest Caused by Massive Pulmonary Embolism in Trauma Patients", The Journal of Trauma: Injury, Infection, and Critical Care, 2000, vol. 48, No. 3, pp. 519-520.

Kasirajan, K. et al., "Percutaneous AngioJet Thrombectomy in the Management of Extensive Deep Venous Thrombosis", Journal of Vascular and Interventional Radiology, 2001, 12:179-185.

Katsamouris, A.A. et al., "Inferior Vena Cava Filters: In Vitro Comparison of Clot Trapping and Flow Dynamics", Radiology, 1988, 166:361-366.

Kaufman, J.A. et al., "Guide-Wire Entrapment by Inferior Vena Caval Filters: In Vitro Evaluation", Radiology, 1996, 198:71-76.

Kaufman, J.A. et al., "Operator Errors During Percutaneous Placement of Vena Cava Filters", American Journal of Roentgenology, Nov. 1995, 165:1281-1287.

Kaufman, John A., "Re: Metastatic Involvement of a Retrieved Inferior Vena Cava Filter", Journal of Vascular and Interventional Radiology, Jul. 2004, vol. 15, No. 7, pp. 775-776.

Kaw, L.L., Jr. et al., "Use of Vena Cava Filters", Techniques in Orthopaedics, 2004, 19(4):327-336.

Kazmers, A. et al., "Duplex Examination of the Inferior Vena Cava", The American Surgeon, Oct. 2000, vol. 66, pp. 986-989.

Kazmers, A. et al., "Intraoperative Insertion of Greenfield Filters: Lessons Learned in a Personal Series of 152 Cases", The American Surgeon, Oct. 2002, vol. 68, pp. 877-882.

Kazmers, A. et al., "Pulmonary Embolism in Veterans Affairs Medical Centers: Is Vena Cava Interruption Underutilized?", The American Surgeon, Dec. 1999, vol. 65, No. 12, pp. 1171-1175.

Kearon, C. et al., "Management of Anticoagulation Before and After Elective Surgery", The New England Journal of Medicine, May 22, 1997, vol. 336, No. 21, pp. 1506-1511.

Kellum, J. M., "Gastric Banding" Annals of Surgery, Jan. 2003, vol. 237, No. 1, pp. 17-18.

Kelly, J. et al., "Anticoagulation or Inferior Vena Cava Filter Placement for Patients With Primary Intracerebral Hemorrhage Developing Venous Thromboembolism?", Stroke, 2003, 34:2999-3005.

Kercher, K. et al., "Overview of Current Inferior Vena Cava Filters", The American Surgeon, Aug. 2003, vol. 69, pp. 643-648.

Kerlan, R.K., Jr. et al., "Residual Thrombus Within a Retrievable IVC Filter", Journal of Vascular and Interventional Radiology, 16:555-557.

Kerr, A. et al., "Bidirectional Vena Cava Filter Placement", Journal of Vascular Surgery, Oct. 1995, vol. 22, No. 4.

Khansarinia, S. et al., Prophylactic Greenfield Filter Placement in Selected High-Risk Trauma Patients, Journal of Vascular Surgery, 1995, 22:231-236.

Kim, D. et al., "Insertion of the Simon Nitinol Caval Filter: Value of the Antecubital Vein Approach", American Journal of Roentgenology, Sep. 1991, 157:521-522.

Kim, J. et al., "Preliminary Report on the Safety of Heparin for Deep Venous Thrombosis Prophylaxis After Severe Head Injury", The Journal of Trauma: Injury, Infection, and Critical Care, Jul. 2002, vol. 53, No. 1, pp. 38-43.

Kim, V. et al., "Epidemiology of Venous Thromboembolic Disease", Emergency Medicine Clinics of North America, Nov. 2001, vol. 19, No. 4, pp. 839-859.

Ray Jr., C. E. et al., "Complications of Inferior Vena Cava Filters", Abdominal Imaging, 1996, 21:368-374.

Razavi, M. K. et al., "Chronically Occluded Inferior Venae Cavae: Endovascular Treatment", Radiology, 2000, 214:133-138.

RD Heparin Arthroplasty Group, "RD Heparin Compared With Warfarin for Prevention of Venous Thromboembolic Disease Following Total Hip or Knee Arthroplasty", The Journal of Bone and Joint Surgery, Incorporation, Aug. 1994, vol. 76-A, No. 8, pp. 1174-1185.

Reddy, K. et al., "Insertion of an Inferior Venocaval Filter in a Pregnant Woman at Risk for Pulmonary Embolism—A Challenging Management", Departments of Obstetrics and Gynaecology and Radiology, Wexham Park Hospital, Slough, UK, 2003, p. 198.

Reed, Ricahrd A., "The Use of Inferior Vena Cava Filters in Pediatric Patients for Pulmonary Embolus Prophylaxis", Cardiovascular and Interventional Radiology, 1996,19:401-405.

Reekers, J. A. et al., "Evaluation of the Retrievability of the OptEase IVC Filter in an Animal Model", Journal of Vascular and Interventional Radiology, 2004, 15:261-267.

Reekers, Jim A., "Re Current Practice of Temporary Vena Cava Filter Insertion: A Multicenter Registry", Journal of Vascular Interventional Radiology, Nov.-Dec. 2000, pp. 1363-1364.

Ricco, Jean Baptiste et al., "Percutaneous Transvenous Caval Interruption with the LGM Filter", Ann Vasc Surg, 1988,3:242-247.

Ricotta, J. J., "Regarding Recurrent Thromboembolism in Patients With Vena Caval Filters", Journal of Vascular Surgery, 2001, vol. 33, p. 657.

Riedel, M., "Acute Pulmonary Embolism 2: Treatment", Heart, Mar. 2001, 85(3):351-360.

Robinson, Jeffrey D. et al., "In Vitro Evaluation of Caval Filters", Cardiovascular and InterventionalRadiology, 1988, 11 :346-351.

Robrer, M. J. et al., "Extended Indications for Placement of an Inferior Vena Cava Filter", Journal of Vascular Surgery, Jul. 1990, vol. 12, No. 1.

Rodrigues, H. L. et al., "Update of the Management of Venous Thromboembolism [16]", Rev Port Cardiol, 2002, 21(2):183-199.

Rodriguez, J. L. et al., "Early Placement of Prophylactic Vena Caval Filters in Injured Patients at High Risk for Pulmonary Embolism", The Journal of Trauma, Injury, Infection, and Critical Care, 1996, vol. 40, No. 5, pp. 797-804.

Roehm Jr., John O. F. et al., "The Bird's Nest Inferior Vena Cava Filter: Progress Report", Radiology, Sep. 1988,168:745-749.

Roehm Jr., John O. F., "The Bird's Nest Filter: A New Percutaneous Transcatheter Inferior Vena Cava Filter", Journal of Vascular Surgery, Oct. 1984, vol. 1, No. 3.

Rogers, F. B. et al., "Five-Year Follow-Up of Prophylactic Vena Cava Filters in High-Risk Trauma Patients", Archives of Surgery, Apr. 1998, 133:406-411.

Rogers, F. B. et al., "Immediate Pulmonary Embolism After Trauma: Case Report", Journal of Trauma: Injury, Infection, and Critical Care, vol. 48, No. 1, pp. 146-148.

Rogers, F. B. et al., "Practice Management Guidelines for the Prevention of Venous Thromboembolism in Trauma Patients: The East Practice Management Guidelines Work Group", The Journal of Trauma: Injury, Infection, and Critical Care, Jul. 2002, 53:142-164.

Rogers, F. B. et al., "Prophylactic Vena Cava Filter Insertion in Selected High-Risk Orthopaedic Trauma Patients", Journal of Orthopaedic Trauma, 1997, 11(4):267-272.

Rogers, F. B. et al., "Prophylactic Vena Cava Filter Insertion in Severely Injured Trauma Patients: Indications and Preliminary Results", The Journal of Trauma, Oct. 1993, 35(4):637-642.

Rogers, F. B. et al., "Routine Prophylactic Vena Cava Filter Insertion in Severely Injured Trauma Patients Decreases the Incidence of Pulmonary Embolism", Journal of the American College of Surgeons, Jun. 1995 180(6):641-647.

Rogers, F. B., "Venous Thromboembolism in Trauma Patients: A Review", Surgery, Jul. 2001, vol. 130, No. 1, pp. 1-12.

Rohrer, M. J. et al., "Extended Indications for Placement of an Inferior Vena Cava Filter", Journal of Vascular Surgery, Jul. 1989, vol. 10. No. 1, pp. 44-50.

Rose, S. C. et al., "Placement of Inferior Vena Caval Filters in the Intensive Care Unit", Journal of Vascular and Interventional Radiology, 1997, 8:61-64.

Rose, S. C. et al., "Regarding "Bedside Vena Cava Filter Placement Guided With Intravascular Ultrasound"", Journal of Vascular Surgery, Apr. 2002, vol. 35, No. 4.

Rossi, G. et al., "Open to Critique: An Unusual Complication of Vena Cava Filter Placement", Journal of Vascular Surgery, Nov. 1996, vol. 24, No. 5.

Rousseau, Hervé et al., "The 6-F Nitinol TrapEase Inferior Vena Cava Filter: Results of a Prospective Multicenter Trial", J Vasc Interv Radioi, 2001,12:299-304.

Rubin, B. G. et al., "Care of Patients With Deep Venous Thrombosis in an Academic Medical Center: Limitations and Lessons", Journal of Vascular Surgery, 1994, 20:698-704.

Ruiz, A. J. et al., "Heparin, Deep Venous Thrombosis, and Trauma Patients", The American Journal of Surgery, Aug. 1991, 162:159-162.

Ryskamp, R. P. et al., "Utilization of Venous Thromboembolism Prophylaxis in a Medical-Surgical ICU", Chest, Jan. 1998, 113(1):162-164.

S. Raghavan et al., "Migration of Inferior Vena Cava Filter Into Renal Hilum", Nephron, Jun. 2002; 91, 2; Health & Medical Complete; pp. 333-335.

Salamipour, H. et al., "Percutaneous Transfemoral Retrieval of a Partially Deployed Simon-Nitinol Filter Misplaced Into the Ascending Lumbar Vein", Journal of Vascular and Interventional Radiology, 1996, 7:917-919.

Sapala, J. A. et al., "Fatal Pulmonary Embolism After Bariatric Operations for Morbid Obesity: A 24-Year Retrospective Analysis", Obesity Surgery, 2003, 13:819-825.

Sarasin, F. P. et al., "Management and Prevention of Thromboemboli in Patients With Cancer-Related Hypercoagulable", Journal of General Internal Medicine, Sep. 1993, 8:476-485.

Savader, Scott J., Venous Interventional Radiology with Clinical Perspectives, Chapter 28: Inferior Vena Cava Filters, pp. 367-399, Apr. 2000.

Savin, M. A. et al., "Greenfield Filter Fixation in Large Vena Cavae", Journal of Vascular and Interventional Radiology, 1998, 9:75-80.

Savin, Michael A. et al., "Placement of Vena Cava Filters: Factors Affecting Technical Success and Immediate Complications", AJR, Sep. 2002, Vo. 179, pp. 597-602.

Schanzer, H. et al., "Guidewire Entrapment During Deployment of the Over-the-Guidewire Stainless Steel Greenfield Filter: A Device Design-Related Complication", Journal of Vascular Surgery, 2000, 31:607-610.

Schleich, J.-M. et al., "Long-Term Follow-up of Percutaneous Vena Cava Filters: A Prospective Study in 100 Consecutive Patients", Eur J Vasc Endovasc Surg, 2001, vol. 21, pp. 450-457.

Schultz, D. J. et al., "Incidence of Asymptomatic Pulmonary Embolism in Moderately to Severely Injured Trauma Patients", Journal of Trauma: Injury, Infection, and Critical Care, 2004, 56:727-733.

Shackford, S. R. et al., "Venous Thromboembolism in Patients With Major Trauma", The American Journal of Surgery, Apr. 1990, vol. 159, pp. 365-369.

Shaer, J. et al., "An Unusual Cause of Low Back Pain?: A Case Report", Spine, Jun. 15, 1998, 23(12):1349-1350.

Shahmanesh, Maryam et al., "Inferior Vena Cava Filters for HIV Infected Patients With Pulmonary Embolism and Contraindications to Anticoagulation", Sex Transm Inf, 2000, 76:395-397.

Sharafuddin, M. J. et al., "Endovascular Management of Venous Thrombotic and Occlusive Diseases of the Lower Extremities", Journal of Vascular and Interventional Radiology, Apr. 2003, 14:405-423.

Sharpe, R. P. et al., "Incidence and Natural History of Below-Knee Deep Venous Thrombosis in High-Risk Trauma Patients", The Journal of Trauma: Injury, Infection, and Critical Care, Dec. 2002, 53:1048-1052.

Sheikh, M. A. et al., "Images in Vascular Medicine", Vascular Medicine 2001, 6:63-64.

Sheikh, M. A. et al., "Isolated Internal Jugular Vein Thrombosis: Risk Factors and Natural History", Vascular Medicine, 2002, 7:177-179.

Shellock, F. G. et al., "MR Procedures: Biologic Effects, Safety, and Patient Care", Radiology, 2004, 232:635-652.

Siddique, R. M. et al., "Thirty-Day Case-Fatality Rates for Pulmonary Embolism in the Elderly", Archives of Internal Medicine, Nov. 11, 1996, 156:2343-2347.

Tuna, I. C. et al., "Massive Pulmonary Embolus", Texas Heart Institute Journal, 2002, vol. 29, No. 2, pp. 144-145.

Uflacker, R., "Interventional Therapy for Pulmonary Embolism", Journal of Vascular Interventional Radiology, Feb. 2001, 12:147-164.

Urena, R. et al., "Bird's Nest Filter Migration to the Right Atrium", American Journal of Roentgenology, Oct. 2004, 183:1037-1039.

U.S. Appl. No. 09/640,865, filed Aug. 18, 2000 Advisory Action dated Apr. 19, 2007.

U.S. Appl. No. 09/640,865, filed Aug. 18, 2000 Advisory Action dated Mar. 23, 2006.

U.S. Appl. No. 09/640,865, filed Aug. 18, 2000 Final Office Action dated Jan. 16, 2007.

U.S. Appl. No. 09/640,865, filed Aug. 18, 2000 Final Office Action dated Nov. 30, 2005.

U.S. Appl. No. 09/640,865, filed Aug. 18, 2000 Non-Final Office Action dated Apr. 7, 2005.

U.S. Appl. No. 09/640,865, filed Aug. 18, 2000 Non-Final Office Action dated Aug. 8, 2006.

U.S. Appl. No. 09/640,865, filed Aug. 18, 2000 Non-Final Office Action dated Jun. 5, 2003.

U.S. Appl. No. 10/079,155, filed Feb. 20, 2002 Final Office Action dated Jan. 20, 2006.

U.S. Appl. No. 10/079,155, filed Feb. 20, 2002 Non-Final Office Action dated Jul. 13, 2004.

U.S. Appl. No. 10/079,155, filed Feb. 20, 2002 Non-Final Office Action dated Mar. 7, 2007.

U.S. Appl. No. 10/079,155, filed Feb. 20, 2002 Non-Final Office Action dated Nov. 20, 2006.

U.S. Appl. No. 10/079,155, filed Feb. 20, 2002 Non-Final Office Action dated Sep. 11, 2006.

U.S. Appl. No. 11/429,975, filed May 9, 2006 Non-Final Office Action dated Oct. 7, 2010.

U.S. Appl. No. 11/429,975, filed May 9, 2006 Notice of Allowance dated Feb. 18, 2011.

U.S. Appl. No. 11/966,203, filed Dec. 28, 2007 Final Office Action dated Dec. 4, 2009.

U.S. Appl. No. 11/966,203, filed Dec. 28, 2007 Non-Final Office Action dated Aug. 17, 2009.

U.S. Appl. No. 11/997,832, filed Aug. 20, 2008 Non-Final Office Action dated Feb. 23, 2011.

U.S. Appl. No. 12/093,814, filed Jun. 8, 2009 Non-Final Office Action dated Jul. 10, 2012.

U.S. Appl. No. 12/095,700, filed Jun. 17, 2010 Non-Final Office Action dated Jun. 11, 2012.

U.S. Appl. No. 12/095,991, filed Jul. 31, 2008 Final Office Action dated May 4, 2012.

U.S. Appl. No. 12/095,991, filed Jul. 31, 2008 Non-Final Office Action dated Nov. 14, 2011.

U.S. Appl. No. 12/299,300, filed Feb. 24, 2009 Non-Final Office Action dated Apr. 30, 2012.

U.S. Appl. No. 12/299,300, filed Feb. 24, 2009 Notice of Allowance dated Aug. 17, 2012.

U.S. Appl. No. 12/299,304, filed Jun. 16, 2009 Non-Final Office Action dated Jun. 21, 2012.

U.S. Appl. No. 12/727,116, filed Mar. 18, 2010 Non-Final Office Action dated Jul. 18, 2012.

U.S. Appl. No. 12/846,680, filed Jul. 29, 2010 Non-Final Office Action dated May 7, 2012.

U.S. Appl. No. 13/009,727, filed Jan. 19, 2011 Notice of Allowance dated Apr. 27, 2012.

U.S. Appl. No. 13/170,054, filed Jun. 27, 2011 Non-Final Office Action dated Jul. 2, 2012.

Valji, K., "Evolving Strategies for Thrombolytic Therapy of Peripheral Vascular Occlusion", Journal of Vascular and Interventional Radiology, 2000, 11:411-420.

Van Ha, Thuong G. et al., "Removal of Gunther Tulip Vena Cava Filter Through Femoral Vein Approach", Journal of Vascular and Interventional Radiology, 2005, 16:391-394.

Van Natta, Timothy L. et al., "Elective Bedside Surgery in Critically Injured Patients is Safe and Cost-Effective", American Surgery, May 1998, 227(5):618-626.

Vedantham, S. et al., "Endovascular Recanalization of the Thrombosed Filter-Bearing Inferior Vena Cava", Journal of Vascular and Interventional Radiology, 2003, 14:893-903.

Vedantham, S. et al., "Lower Extremity Venous Thrombolysis With Adjunctive Mechanical Thrombectomy", Journal of Vascular and Interventional Radiology, 2002, 13:1001-1008.

Vedantham, S. et al., "Pharmacomechanical Thrombolysis and Early Stent Placement for Iliofemoral Deep Vein Thrombosis", Journal of Vascular and Interventional Radiology, 2004, 15:565-574.

Velmahos, G. C. et al., "Inability of an Aggressive Policy of Thromboprophylaxis to Prevent Deep Venous Thrombosis (DVT) in Critically Injured Patients: Are Current Methods of DVT Prophylaxis Insufficient?", Journal of the American College of Surgeons, 1998, 187:529-533.

Velmahos, G. C. et al., "Prevention of Venous Thromboembolism After Injury: An Evidence-Based Report—Part 1: Analysis of Risk Factors and Evaluation of the Role of Vena Caval Filters", The Journal of Trauma: Injury, Infection, and Critical Care, Jul. 2000, 49:132-139.

Velmahos, G. C. et al., "Prevention of Venous Thromboembolism After Injury: An Evidence-Based Report—Part II: Analysis of Risk Factors and Evaluation of the Role of Vena Caval Filters", The Journal of Trauma: Injury, Infection, and Critical Care, Jul. 2000, 49:140-144.

Velmahos, G. C. et al., "Spiral Computed Tomography for the Diagnosis of Pulmonary Embolism in Critically Ill Surgical Patients", Archives of Surgery, May 2001, 136(5):505-511.

Venbrux, Anthony C., "Protection Against Pulmonary Embolism: Permanent and Temporary Caval Filters" Department of Radiology—CVDL, The Johns Hopkins Medical Institutions, Baltimore MD, 7 pages.

Vesely, T. M. et al., "Preliminary Investigation of the Irie Inferior Vena Caval Filter", Journal of Vascular and Interventional Radiology, 1996, 7:529-535.

Vorwerk, D. et al., "Use of a Temporary Caval Filter to Assist Percutaneous Iliocaval Thrombectomy: Experimental Results", Journal of Vascular and Interventional Radiology, Sep.-Oct. 1995, 6(5):737-740.

Vos, Louwerens D. et al., "The Gunther Temporary Inferior Vena Cava Filter for Short-Term Protection Against Pulmonary Embolism", Cardiovascular and Interventional Radiology, 1997, 20:91-97.
Vrachliotis, T. G. et al., "Percutaneous Management of Extensive Clot Trapped in a Temporary Vena Cava Filter", Journal of Endovascular Therapy, 2003, 10:1001-1005.
Wakefield, T. W., Treatment Options for Venous Thrombosis, Journal of Vascular Surgery, Mar. 2000, 31(3):613-620.
Wallace, M. J. et al., "Inferior Vena Caval Stent Filter", AJR, Dec. 1986, 147:1247-1250.
Wallace, M. J., "Transatrial Stent Placement for Treatment of Inferior Vena Cava Obstruction Secondary to Extension of Intracardiac Tumor Thrombus From Hepatocellular Carcinoma", Journal of Vascular Interventional Radiology, 2003, 14:1339-1343.
Wang, W. Y. et al., "Use of a Nitinol Gooseneck Snare to Open an Incompletely Expanded Over-the-Wire Stainless Steel Greenfield Filter", American Journal of Roentgenology, Feb. 1999, 172:499-500.
Watanabe, N. et al., "Images in Cardiology: Large Thrombus Entrapped in a Patent Foramen Ovale of the Atrial Septum, Which Apparently "Disappeared" Without Embolic Events", Heart, Nov. 2002, 88(5):474.
Watanabe, S. et al., "Superior Vena Caval Placement of a Temporary Filter: A Case Report", Vascular Surgery, Jan./Feb. 2001, vol. 35, Issue 1.
Watanabe, Shun-ichi et al., "Clinical Experience With Temporary Vena Cava Filters", Vascular Surgery, vol. 35, No. 4, 2001, pp. 285-291.
Weeks, S. M. et al., "Primary Gianturco Stent Placement for Inferior Vena Cava Abnormalities Following Liver Transplantation", Journal of Vascular and Interventional Radiology, Feb. 2000, 11:177-187.
Welch, H. J. et al., "Duplex Assessment of Venous Reflux and Chronic Venous Insufficiency: The Significance of Deep Venous Reflux", Journal of Vascular Surgery, 1996, 24:755-762.
Wellons, E. D. et al., "Bedside Intravascular Ultrasound-Guided Vena Cava Filter Placement", Journal of Vascular Surgery, 2003, 38:455-458.
Wells, J. L. et al., "Diagnosing Pulmonary Embolism: A Medical Masquerader", Clinician Reviews, 2001, 11(2):66-79.
Westling, A. et al., "Incidence of Deep Venous Thrombosis in Patients Undergoing Obesity Surgery", World Journal of Surgery, 2002, 26:470-473.
White, R. H. et al., "A Population-Based Study of the Effectiveness of Inferior Vena Cava Filter Use Among Patients With Venous Thromboembolism", Archives of Internal Medicine, Jul. 10, 2000, 160(13):2033-2041.
Whitehill, T. A., "Current Vena Cava Filter Devices and Results", Seminars in Vascular Surgery, Sep. 2000, 13(3):204-212.
Wholey, M. et al., "Technique for Retrieval of a Guidewire Lodged in a Vena Cava Filter", Vascular and Endovascular Surgery, 2002, 36(5):385-387.
Wiles, C. E., Letters to Editor, Journal of Trauma, Aug. 1999, 47(2):438.
Wilson, J. T. et al., "Prophylactic Vena Cava Filter Insertion in Patients With Traumatic Spinal Cord Injury: Preliminary Results", Neurosurgery, 1994, 35:234-239.
Winchell, R. J. et al., "Risk Factors Associated With Pulmonary Embolism Despite Routine Prophylaxis: Implications for Improved Protection", The Journal of Trauma, 1994, 37(4):600-606.
Wittenberg, G. et al., "Long-Term Results of Vena Cava Filters: Experiences With the LGM and the Titanium Greenfield Devices", Cardiovascular and Interventional Radiology, 1998, 21:225-229.
Wittich, G. R. et al., "Anchoring a Migrating Inferior Vena Cava Stent With Use of a T-Fastener", Journal of Vascular and Interventional Radiology, 2001, 12:994-996.
Wojcik, R. et al., "Long-Term Follow-Up of Trauma Patients With a Vena Caval Filter", The Journal of Trauma: Injury, Infection, and Critical Care, Nov. 2000, 49(5):839-843.
Wojtowycz, M. M. et al., "The Bird's Nest Inferior Vena Caval Filter: Review of a Single-Center Experience", Journal of Vascular and Interventional Radiology, 1997, 8:171-179.
Woodward, E. B. et al., "Delayed Retroperitoneal Arterial Hemorrhage After Inferior Vena Cava (IVC) Filter Insertion: Case Report and Literature Review of Caval Perforations by IVC Filters", Annals of Vascular Surgery, 2002, 16:193-196.
Xian, Z. Y. et al., "Multiple Emboli and Filter Function: An In Vitro Comparison of Three Vena Cava Filters", Journal of Vascular and Interventional Radiology, 1995, 6:887-893.
Xu, X. Y. et al., "Flow Studies in Canine Artery Bifurcations Using a Numerical Simulation Method", Journal of Biochemical Engineering, Nov. 1992, 114:504-511.
Yagi, A. et al., "Pulmonary Thromboembolism Evaluating the Indication and Effect of a Vena Caval Filter With Indium-111-Platelet Scintigraphy", Circulation Journal, Jun. 2004, 68:599-601.
Yavuz, Kivilcim et al., "Retrievable of a Malpositioned Vena Cava Filter With Embolic Protection With Use of a Second Filter", Journal of Vascular Interventional Radiology, 2005, 16:531-534.
Yonezawa, K. et al., "Effectiveness of an Inferior Vena Cava Filter as a Preventive Measure Against Pulmonary Thromboembolism After Abdominal Surgery", Surgery Today, 1999, 29:821-824.
Yucel, E. Kent, "Pulmonary MR Angiography: Is It Ready Now?", Radiology, 1999, 210:301-303.
Zamora, C. A. et al., "Prophylactic Stenting of the Inferior Vena Cava Before Transcatheter Embolization of Renal Cell Carcinomas: An Alternative to Filter Placement", Journal of Endovascular Therapy, 2004, 11:84-88.
Zanchetta, M. et al., "A New Permanent and Retrievable Vena Cava Filter: Its Removal After Five Months", Italian Heart Journal, Sep. 2001, 2(9):715-716.
Zeni, P. T. et al., "Use of Rheolytic Thrombectomy in Treatment of Acute Massive Pulmonary Embolism", Journal of Vascular and Interventional Radiology, 2003, 14:1511-1515.
Zinzindohoue, F. et al., "Laparoscopic Gastric Banding: A Minimally Invasive Surgical Treatment for Morbid Obesity—Prospective Study of 500 Consecutive Patients", Annals of Surgery, 2003, 237(1):1-9.
Simon Nitinol Filter SNF/SL Filter Sets, C. R. Bard, Inc. PK5014851 Rev. 01 Sep. 2002.
Simon Nitinol Filter, Nitinol Medical Technologies, Inc., p. 290.
Simon, M. et al., "Comparative Evaluation of Clinically Available Inferior Vena Cava Filters With an In Vitro Physiologic Simulation of the Vena Cava", Radiology, 1993, 189:769-774.
Simon, M. et al., "Paddle-Wheel CT Display of Pulmonary Arteries and Other Lung Structures: A New Imaging Approach", American Journal of Roentgenology, Jul. 2001, pp. 195-198.
Simon, M., "Vena Cava Filters: Prevalent Misconceptions", Journal of Vascular and Interventional Radiology, 1999, 10:1021-1024.
Simon, Morris et al., "Simon Nitinol Inferior Vena Cava Filter: Initial Clinical Experience", Radiology, vol. 172, No. 1, DO 99-103, Jul. 1989.
Simon,M. et al., "A Vena Cava Filter Using Thermal Shape Memory Alloy", Radiology, Oct. 1977, 125:89-94.
Sing, R. F. et al., "Bedside Carbon Dioxide (CO2) Preinsertion Cavagram for Inferior Vena Cava Filter Placement: Case Report", Journal of Trauma, Dec. 1999, 47(6):1140-1142.
Sing, R. F. et al., "Bedside Carbon Dioxide Cavagrams for Inferior Vena Cava Filters: Preliminary Results", Journal of Vascular Surgery, 2000, 32:144-147.
Sing, R. F. et al., "Bedside Insertion of Inferior Vena Cava Filters in the Intensive Care Unit", Journal of American College of Surgeons, May 2001, 192(5):570-575.
Sing, R. F. et al., "Bedside Insertion of Inferior Vena Cava Filters in the Intensive Care Unit", Journal of Trauma, Dec. 1999, 47(6):1104-1109.
Sing, R. F. et al., "Bedside Insertion of the Inferior Vena Cava Filter in the Intensive Care Unit", The American Surgeon, Aug. 2003, 69:660-662.
Sing, R. F. et al., "Guidewire Incidents With Inferior Vena Cava Filters", JAOA, Apr. 2001, 101(4):231-233.
Sing, R. F. et al., "Preliminary Results of Bedside Inferior Vena Cava Filter Placement", Chest, Jul. 1998, 114(1):315.
Sing, R. F. et al., "Regarding Bedside Vena Cava Filter Placement Guided With Intravascular Ultrasound", Journal of Vascular Surgery, May 2002, vol. 25, No. 5.

Sing, Ronald F., "Safety and Accuracy of Bedside Carbon Dioxide Cavography for Insertion of Inferior Vena Cava Filters in the Intensive Care Unit", American Coiiege of Surgeons, Feb. 2, 2001, vol. 192, pp. 168-171.
Smith, T. P. et al., "Acute Pulmonary Thromboembolism—Comparison of the Diagnostic Capabilities of Convention Film—Screen and Digital Angiography", Chest, 2002, 122:968-972.
Smith, T. P., "Pulmonary embolism: What's Wrong With This Diagnosis", American Journal of Roentgenology, Jun. 2000, 174:1489-1498.
Spain, D. A. et al., "Venous Thromboembolism in the High-Risk Trauma Patient: Do Risks Justify Aggressive Screening and Prophylaxis?", The Journal of Trauma: Injury, Infection, and Critical Care, 1997, vol. 42, No. 3, pp. 463-469.
Spence, Liam D. et al., "Acute Upper Extremity Deep Venous Thrombosis, Safety and Effectiveness of Superior Vena Caval Filters", Radiology, Jan. 1999, vol. 210, DO 53-58.
Stavropoulos, S. W. et al., "In Vitro Study of Guide Wire Entrapment in Currently Available Inferior Vena Cava Filters", Journal of Vascular and Interventional Radiology, 2003, 14:905-910.
Stecker, M. S. et al., "Evaluation of a Spiral Nitinol Temporary Inferior Vena Caval Filter", Academic Radiology, 2001, 8:484-493.
Stein, P. D. et al., "Deep Venous Thrombosis in a General Hospital", Chest, 2002, 122:960-962.
Stein, P. D., "Opinions Regarding the Diagnosis and Management of Venous Thromboembolic Disease", Chest, Feb. 1998, vol. 113, No. 2, pp. 499-504.
Still, J. et al., "Experience With the Insertion of Vena Caval Filters in Acutely Burned Patients", The American Surgeon, Mar. 2000, vol. 66, No. 3, pp. 277-279.
Stoneham G. W. et al., "Temporary Inferior Vena Cava Filters: In Vitro Comparison With Permanent IVC Filters", Journal of Vascular and Interventional Radiology, Sep.-Oct. 1995, vol. 6, pp. 731-736.
Stosslein, F. et al., "A Rare Complication With an Antheor Vena Cava Filter", Cardiovascular and Interventional Radiology, 1998, 21:165-167.
Stover, M. D. et al., "Prospective Comparison of Contrast-Enhanced Computed Tomography Versus Magnetic Resonance Venography in the Detection of Occult Deep Pelvic Vein Thrombosis in Patients With Pelvic and Acetabular Fractures", Journal of Orthopaedic Trauma, 2002, 16(9):613-621.
Streib, E. W. et al., "Complications of Vascular Access Procedures in Patients With Vena Cava Filters", The Journal of Trauma: Injury Infection, and Critical Care, Sep. 2000, vol. 49, No. 3, pp. 553-558.
Streiff, Michael B., "Vena Caval Filters: A Comprehensive Review", Blood, Jun. 15, 2000, vol. 95, No. 12, pp. 3669-3677.
Sue, L. P. et al., "Iliofemoral Venous Injuries: An Indication for Prophylactic Caval Filter Placement", The Journal of Trauma: Injury, Infection, and Critical Care, 1995, vol. 39, No. 4, pp. 693-695.
Sugerman, H. J. et al., "Risks and Benefits of Gastric Bypass in Morbidity Obese Patients With Severe Venous Stasis Disease", Annals of Surgery, 2001, vol. 234, No. 1, pp. 41-46.
Sultan, S. et al., "Operative and Endovascular Management of Extracranial Vertebral Artery Aneurysm in Ehlers-Danlos Syndrome: A Clinical Dilemma", Vascular and Endovascular Surgery, 2002, 36(5):389-392.
Taheri, S. A. et al., "Case Report: A Complication of the Greenfield Filter: Fracture and Distal Migration of Two Struts—A Case Report", Journal of Vascular Surgery, Jul. 1992, vol. 16, No. 1, pp. 96-99.
Tai, N. R. M. et al., "Modern Management of Pulmonary Embolism", British Journal of Surgery, 1999, 86:853-868.
Tardy, B. et al, "Older People Included in a Venous Thrombo-Embolism Clinical Trial: A Patients' Viewpoint", Age and Ageing, 2003, 32:149-153.
Tay, Kiang-Hiong et ai, "Repeated Gunther Tulip Inferior Vena Cava Filter Repositioning to Prolong Implantation Time", J Vasc Interv Radioi, May 2002, 13:509-512.
Taylor, Frank C. et al., "Vena Tech Vena Cava Filter: Experience and Early Follow-up", Journal of Vascular Interventional Radiology, Nov. 1991, 2:435-440.
Teitelbaum, G. P. et al., Low-Artifact Intravascular Devices: MR Imaging Evaluation, Radiology, Sep. 1988, 168:713-719.

Terhaar, Olaf Alfons et al., "Extended Interval for Retrieval of Gunther Tulip Filters", J Vascinterv Radioi, Nov. 2004,15:1257-1262.
The Simon Nitinol Filter, Instructions for Use, Nitnol Medical Technologies, Inc.
Thery, C. et al., "Use of a New Removable Vena Cava Filter in Order to Prevent Pulmonary Embolism in Patients Submitted to Thrombolysis", European Heart Journal, 1990, vol. 11,334-341.
Thomas, J. H. et al., "Vena Caval Occlusion After Bird's Nest Filter Placement", American Journal of Surgery, Dec. 1998, vol. 176, pp. 598-600.
Thomas, L. A. et al., "Use of Greenfield Filters in Pregnant Women at Risk for Pulmonary Embolism", Southern Medical Journal, Feb. 1997, vol. 90, Issue 2.
Tillie-Leblond, I. et al., "Risk of Pulmonary Embolism After a Negative Spiral CT Angiogram in Patients With Pulmonary Disease: 1-Year Clinical Follow-Up Study", Radiology, 2002, 223:461-467.
Tola, J. C. et al., "Bedside Placement of Inferior Vena Cava Filters in the Intensive Care Unit", The American Surgeon, Sep. 1999, vol. 65, No. 9, pp. 833-838.
Tovey, C. et al., "Diagnosis, Investigation, and Management of Deep Vein Thrombosis", British Medical Journal, May 31, 2003, vol. 326, i7400, p. 1180(5), 9 pages.
Trerotola, S. O. et al., "Mechanical Thrombolysis of Venous Thrombosis in an Animal Model With Use of Temporary Caval Filtration", Journal of Vascular and Interventional Radiology, Sep. 2001, 12:1075-1085.
Trerotola, S. O. et al., "Preclinical in Vivo Testing of the Arrow-Trerotola Percutaneous Thrombolytic Device for Venous Thrombosis", Journal of Vascular and Interventional Radiology, 2001, 12:95-103.
Trujillo-Santos,J. et al., "Bed Rest or Ambulation in the Initial Treatment of Patients With Acute Deep Vein Thrombosis or Pulmonary Embolism", Chest, 2005, 127:1631-1636.
Ortega, M. et al., "Efficacy of Anticoagulation Post-Inferior Vena Caval Filter Placement", American Surgeon, May 1998, vol. 64, Issue 5, pp. 419-423.
Ortiz-Saracho, J. et al., "An Unusual Cause of Pulmonary Artery Thrombosis", Chest, 1998, 114:309-310.
Owings, J. T. et al., "Timing of the Occurrence of Pulmonary Embolism in Trauma Patients", Archives of Surgery, Aug. 1997, 132(8):862-867.
Padberg, F. T. et al, "Hemodynamic and Clinical Improvement After Superficial Vein Ablation in Primary Combined Venous Insufficiency With Ulceration", Journal of Vascular Surgery, 1996, 24:711-718.
Pais, S. O. et al., "Percutaneous Insertion of the Greenfield Inferior Vena Cava Filter: Experience With Ninety-Six Patients", Journal of Vascular Surgery, Oct. 1988, vol. 8. No. 4.
Palestrant, Aubrey M. et al., "Comparative In Vitro Evaluation of the NitinolInferior Vena Cava Filter", Radiology, Nov. 1982,145:351-355.
Participants in the Vena Caval Filter Consensus Conference, "Recommended Reporting Standards for Vena Caval Filter Placement and Patient Follow-Up", Journal of Vascular and Interventional Radiology, 2003, 14:S427-S432.
Participants in the Vena Caval Filter Consensus Conference, "Recommended Reporting Standards for Vena Caval Filter Placement and Patient Follow-Up", Journal of Vascular Surgery, 1999, 30:573-579.
Partsch, H. et al., "Frequency of Pulmonary Embolism in Patients Who Have Iliofemoral Deep Vein Thrombosis and Are Treated With Once- or Twice-Daily Low-Molecular Weight Heparin", Journal of Vascular Surgery, 1996, 24:774-782.
Passman, M. A. et al., "Pulmonary Embolism is Associated With the Combination of Isolated Calf Vein Thrombosis and Respiratory Symptoms", Journal of Vascular Surgery, 1997, 25:39-45.
Patterson, R. B. et al., "Case Reports: Repositioning of Partially Dislodged Greenfield Filters From the Right Atrium by Use of a Tip Deflection Wire", Journal of Vascular Surgery, Jul. 1990, vol. 12, No. 1, pp. 70-72.
Patton, J. H. Jr., et al., "Prophylactic Greenfield Filters: Acute Complications and Long-Term Follow-Up", The Journal of Trauma: Injury, Infection, and Critical Care, 1996, vol. 41, No. 2, pp. 231-237.

Pavcnik, Dusan et al., "Retrievable IVC Square Stent Filter: Experimental Study", Cardiovascular Interventional Radiology, 1999,22:239-245.

PCT/US03/05385 filed Feb. 20, 2003 International Search Report dated Jun. 17, 2003.

PCT/US07/09215 filed Apr. 16, 2007 International Preliminary Report on Patentability dated Sep. 23, 2008.

PCT/US07/09215 filed Apr. 16, 2007 International Search Report dated Sep. 23, 2008.

PCT/US2006/017889 filed May 9, 2006 International Preliminary Report on Patentability dated Jul. 14, 2009.

PCT/US2006/017889 filed May 9, 2006 International Search Report dated Jul. 1, 2009.

PCT/US2006/017889 filed May 9, 2006 Written Opinion dated Jul. 1, 2009.

PCT/US2006/044826 filed Nov. 17, 2006 International Preliminary Report on Patentability and Written Opinion dated Apr. 10, 2008.

PCT/US2006/044826 filed Nov. 17, 2006 International Search Report dated Apr. 10, 2008.

PCT/US2006/045738 filed Nov. 11, 2006 Search Report dated Oct. 9, 2007.

PCT/US2006/045738 filed Nov. 11, 2006 Written Opinion dated Oct. 9, 2007.

PCT/US2007/009186 filed Apr. 16, 2007 International Preliminary Report on Patentability and Written Opinion dated Nov. 4, 2008 and Sep. 29, 2008.

PCT/US2007/009186 filed Apr. 16, 2007 International Search Report dated Sep. 29, 2008.

PCT/US2010/043787 filed Jul. 29, 2010 Search Report dated Dec. 3, 2010.

PCT/US2010/043787 filed Jul. 29, 2010 Written Opinion dated Dec. 3, 2010.

Peck, K. E. et al., "Postlaparoscopic Traumatic Inferior Vena Caval Thrombosis", Heart & Lung, Jul./Aug. 1998, vol. 27, No. 4, pp. 279-281.

Pelage, J. et al., "Re: Leiomyoma Recurrence After Uterine Artery Embolization", Journal of Vascular and Interventional Radiology, Jul. 2004, vol. 15, No. 7, pp. 773-776.

Peskin, Gerald R. (ed.), Papers of the Western Surgical Association, "Directed Parathyroidectomy—Feasibility and Performance in 100 Consecutive Patients With Primary Hyperparathyroidism", Archives of Surgery, Jun. 2003, vol. 138, p. 581.

Peterson, D. A. et al., "Computed Tomographic Venography is Specific But Not Sensitive for Diagnosis of Acute Lower-Extremity Deep Venous Thrombosis in Patients With Suspected Pulmonary Embolus", Journal of Vascular Surgery, 2001, 34:798-804.

Podnos, Y. D. et al., "Complications After Laparoscopic Gastric Bypass", Archives of Surgery, Sep. 2003, 138:957-961.

Poletti, P.A. et al., "Long-Term Results of the Simon Nitinol Inferior Vena Cava Filter", Eur. Radiol., 1998, vol. 8, pp. 289-294.

Ponchon, M. et al., "Temporary Vena Caval Filtration Preliminary Clinical Experience With Removable Vena Caval Filters", Acta Clinica Belgica, 1999, vol. 54, pp. 223-228.

Porcellini, Massimo et al., "Intracardiac Migration of Nitinol TrapEase™ Vena Cava Filter and Paradoxical Embolism", European Journal of Cardio-Thoracic Surgery, vol. 22, 2002, pp. 460-461.

Porter, J. M. et al., "Reporting Standards in Venous Disease: An Update", Journal of Vascular Surgery, 1995, 21:635-645.

Poster: Clinical Science: Pulmonary Disease or Dysfunctional/Mechanical Ventilation/Weaning (Adult), Critical Care Medicine, vol. 32, No. 12 (Suppl.), pp. A111-A120, 2004.

Prince, M. R. et al., "The Diameter of the Inferior Vena Cava and Its Implications for the Use of Vena Caval Filters", Radiology, 1983, 149:687-689.

Proctor, M. C. et al., "Assessment of Apparent Vena Caval Penetration by the Greenfield Filter", Journal of Endovascualr Surgery, 1998, 5:251-258.

Proctor, M. C., "Indications for Filter Placement", Seminars in Vascular Surgery, Sep. 2000, vol. 13, No. 3, pp. 194-198.

Putterman, Daniel et al., "Aortic Pseudoaneurysm After Penetration by a Simon Nitinol Inferior Vena Cava Filter", J Vasc Interv Radiol, 2005, 16:535-538.

Qanadli, S. D. et al., "Pulmonary Embolism Detection: Prospective Evaluation of Dual-Section Helical CT Versus Selective Pulmonary Arteriography in 157 Patients", Radiology, 2000, 217:447-455.

Quality Improvement Guidelines for Percutaneous Inferior Vena Cava Filter Placement for the Prevention of Pulmonary Embolism (European Standards adopted and Modified by CIRSE in Cooperation With SCVIR Standards of Practice Committee), http:www.cirse.org/vena_cava_filter_crise.htm, retrieved May 17, 2002, 11 pages.

Questions and Answers: Vena Caval filters and anticoagulants, JAMA; Oct. 20, 1993; 270, 15; pp. 1867-1868.

Quirke, T. E. et al., "Inferior Vena Caval Filter Use in U.S. Trauma Centers" A Practitioner Survey, The Journal of Trauma: Injury, Infection, and Critical Care, 1997, vol. 43, No. 2, pp. 333-337.

Rabkin, D. J. et al., "Nitinol Properties Affecting Uses in Interventional Radiology", Journal of Vascular and Interventional Radiology, 2000, 11:343-350.

Radke, P. W. et al., "Thrombosis in Behcet's Disease: Report of a Case Followed by a Systematic Review Using the Methodology of Evidence-Based Medicine", Journal of Thrombosis and Thrombolysis, Apr. 2001, 11(2):137-141.

Rajan, Dheeraj K. et al., "Retrieval of the Bard Recovery Filter from the Superior Vena Cava," JVIR, Letters to the Editor, vol. 15, No. 10, Oct. 2004, pp. 1169-1171.

Raju, N. L. et al., "Case 37: Juxtacaval Fat Collection—Mimic of Lipoma in the Subdiaphragmatic Inferior Vena Cava", Radiology, 2001, 220:471-474.

Rascona, D. A. et al., "Pulmonary Embolism—Treatment vs Nontreatment", Chest, Jun. 1999, vol. 115, No. 6, p. 1755.

Kimmerly, W. S. et al., "Graduate Surgical Trainee Attitudes Toward Postoperative Thromboprophylaxis", Southern Medical Journal, Aug. 1999, vol. 92, No. 9, pp. 790-794.

King, J.N. et al., "Vena Cava Filters", The Western Journal of Medicine, Mar. 1992, vol. 156, No. 3, pp. 295-296.

Kinney, T. B. et al., "Regarding Limb Asymmetry in Titanium Greenfield Filters: Clinically Significant?", Journal of Vascular Surgery, Jun. 1998, vol. 27, No. 6.

Kinney, T.B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

Kinney, T.B. et al., "Fatal Paradoxic Embolism Occurring During IVC Filter Insertion in a Patient With Chronic Pulmonary Thromboembolic Disease", Journal of Vascular and Interventional Radiology, 2001, 12:770-772.

Kinney, T.B., "Translumbar High Inferior Vena Cava Access Placement in Patients With Thrombosed Inferior Vena Cava Filters", Journal of Vascular and Interventional Radiology, 2003, 14:1563-1567.

Kinney, T.B., "Update on Inferior Vena Cava Filters", Journal of Vascular and Interventional Radiology, 2003, 14:425-440.

Kistner, R. L., Definitive Diagnosis and Definitive Treatment in Chronic Venous Disease: A Concept Whose Time Has Come:, Journal of Vascular Surgery, Nov. 1996, vol. 24, No. 5, pp. 703-710.

Knudson, M. M. et al., "Prevention of Venous Thromboembolism in Trauma Patients", The Journal of Trauma, Sep. 1994, vol. 37, No. 3, pp. 480-487.

Knudson, M. M. et al., "Thromboembolism After Trauma—An Analysis of 1602 Episodes From the American College of Surgeons National Trauma Data Bank" Annals of Surgery, Sep. 2004, vol. 240, No. 3, pp. 490-498.

Knudson, M. M. et al., Thromboembolism Following Multiple Trauma, The Journal of Trauma, Jan. 1992, vol. 32, No. 1, pp. 2-11.

Knudson, M. M. et al., "Venous Thromboembolism After Trauma", Current Opinion in Critical Care, 2004, 10:539-548.

Koga, F. et al., "Deep Vein Thrombosis During Chemotherapy in a Patient With Advanced Testicular Cancer: Successful Percutaneous Thrombectomy Under Temporary Placement of Retrievable Inferior Vena Cava Filter", International Journal of Uroloty, 2001, 8:90-93.

Konya, A. et al., "New Embolization Coil Containing a Nitinol Wire Core: Preliminary in Vitro and in Vivo Experiences", Journal of Vascular and Interventional Radiology, 2001, 12:869-877.

Kozak, T.K.W. et al., "Massive Pulmonary Thromboembolism After Manipulation of an Unstable Pelvic Fracture: A Case Report and Review of the Literature", The Journal of Trauma: Injury, Infection, and Critical Care, 1995, vol. 38, pp. 366-367.

Kraimps, J. et al., "Optical Central Trapping (OPCETRA) Vena Caval Filter: Results of Experimental Studies", Journal of Vascular and Interventional Radiolory, 1992, 3:697-701.

Kreutzer J.et al., "Healing Response to the Clamshell Device for Closure of Intracardiac Defects in Humans", Catheterization and Cardiocardiovascular Interventions, 2001, vol. 54.

Kronemyer, B., Temporary Filter Traps Pulmonary Emboly, Orthopedics Today, p. 34.

Kudsk, K. A. et al., "Silent Deep Vein Thrombosis in Immobilized Multiple Trauma Patients", The American Journal of Surgery, Dec. 1989, vol. 158, pp. 515-519.

Kupferschmid, J.P. et al., "Case Report: Small-Bowel Obstruction From an Extruded Greenfield Filter Strut: An Unusual Late Complication", Journal of Vascular Surgery, Jul. 1992, vol. 16, No. 1, pp. 113-115.

Kurgan, A. et al., "Case Reports: Penetration of the Wall of an Abdominal Aortic Aneurysm by a Greenfield Filter Prong: A Late Complication", Journal of Vascular Surgery, Aug. 1993, vol. 18, No. 2, pp. 303-306.

Kuszyk, B. et al., "Subcutaneously Tethered Temporary Filter: Pathologic Effects in Swine", Journal of Vascular and Interventional Radiology, Nov.-Dec. 1995, Vo. 6, No. 6, pp. 895-902.

Kyrle, P. A. et al., Deep Vein Thrombosis, The Lancet, Mar. 26-Apr. 1, 2005, 365(9465):1163-1174.

Langan III, E. M. et al., "Prophylactic Inferior Vena Cava Filters in Trauma Patients at High Risk: Follow-Up Examination and Risk/ Benefit Assessment", Journal of Vascular Surgery, 1999, 30:484-490.

Leach, T. A. et al., "Surgical Prophylaxis for Pulmonary Embolism", The American Surgeon, Apr. 1994, vol. 60, No. 4, pp. 292-295.

Leask, R.L. et al., "Hemodynamic Effects of Clot Entrapment in the TrapEase Inferior Vena Cava Filter", Journal of Vascular and Interventional Radiology, 2004, 15:485-490.

Leask, R.L. et al., "In Vitro Hemodynamic Evaluation of a Simon Nitinol Vena Cava Filter: Possible Explanation of IVC Occlusion", Journal of Vascular and Interventional Radiology, 2001, 12:613-618.

Lemmon, G.W. et al., "Incomplete Caval Protection Following Suprarenal Caval Filter Placement", Angiology The Journal of Vascular Diseases, Feb. 2000, vol. 51, No. 2, pp. 155-159.

Leoni, C. J. et al., "Classifying Complications of Interventional Procedures: A Survey of Practicing Radiologists", Journal of Vascular and Interventional Radiology, 2001, 12:55-59.

Letai, A., "Cancer, Coagulation, and Anticoagulation", The Oncologist, 1999, 4:443-449.

Lewis-Carey, M. B. et al., "Temporary IVC Filtration Before Patent Foramen Ovale Closure in a Patient With Paradoxic Embolism", Journal of Vascular and Interventional Radiology, 2002, 13:1275-1278.

Lidagoster, M. I. et al., Superior Vena Cava Occlusion After Filter Insertion, Journal of Vascular Surgery, Jul. 1994, vol. 20, No. 1.

Lin, J. et al., "Factors Associated With Recurrent Venous Thromboembolism in Patients With Malignant Disease", Journal of Vascular Surgery, 2003, 37:976-983.

Lin, M. et al., "Successful Retrieval of Infected Gunther Tulip IVC Filter", Journal of Vascular and Interventional Radiology, 2000, 11:1341-1343.

Lin, P. H. et al., "The Regained Referral Ground and Clinical Practice of Vena Cava Filter Placement in Vascular Surgery", The American Surgeon, Oct. 2002, vol. 68, No. 10, pp. 865-870.

Linsenmaier U. et al, "Indications, Management, and Complications of Temporary Inferior Vena Cava Filters", Cardiovascular and Interventional Radiology, 1998, 21:464-469.

Lipman, J.C., "Removal of Vena Caval Filter at 224 Days", Southern Medical Journal, May 2005, vol. 98, No. 5, pp. 556-558.

Loehr, S.P. et al., "Retrieval of Entrapped Guide Wire in an IVC Filter Facilitated With Use of a Myocardial Biopsy Forceps and Snare Device", Journal of Vascular and Interventional Radiology (Letter to Editor), Sep. 2001, vol. 12, No. 9, pp. 1116-1118.

Lopez-Beret, P. et al., "Systematic Study of Occult Pulmonary Thromboembolism in Patients With Deep Venous Thrombosis", Journal of Vascular Surgery, 2001, 33:515-521.

Lorch, H. et al., "Current Practice of Temporary Vena Cava Filter Insertion: A Multicenter Registry", Journal of Vascular and Interventional Radiology, 2001, 11:83-88.

Lorch, H. et al., "In Vitro Studies of Temporary Vena Cava Filters", Cardiovascular and Interventional Radiology, 1998, 21:146-150.

Lorch, H. et al., "Temporary Vena Cava Filters and Ultrahigh Streptokinase Thrombolysis Therapy: A Clinical Study", Cardiovascular Interventional Radiology, 2000, 23:273-278.

Lujan, J. A. et al., "Laparoscopic Versus Open Gastric Bypass in the Treatment of Morbid Obesity", Annals of Surgery, Apr. 2004, vol. 239, No. 4, pp. 433-437.

Lund, G. et al., "A New Vena Caval Filter for Percutaneous Placement and Retrieval Experimental Study", Radiology, 1984, 152:369-372.

Lund, G. et al., "Retrievable Vena Caval Filter Percutaneously Introduced", Radiology, 1985, vol. 155, p. 831.

Luo, X. Y. et al., "Non-Newtonian Flow Patterns Associated With an Arterial Stenosis", Journal of Biomechanical Engineering, Nov. 1992, 114:512-514.

MacDonald, K. G. Jr., "Overview of the Epidemiology of Obesity and the Early History of Procedures to Remedy Morbid Obesity", Archives of Surgery, Apr. 2003, 138(4):357-360.

Machado, L.G. et al., "Medical Applications of Shape Memory Alloys", Brazilian Journal of Medical and Biological Research, 2003, 36:683-691.

Magnant, J.G. et al., "Current Use of Inferior Vena Cava Filters", Journal of Vascular Surgery, Nov. 1992, vol. 16, No. 5, pp. 701-706.

Manke, C. et al., "MR Imaging-Guided Stent Placement in Iliac Arterial Stenoses: A Feasibility Study", Radioilogy, 2001, 219:527-534.

Girard, T. D. et al., "Prophylactic Vena Cava Filters for Trauma Patients: A Systematic Review of the Literature", Thrombosis Research, 2003, 112:261-267.

Goldberg, M.E., "Entrapment of an Exchange Wire by an Inferior Vena Caval Filter: A Technique for Removal", Anesth Analg., Apr. 2003, 96:4, 1235-1236.

Goldhaber, S.Z. et al., "Acute Pulmonary Embolism: Part II Risk Stratification, Treatment, and Prevention", Circulation, 2003, 108:2834-2838.

Goldhaber, S.Z., "A Free-Floating Approach to Filters", Archives of Internal Medicine, Feb. 10, 1997, vol. 157, No. 3, pp. 264-265.

Goldhaber, S.Z., "Venous Thromboembolism in the Intensive Care Unit: The Last Frontier for Pro . . . ", Chest, Jan. 1998, 113(1):5-7.

Goldman, H.B. et al., "Ureteral Injury Secondary to an Inferior Vena Caval Filter", The Journal of Urology, Nov. 1996, vol. 156, No. 5, p. 1763.

Golueke, P.J. et al., "Interruption of the Vena Cava by Means of the Greenfield Filter: Expanding the Indications", Surgery, Jan. 1988, vol. 103, No. 1, pp. 111-117.

Gonze, M.D. et al., "Orally Administered Heparin for Preventing Deep Venous Thrombosis", American Journal of Surgery, Aug. 1998, vol. 176, pp. 176-178.

Goodman, L.R. et al., "Subsequent Pulmonary Embolism: Risk After a Negative Helical CT Pulmonary Angiogram—Prospective Comparison With Scintigraphy", Radiology, 2000, 215:535-542.

Gosin, J. S., "Efficacy of Prophylactic Vena Cava Filters in High-Risk Trauma Patients", Annals of Vascular Surgery, 1997, 11:100-105.

Gottlieb, R.H., "Randomized Prospective Study Comparing Routine Versus Selective Use of Sonography of the Complete Calf in Patients With Suspected Deep Venous Thrombosis", American Journal of Roentgenology, Jan. 2003, 180:241-245.

Grandas, O.H. et al., "Deep Venous Thrombosis in the Pediatric Trauma Population: An Unusual Event: Report of Three Cases", The American Surgeon, Mar. 2000, vol. 66, pp. 273-276.

Grassi, C.L. et al., "Quality Improvement Guidelines for Percutaneous Permanent Inferior Vena Cava Filter Placement for the Prevention of Pulmonary Embolism", Journal of Vascular and Interventional Radiology, Sep. 2003, 14:S271-S275.

Grassi, C.L. et al., "Vena Caval Occlusion After Simon Nitinol Filter Placement: Identification With MR Imaging in Patients With Malignancy", Journal of Vascular and Interventional Radiology, 1992, 3(3):535-539.

Greene, F.L. et al., Letters to the Editor, The Journal of Trauma: Injury, Infection, and Critical Care, May 2005, vol. 5 8, No. 5, pp. 1091-1092.

Greenfield, L. J. et al., "Clinical Experience With the Kim-Ray Greenfield Vena Caval Filter", Ann Surg, Jun. 1977, vol. 185, No. 6, pp. 692-698.

Greenfield, L. J. et al., "Experimental Embolic Capture by Asymmetric Greenfield Filters", Journal of Vascular Surgery, Sep. 1992, vol. 16, No. 3, pp. 436-444.

Greenfield, L.J. et al., "Filter Complications and Their Management", Seminars in Vascular Surgery, vol. 13, No. 3, Sep. 2000, pp. 213-216.

Greenfield, L.J. et al., "Free-Floating Thrombus and Pulmonary Embolism/Reply", Archives of Internal Medicine, Dec. 8-22, 1997, pp. 2661-2662.

Greenfield, L.J. et al., "Limb Asymmetry in Titanium Greenfield Filters: Clinically Significant?", Journal of Vascular Surgery, 1997, 26:770-775.

Greenfield, L.J. et al., "Prophylactic Vena Caval Filters in Trauma: The Rest of the Story", Journal of Vascular Surgery, 2000, 32:490-497.

Greenfield, L.J. et al., "Recommended Reporting Standards for Vena Caval Filter Placement and Patient Follow-Up", Journal of Vascular and Interventional Radiology, 1999, 10:1013-1019.

Greenfield, L.J. et al., "The Percutaneous Greenfield Filter: Outcomes and Practice Patterns", Journal of Vascular Surgery, 2000, 32:888-893.

Greenfield, L.J. et al., "Twenty-Year Clinical Experience With the Greenfield Filter", Cardiovascular Surgery, Apr. 1995, vol. 3, No. 2, pp. 199-205.

Greenfield, L.J., "Cost vs Value in Vena Caval Filters", Chest, Jul. 1998, vol. 114, No. 1, pp. 9-10.

Greenfield, L.J., "Current Indications for and Results of Greenfield Filter Placement", Journal Vascular Surgery, May 1984, vol. 1, No. 3, pp. 502-504.

Greenfield, L.J., "Does Cervical Spinal Cord Injury Induce Higher Incidence of Complications After Prophylactic Greenfield Filter Usage?", Journal of Vascular and Interventional Radiology, Jul.-Aug. 1997, pp. 719-720.

Greenfield, L.J., "Recurrent Thromboembolism in Patients With Vena Cava Filters", Journal of Vascular Surgery, 2001, 33:510-514.

Greenfield, L.J., "Staging of Fixation and Retrievability of Greenfield Filters", Journal of Vascular Surgery, Nov. 1994, vol. 20, No. 5, pp. 744-750.

Greenfield, Lazar J. et al., "A New Intracaval Filter Permitting Continued Flow and Resolution of Emboli", Surgery, Apr. 1973, vol. 73, No. 4, pp. 599-606.

Greenfield, Lazar J. et al., "Suprarenal Filter Placement", Journal of Vascular Surgery, Sep. 1998, 28:432-438.

Greenfield, Lazar J. et al., "Vena Caval Filter Use in Patients With Sepsis", Archives of Surgery, Nov. 2003, vol. 138, No. 11, Health & Medical Complete, pp. 1245-1248.

Greenfield, Lazar J. et al ., "Extended Evaluation of the Titanium Greenfield Vena Caval Filter", Journal of Vascular Surgery, Nov. 1994, vol. 20, No. 3, pp. 458-465.

Günther, Rolf W. et al., "Vena Caval Filter to Prevent Pulmonary Embolism: Experimental Study", Radiology, Aug. 1985,156:315-320.

Haage, Patrick et al., "Prototype Percutaneous Thrombolytic Device: Preclinical Testing in Subacute Inferior Vena Caval Thrombosis in a Pig Model", Radiology, Jul. 2001,220:135-141.

Hagspiel, K.D. et al., "Inferior Vena Cava Filters: An Update", Applied Radiology, Nov. 1998, pp. 20-34.

Hagspiel, K.L. et al., "Difficult Retrieval of a Recovery IVC Filter", Journal of Vascular and Interventional Radiology (Letters to the Editor), Jun. 2004, vol. 15, No. 6, pp. 645-650.

Hainaux, B. et al., "Intragastric Band Erosion After Laparoscopic Adjustable Gastric Banding for Morbid Obesity: Imaging Characteristics of an Underreported Complication", American Journal of Roentgenology, Jan. 2005, 184:109-112.

Hak, D.J., "Prevention of Venous Thromboembolism in Trauma and Long Bone Fractures", Current Opinion in Pulmonary Medicine, 2001, 7:338-343.

Hammer, Frank D. et al., "In Vitro Evaluation of Vena Cava Filters", Journal of Vascular and Interventionai Radiology, Nov.-Dec. 1994, 5:869-876.

Hammond, F.M. et al., "Venous Thromboembolism in the Patient With Acute Traumatic Brain Injury: Screening, Diagnosis, Prophylaxis, and Treatment Issues", Journal of Head Trauma Rehabilitation, Feb. 1998, vol. 13, No. 1, pp. 36-48.

Hardhammar, P.A. et al., "Reduction in Thrombotic Events With Heparin-Coated Palmaz-Schatz Stents in Normal Porcine Coronary Arteries", Circulation, Feb. 1, 1996, vol. 93, No. 3, pp. 423-430.

Harold, K.L. et al., "Laparoscopic Approach to Open Gastric Bypass", The American Journal of Surgery, 2002, 184:61-62.

Harries, S.R., "Long-Term Follow-Up of the Antheor Inferior Vena Cava Filter", Clinical Radiology, 1998, 53:350-352.

Harris, E.J. Jr. et al., "Phlegmasia Complicating Prophylactic Percutaneous Inferior Vena Caval Interruption: A Word of Caution", Journal of Vascular Surgery, 1995, vol. 22, No. 5, pp. 606-611.

Hastings, G.S. et al., "Repositioning the 12-F Over-the-Wire Greenfield Filter", Journal of Vascular and Interventional Radiology, 2000, 11:1207-1210.

Hawkins, S.P. et al., "The Simon Nitinol Inferior Vena Cava Filter: Preliminary Experience in the UK", Clinical Radiology, 1992, 46:378-380.

Headrick, J.R. et al., "The Role of Ultrasonography and Inferior Vena Cava Filter Placement in High-Risk Trauma Patients", American Surgeon, Jan. 1997, vol. 63, Issue 1.

Helfet, D., Magnetic Resonance Venography to Evaluate Deep Venous Thrombosis in Patients With Pelvic and Acetabular Trauma, The Journal of Trauma: Injury, Infection, and Critical Care, Jul. 2001, p. 178.

Heng, J.T. et al., "Occlusion of Persistent Left Superior Vena Cava to Unroofed Coronary Sinus Using Vena Cava Filter and Coils", Hears, Jun. 1997, vol. 77, No. 6, pp. 579-580.

Dardik, Alan et al., "Vena Cava Filter Ensnarement and Delayed Migration: An Unusual Series of Cases", Journal of Vascular Surgery, Nov. 1997, vol. 26, No. 5.

David, W. et al., "Pulmonary Embolus After Vena Cava Filter Placement", The American Surgeon, Apr. 1999, vol. 65, pp. 341-346.

Davidson, B.L., "DVT Treatment in 2000: State of the Art", Orthopedics, Jun. 2000, 23(6):pp. S651-s654.

Davison, Brian D. et al., "TrapEase Inferior Vena Cava Filter Placed Via the Basilic Arm Vein: A New Antecubital Access", J Vasc Interv Radioi, Jan. 2002, 13:107-109.

de Godoy, José Maria Pereira et al., "In-Vitro Evaluation of a New Inferior Vena Cava Filter—The Stent-Filter", Vascular and Endovascular Surgery, Nov. 3, 2004, vol. 38, pp. 225-228.

de Gregorio, M.A. "Inferior Vena Cava Filter Update", Arch Bronconeumol, 2004, vol. 40, No. 5, pp. 193-195.

De Gregorio, M.A. et al., "Animal Experience in the Gunther Tulip Retrievable Inferior Vena Cava Filter", Cardiovascular and Interventional Radiology, Nov. 2001, 24:413-417.

De Gregorio, M.A. et al., "Mechanical and Enzymatic Thrombolysis for Massive Pulmonary Embolism", Journal of Vascular and Interventional Radiology, 2002, 13:163-169.

de Gregorio, Miguel Angel et al., "The Gunther Tulip Retrievable Filter: Prolonged Temporary Filtration by Repositioning Within the Inferior Vena Cava", J Vasc Interv Radioi, Oct. 2003, 14:1259-1265.

De Gregorio, Miguel Angel et al., "Retrievability of Uncoated Versus Paclitaxel-Coated Gunther-Tulip IVC Filters in an Animal Model", J Vasc Interv Radioi, Jul. 2004,15:719-726.

Debing, E. et al., "Popliteal Venous Aneurysm With Pulmonary Embolism", Journal of Cardiovascular Surgery, Oct. 1998, vol. 39, No. 5, pp. 569-572.

Decousus, H. et al., "A Clinical Trial of Vena Caval Filters in the Prevention of Pulmonary Embolism in Patients With Proximal Deep-Vein Thrombosis", The New England Journal of Medicine, Feb. 12, 1998, vol. 338, No. 7, pp. 409-415.

DeMaria, E.J. et al., "Results of 281 Consecutive Total Laparoscopic Roux-en-Y Gastric Bypasses to Treat Morbid Obesity", Annals of Surgery, 2002, vol. 235, No. 5 pp. 640-647.

Dennis, J.W. et al., "Efficacy of Deep Venous Thrombosis Prophylaxis in Trauma Patients and Identification of High-Risk Groups", The Journal of Trauma, 1993, vol. 35, No. 1, pp. 132-137.

Denny, D.F. Jr., "Errant Percutaneous Greenfield Filter Placement Into the Retroperitoneum" Journal of Vascular Surgery Jun. 1991, vol. 13, No. 6.

Dewald, C.L. et al., Vena Cavography With CO2 Versus With Iodinated Contrast Material for Inferior Vena Cava Filter Placement: A Prospective Evaluation, Radiology, 2000, 216:752-757.

Dibie, A. et al., "In Vivo Evaluation of a Retrievable Vena Cava Filter—The Dibie-Musset Filter: Experimental Results", Cardiovascular and Interventional Radiology, 1998, 21:151-157.

Dick, A. et al., "Declotting of Embolized Temporary Vena Cava Filter by Ultrasound and the Angiojet: Comparative Experimental In Vitro Studies", Investigative Radiology, Feb. 1998, vol. 33(2), pp. 91-97.

Doherty, C., "Special Problems of Massive Obesity", Primary Care Physician's Resource Center, file://D:\Special%20Problems%20of%20Massive%20Obesity.htm, retrieved Jul. 26, 2005.

Duperier, T. et al., "Acute Complications Associated With Greenfield Filter Insertion i High-Risk Trauma Patients", The Journal of Trauma: Injury, Infection, and Critical Care, Mar. 2003, vol. 54, No. 3, pp. 545-549.

Ebaugh, James L. et al., "Bedside Vena Cava Filter Placement Guided With Intravascular Ultrasound", Journal of Vascular Surgery, Jul. 2001,34:21-26.

Edlow, J.A., "Emergency Department Management of Pulmonary Embolism", Emergency Medicine Clinics of North America, Nov. 2001, vol. 19, No. 4, pp. 995-1011.

Egermayer, P., "Follow-Up for Death or Recurrence Is Not a Reliable Way of Assessing the Accuracy of Diagnostic Tests for Thromboembolic Disease", Chest 1997, 111:1410-1413.

Ekim, N. et al., "Pulmonary Thromboembolism With Massive Vaginal Bleeding Due to Thrombolytic Therapy", Respirology, 2003, 8:246-248.

EP 99951426 European Search Report dated Mar. 18, 2003.

Fava, M. et al., "Massive Pulmonary Embolism: Percutaneous Mechanical Thrombectomy During Cardiopulmonary Resuscitation", Journal of Vascular and Intervention Radiology, 2005, 16:119-123.

Fava, M. et al., "Massive Pulmonary Embolism: Treatment With the Hydrolyser Thrombectomy Catheter", Journal of Vascular and Intervention Radiology, 2000, 11:1159-1164.

Feezor, R.J. et al., "Duodenal Perforation With an Inferior Vena Cava Filter: An Unusual Cause of Abdominal Pain", Journal of Vascular Surgery, 2002, pp. 1-3.

Fernandez, A.Z. Jr. et al., "Multivariate Analysis of Risk Factors for Death Following Gastric Bypass for Treatment of Morbid Obesity", Annals of Surgery, May 2004, vol. 239, No. 5, pp. 698-703.

Ferral, H., "Regarding Lessons Learned From a 6-Year Clinical Experience With Superior Vena Cava Greenfield Filters", Journal of Vascular Surgery, Apr. 2001, vol. 33, No. 4.

Ferraro, F. et al., "Thromboembolism in Pregnancy: A New Temporary Caval Filter", Miverva Anestesiologica, 2001, vol. 67, No. 5, pp. 381-385.

Ferris, E.J. et al., "Percutaneous Inferior Vena Caval Filters: Follow-Up of Seven Designs in 320 Patients", Radiology 1993, 188:851-856.

Fink, S. et al., "Pulmonary Embolism and Malpractice Claims", Southern Medical Journal, Dec. 1998, vol. 91, No. 12, pp. 1149-1152.

Fobbe, Franz et al., "Gunther Vena Caval Filter: Results of Long-Term Follow-Up", AJR, Nov. 1988,151:1031-1034.

Foley, M. et al., "Pulmonary Embolism After Hip or Knee Replacement: Postoperative Changes on Pulmonary Scintigrams in Asymptomatic Patients", Radiology, 1989, 172:481-485.

Fraser, J.D. et al., "Deep Venous Thrombosis: Recent Advances and Optimal Investigation With US", Radiology, 1999, 211:9-24.

Frezza, E.E. et al., "Entrapment of a Swan Ganz Catheter in an IVC Filter Requiring Caval Exploration", Journal of Cardiovascular Surgery, 1999, 40:905-908.

Friedell, M.L. et al., "Case Report: Migration of a Greenfield Filter to the Pulmonary Artery: Case Report", Journal of Vascular Surgery, Jun. 1986, vol. 3, No. 6, pp. 929-931.

Friedland, M. et al., "Vena Cava Duplex Imaging Before Caval Interruption", Journal of Vascular Surgery, Oct. 1995, vol. 24, No. 4, pp. 608-613.

Gabelmann, A. et al., "Percutaneous Retrieval of Lost of Misplaced Intravascular Objects", American Journal of Radiology, Jun. 2001, 176:1509-1513.

Galus, Maria et al., "Indications for inferior vena cava filters," Internal Medicine, Aug. 11, 1997; 157, 15; Health and Medical Complete, pp. 1770-1771.

Gamblin, T.C. et al., "A Prospective Evaluation of a Bedside Technique for Placement of Inferior Vena Cava Filters: Accuracy and Limitations of Intravascular Ultrasound", The American Surgeon, May 2003, vol. 69, pp. 382-386.

Garcia, N. D., "Is Bilateral Ultrasound Scanning of the Legs Necessary for Patients With Unilateral Symptoms of Deep Vein Thrombosis", Journal of Vascular Surgery, 2001, 34:792-797.

Gayer, G. et al., "Congenital Anomalies of the Inferior Vena Cava Revealed on CT in Patients With Deep Vein Thrombosis", American Journal of Roentgenology, Mar. 2003, vol. 180, pp. 729-732.

Geerts, W.H., "A Prospective Study of Venous Thromboembolism After Major Trauma", Dec. 15, 1994, vol. 331, No. 24, pp. 1601-1606.

Gelbfish, G. A. et al., "Intracardiac and Intrapulmonary Greenfield Filters: A Long-Term Follow-Up", Journal of Vascular Surgery, Nov. 1991, vol. 14, No. 5, pp. 614-617.

Gelfand, E.V. et al., "Venous Thromboembolism Guidebook, Fourth Edition", Critical Pathways in Cardiology, Dec. 2003, vol. 2, No. 4, pp. 247-265.

Georgopoulos, S.E. et al., "Paradoxical Embolism", Journal of Cardiovascular Surgery, 2001, 42:675-677.

Ginsberg, M.S. et al., "Clinical Usefulness of Imaging Performed After CT Angiography That Was Negative for Pulmonary Embolus in a High-Risk Oncologic Population", American Journal of Roentgenology, Nov. 2002, 179:1205-1208.

Girard, P. et al., Medical Literature and Vena Cava Filters, Chest, 2002, 122:963-967.

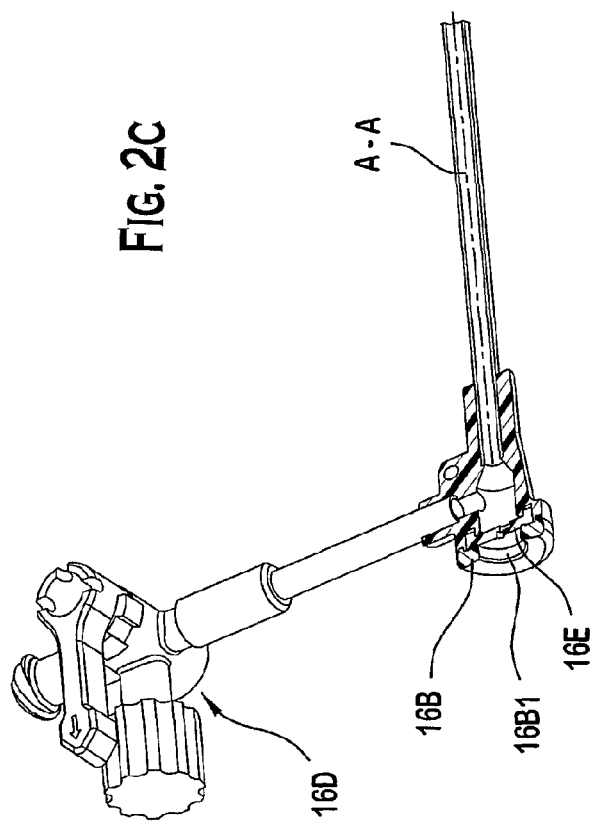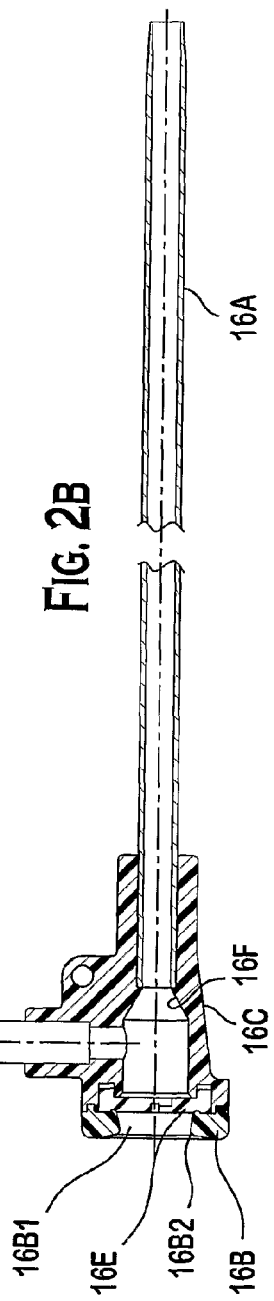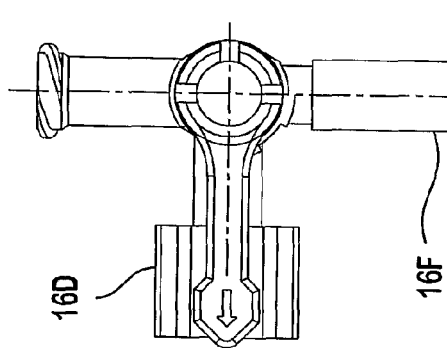

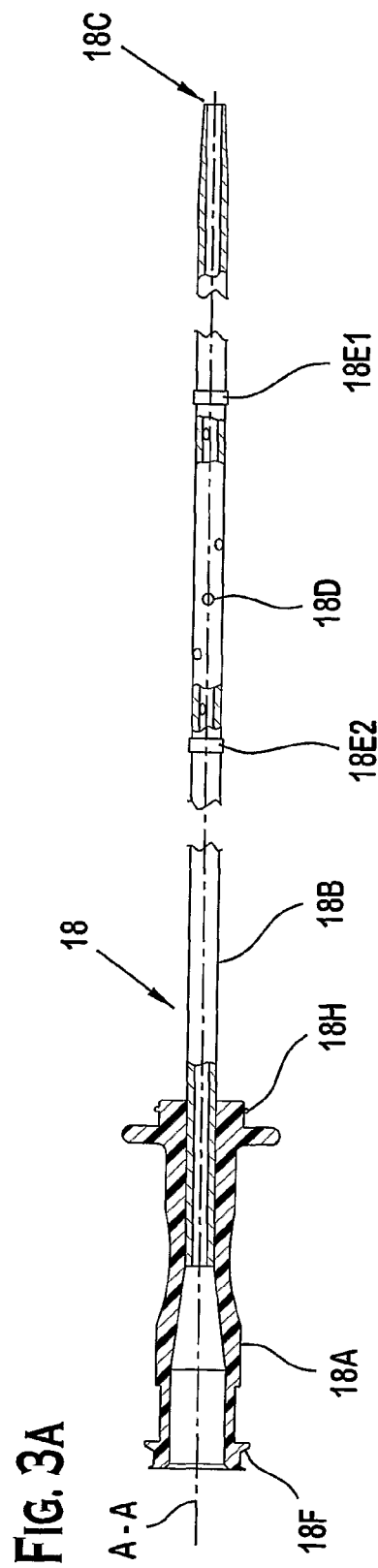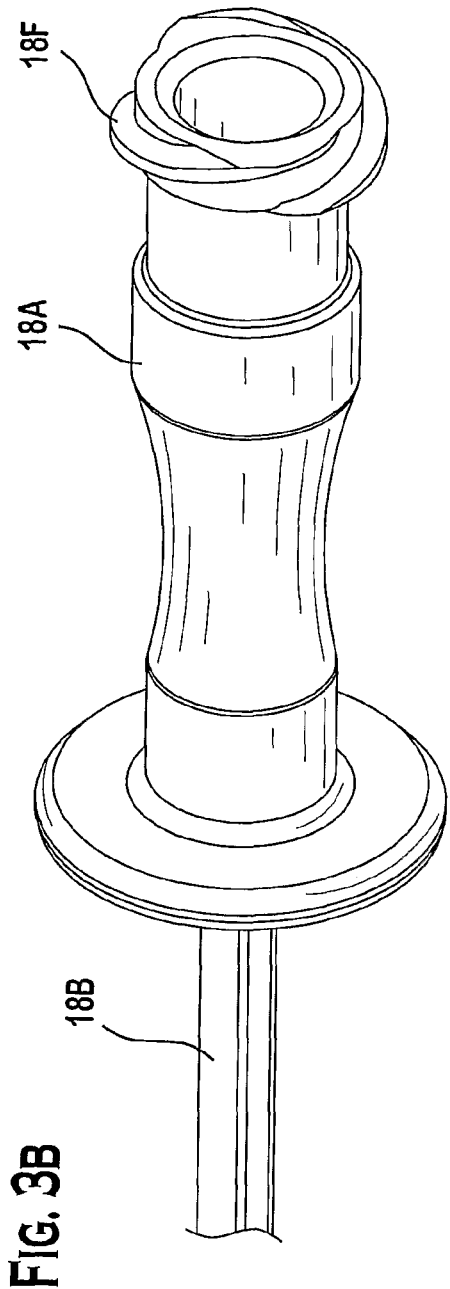
FIG. 3A
FIG. 3B

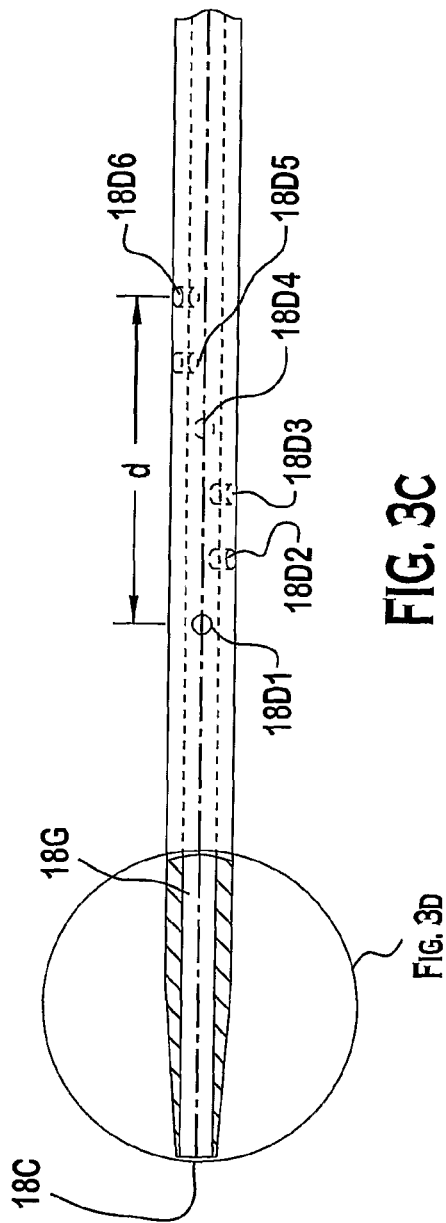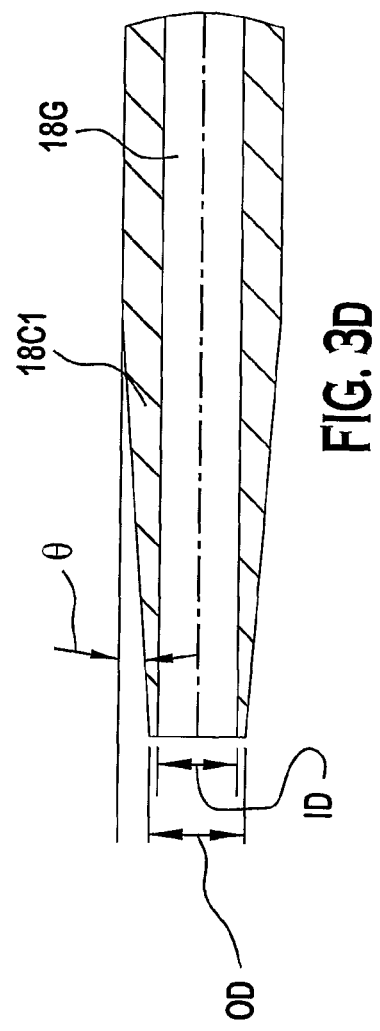
FIG. 3C
FIG. 3D

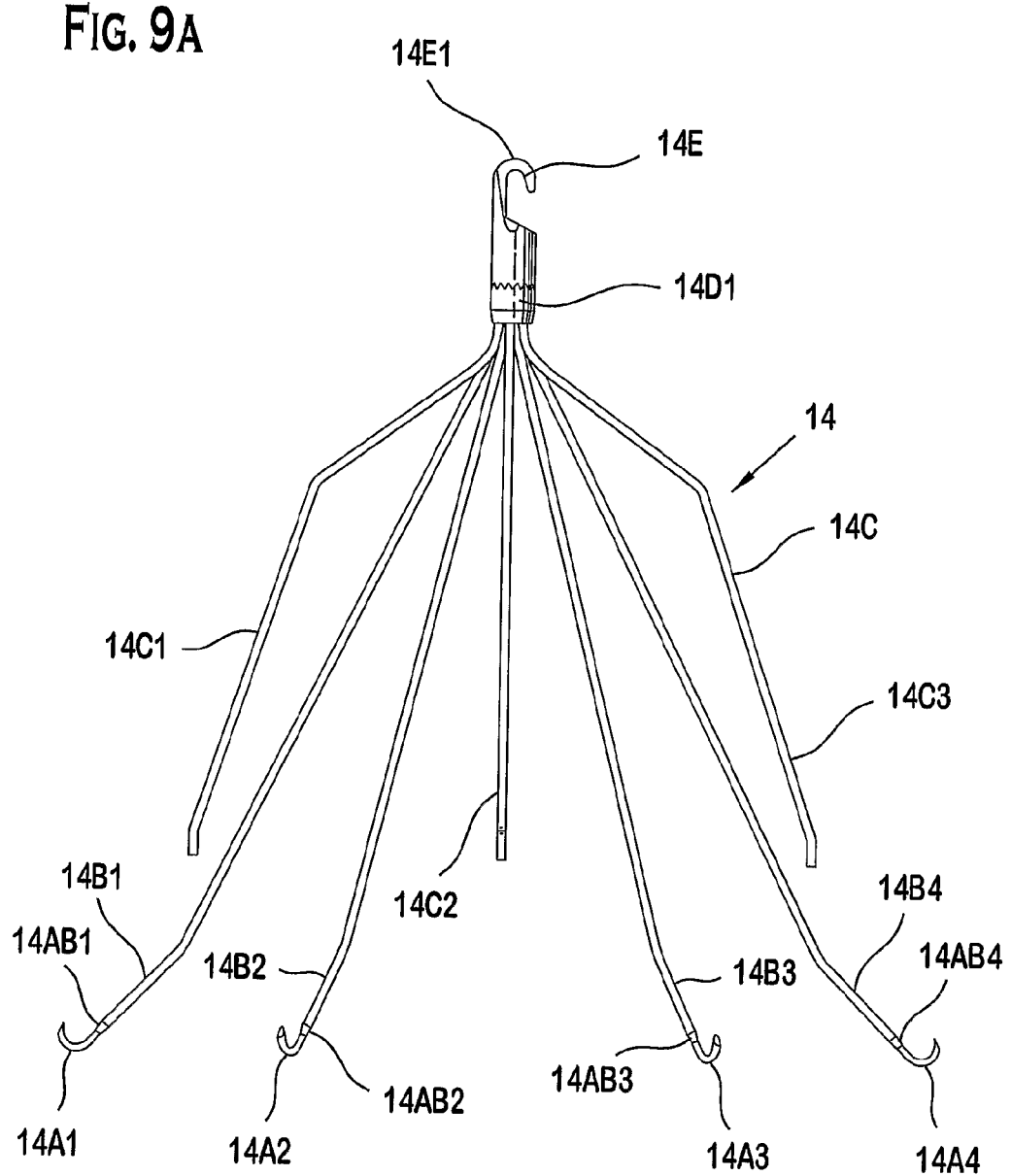

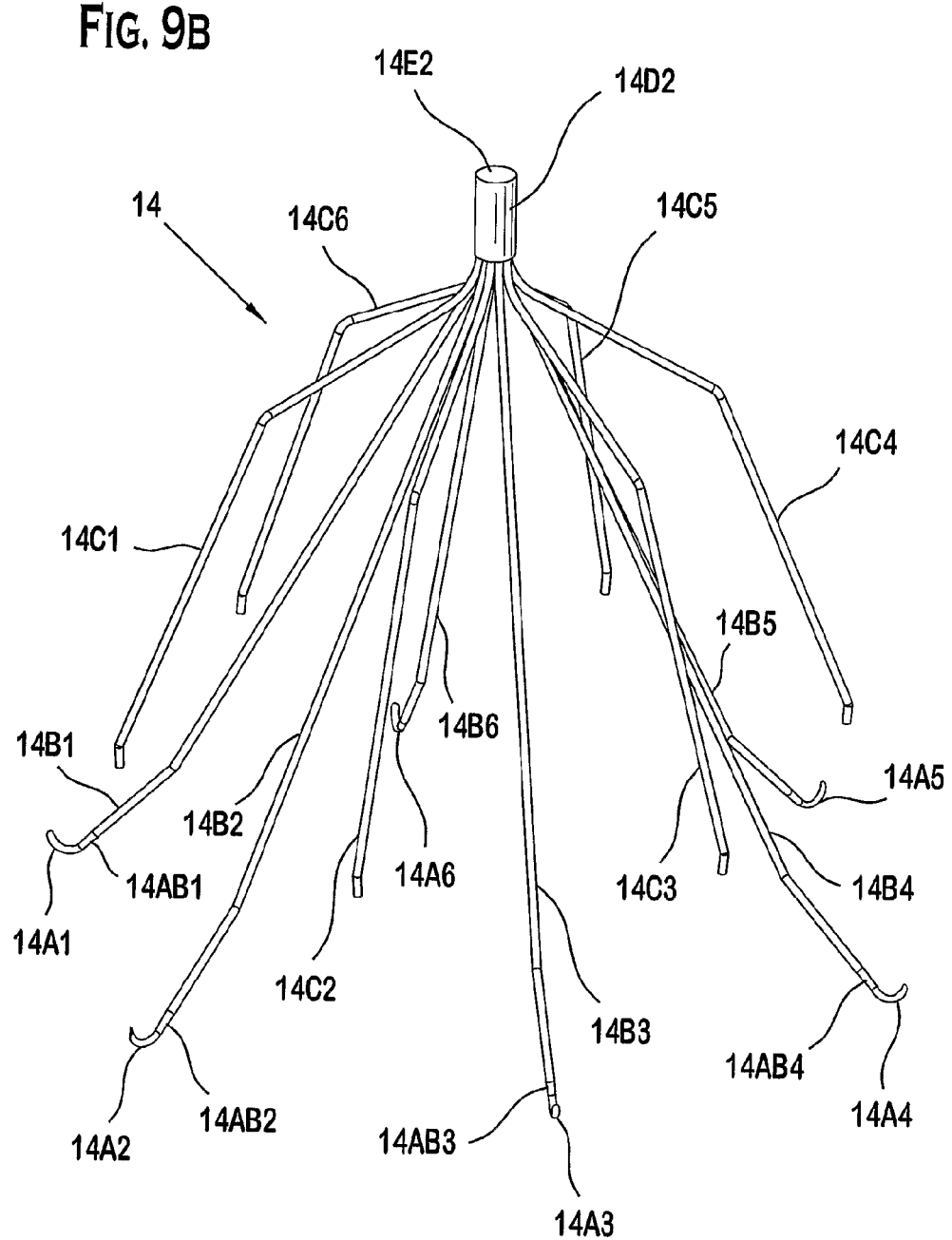

EMBOLUS BLOOD CLOT FILTER AND DELIVERY SYSTEM

PRIORITY DATA AND INCORPORATION BY REFERENCE

This application is a continuation of U.S. application Ser. No. 11/997,832, now U.S. Pat. No. 8,062,327, which is a U.S. national stage application under 35 U.S.C. §371 of International Application No. PCT/US2006/017890, filed May 9, 2006, which claims priority to U.S. Provisional Patent Application No. 60/706,596, filed Aug. 9, 2005, the entireties of which applications are hereby incorporated by reference.

FIELD OF THE INVENTION

This invention relates to a filter device that can be placed via a catheter delivery system in a vessel of a mammalian body to reduce the risk of embolisms. If needed, such filter can be removed from the vessel of a mammalian body without causing traumatic damage to the vessel of a mammalian body.

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein, such as the vena cava. These vena cava filters are generally designed to remain in place permanently. Such filters include structure to anchor the filter in place within the vena cava, such as elongate diverging anchor members with hooked ends that penetrate the vessel wall and positively prevent migration in either direction longitudinally of the vessel. The hooks on filters of this type are rigid, and within two to six weeks after a filter of this type has been implanted, the endothelium layer grows over the diverging anchor members and positively locks the hooks in place. Now any attempt to remove the filter results in a risk of injury to or rupture of the vena cava.

A number of medical procedures subject the patient to a short term risk of pulmonary embolism which can be alleviated by a filter implant. In such cases, patients are often averse to receiving a permanent implant, for the risk of pulmonary embolism may disappear after a period of several weeks or months. However, most existing filters are not easily or safely removable after they have remained in place for more than two weeks, and consequently longer-term temporary filters that do not result in the likelihood of injury to the vessel wall upon removal are not available.

One potential problem with the known delivery device is that the filter (including the elongated pusher on which the filter is attached thereon) can be pulled backward (i.e., proximally) towards the user, which may result in the inadvertent separation of the pusher assembly and the filter within the delivery device.

Another potential problem that can arise during delivery of a filter results from the placement of various hooks in a delivery device which can lead to the hooks entangling or interfering with one another.

SUMMARY OF THE INVENTION

The various embodiments provide for a blood filter delivery system that resolves potential problems of the known delivery system and filter. The system includes at least in part a catheter introducer, a storage member, an elongated assembly, and a blood filter. The catheter introducer has a coupling port connected to an elongated generally tubular member. The storage member can be coupled to the coupling port of the introducer and an adaptor, a Y-adaptor such as a Touhy-Borst Adapter. The elongated assembly provides a pusher assembly that has a first end that can be disposed in the storage member and a second end extending out of the Touhy-Borst Adapter. The elongated assembly can include a handle, a pusher, a spline member, and the blood filter. The handle can be disposed along a longitudinal axis of the elongated assembly proximate the second end. The pusher is disposed along the longitudinal axis proximate the first end of the elongated assembly. The spline member can be disposed on the elongated assembly along the longitudinal axis between the handle and the pusher. The spline member can have first and second boss portions spaced apart along the longitudinal axis to provide a circumferential gap or space therebetween. Alternatively, the spline member can have a single boss portion with splines and grooves. In an assembled, pre-delivery configuration, a blood filter, which has a plurality of anchor members disposed about the longitudinal axis each having a hook on their ends, is positioned between. the pusher and the gap. Each anchor member is positioned within a spline on the first boss portion of the spline member, with an anchor portion disposed in the groove of the spline member.

In yet another aspect, the various embodiments also include a pusher assembly that can be utilized with a vena cava filter delivery unit. The pusher assembly includes an elongated member, a handle, a pusher and a spline member. The elongated member extends along a longitudinal axis from a first end to a second end. The elongated member has a plurality of different cross-sections at various locations along the elongated member. The handle is disposed proximate the first end. The pusher is disposed proximate the second end. The member is disposed along the longitudinal axis between the handle and the pusher. The member has a main body, and first and second boss portions spaced apart along the longitudinal axis to provide a circumferential gap disposed about the longitudinal axis configured so that the gap accommodates a hook of a blood filter. Preferably, the member can be a spline member. Alternatively, the spline member can have a single boss portion with splines and grooves.

In yet a further aspect of the various embodiments, a method of delivering a blood filter is provided. The blood filter has a plurality of anchors about a longitudinal axis. Each of the anchors has a hook and at least two of the anchors define a span intersecting the longitudinal axis. The method can be achieved by locating a curved portion of each hook in an circumferential gap of a support assembly, the gap being disposed between two boss portions of the support assembly; locating a portion of each anchor in a longitudinal groove or spline that extends through one of the two boss portions; and enclosing the filter, including the plurality of locators and hooks, and the boss portions in a generally tubular member having an outside diameter of less than about 10 French (about 3.3 millimeters). Alternatively, the spline member can have a single boss portion with splines and the method can be achieved by positioning an anchor member within a spline in the boss and locating the curved portion of each hook proximal to the boss.

In yet a further aspect of the various embodiments, a bioactive agent can be coupled to the blood filter delivery system or push rod assembly described here. Alternatively, a bioactive agent may be delivered by the blood filter delivery system.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

FIGS. 1, 2A, 3A, 4, 5A, and 6A illustrate the components of one embodiment of a blood filter delivery system.

FIGS. 2B and 2C illustrate a proximal portion of a catheter introducer illustrated in FIG. 2A.

FIGS. 3B, 3C, and 3D illustrate various portions of a catheter dilator illustrated in FIG. 3A.

FIG. 4 is a cross sectional perspective view of Touhy-Borst Adapter.

FIGS. 5A and 5B illustrate a filter storage tube.

FIG. 6A illustrates an embodiment of an elongated push wire assembly.

FIGS. 9A, 9B, 9C and 9D illustrate components of respective blood filters usable with the delivery system of FIGS. 1, 2A, 3A, 4, 5A, and 6A.

DETAILED DESCRIPTION OF THE PREFERRED EMBODIMENTS

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient", "host" and "subject" refer to any human or animal subject and are not intended to be limit the systems or methods to human use, although use of the subject invention in a human patient represents a preferred embodiment.

The blood filter delivery system in the various embodiments mechanically integrates components to safely and reliably deliver and emplace a blood filter, like that illustrated in FIG. 9A, within a patient's blood vessel, such as the inferior vena cava. The system connects with a filter prepackaged in a filter storage tube 15 and includes the tools for properly positioning the filter in the vein and then initiating its deployment in a reliable fashion. Portions of the system may be prepackaged with the filter in the filter storage tube 15.

Figure 1:
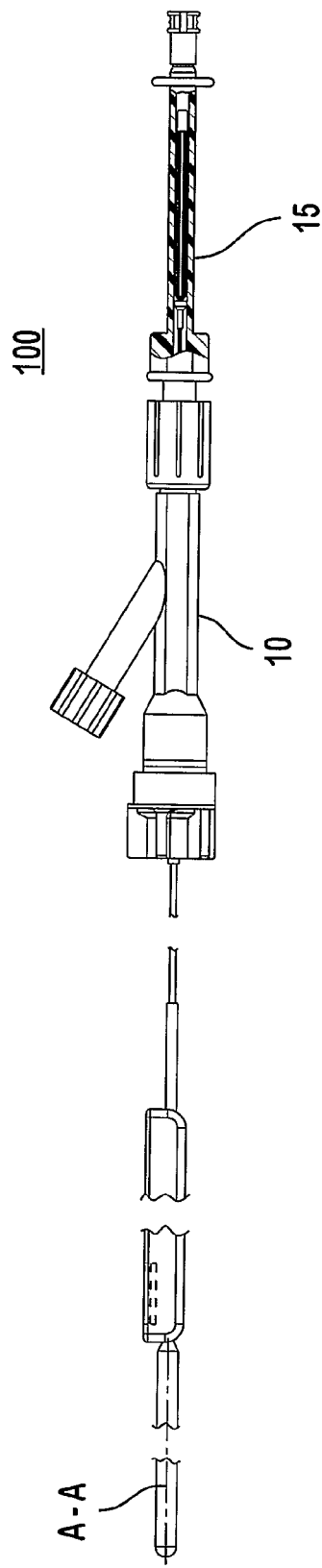

FIGS. 1-11 illustrate one of many exemplary embodiments. In an overview, as shown in FIG. 1, the blood filter delivery system 100 includes a storage tube 15 containing the filter 14, a catheter-like introducer 16 and a pusher assembly 12 to push the filter 14 from the storage tube 15, through the introducer 16 and then into the blood vessel, as well as supporting adapters. The blood filter delivery system 100 for a blood filter device is provided that extends along a longitudinal axis A-A. Components of the system include an adapter, such as a Y-adapter, and in particular a Touhy-Borst Adapter 10 (FIGS. 1 and 4), a filter storage tube 15 (FIGS. 1 and 5A) coupled to the Touhy-Borst Adapter 10 with a filter 14 stored in the storage tube 15 with an elongated pusher assembly 12 (FIG. 6A) that can be used to deploy the filter 14 (FIGS. 9A and 9B) in a blood vessel of a mammal. Other components that can be used with the system include a catheter introducer 16 (FIG. 2A) and a catheter dilator 18 (FIG. 3A). Each of the components in the system 100 is described in further details below.

Figure 2A:
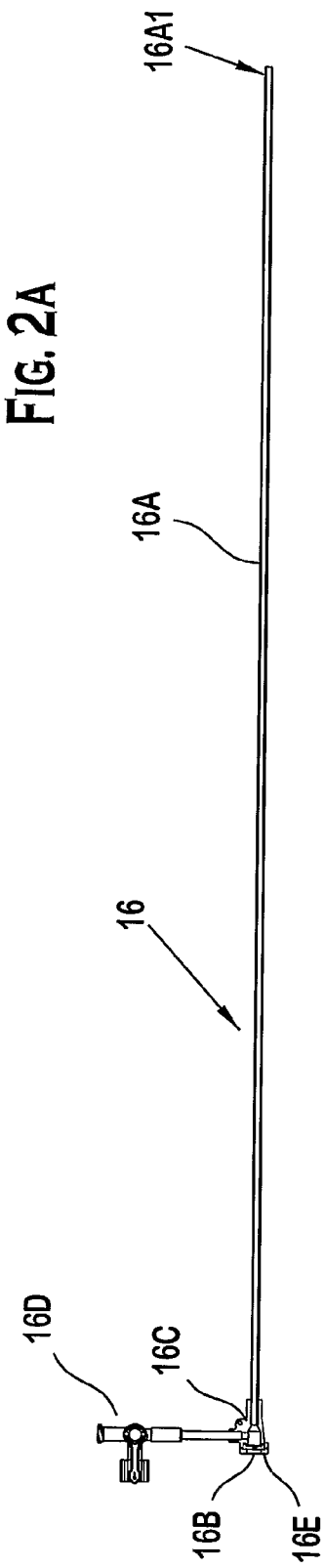

Referring to FIGS. 2A, 2B, and 2C, the catheter introducer 16 includes an elongated generally tubular member, referred to herein as an introducer sheath 16A coupled to a coupling port 16B via an introducer body 16C, which can be provided with a fluid valve 16D. The elongated introducer sheath member 16A is coupled to the introducer body 16C by suitable coupling techniques, such as, but not limited to, for example, threading, bonding, welding, swaging or adhesives. The introducer body 16C can be provided with an internal taper portion 16F that allows for insertion of the external taper portion 15C of the storage tube 15 and to allow for insertion of the filter tip 14E1 or 14E2 without interference by misalignment of the storage tube 15 to the introducer sheath 16A during insertion of the storage tube 15 into the introducer 16. Each of the respective taper portions 16F and 15C is provided with a taper angle of about 10 degrees to about 45 degrees with respect to the longitudinal axis A-A. The introducer sheath member 16A can be formed from a suitable polymer or a combination of polymers and other materials.

In various embodiments, the introducer sheath member 16A can be formed from a range of biocompatible flexible materials, such as polyurethane, polyethylene, polyamide, polyether block amide (PEBA), nylon, and combinations thereof, preferably from a combination of PEBA 70D with a PEBA 55D proximate the tip 16A1. The introducer sheath member 16A can be connected to the introducer body 16C by a bio-compatible adhesive, e.g., cyanoacrylates. In an embodiment, the distal tip 16A1 of the introducer sheath member 16A can be provided with a suitable radio-opaque marker, or include radio-opaque marker substances within the material of the introducer tip 16A1. As used herein, a radio-opaque marker is any material that is identifiable to machine or human readable radiographic equipment while the material is inside a subject's body, such as, by way of example but not by way of limitation, gold, tungsten, platinum, barium sulfate, or tantalum. Preferably, a tantalum radio-opaque marker is formed on or near the tip 16A1 of the introducer sheath 16A.

In a preferred embodiment, the introducer sheath 16A has an outside diameter of less than about 10 French and an inside diameter of less than about 9 French and more preferably, an outside diameter of about 9 French or less and an inside diameter of about 7 French or less, depending upon limits imposed by the diameter of the blood filter in the pre-deployed (i.e., folded) configuration. The introducer sheath 16A can have a length between approximately 305 mm and approximately 920 mm, and most preferably approximately 735 mm.

The introducer body 16C can be provided with a coupling port 16B, which can include a fluid seal 16E interposed between the port opening 16B1 coupled to the introducer sheath member 16A. The fluid seal 16E can be any suitable seal, such as but not limited to, a membrane or a flexible arcuate sectioned seal disposed about a central opening. Preferably, the seal 16E is an elastic membrane made of a suitable biocompatible elastomer, e.g., silicone, with the arcuate sectioned seal disposed about a generally central opening 16B1 for insertion of the dilator 18 or the filter storage tube 15. The introducer body 16C can be coupled to a fluid valve 16D via a polymeric (e.g., PVC) tubing 16F to allow for a suitable fluid (e.g., saline or a bio-active agent including drugs) to be introduced into the introducer sheath 16A or to drain fluid from the introducer member 16A. Preferably, the introducer valve 16D and introducer body 16C are made of polycarbonate, polyethylene, polyurethane, polyamide or PEBA. The coupling port 16B is be provided with an edge 16B2 that can be configured to act in a snap-lock arrangement with a complementary boss portion 18H of the dilator body 18A to attach and retain the dilator body 18A to the introducer body 16C. That is, the coupling port 16B includes the port body 16C that has the port opening 16B1, which has a seal 16E occluding the opening 16B1, and the port body 16C has the edge 16B2 (which may be circumferentially) disposed about the opening 16B1 so as to allow the introducer body 16C to be securable to a projection 15A formed on one end of the storage tube 15 via a sudden sharp engagement. The projection 15A of the storage tube 15 includes a curved surface disposed circumferentially about the longitudinal axis A-A.

During an implantation procedure, a clinician (e.g., surgeon or clinical radiologist) forms an opening to a vessel via a suitable puncture device. Thereafter, a catheter dilator 18 is used in conjunction with the introducer 16 to provide a conduit to the internal of the body so that contrast agent or dye can be provided into the body to determine the implantation site. Referring to FIGS. 3A-3D, the dilator 18 includes a dilator hub 18A coupled to a dilator tube 18B. The dilator body 18A is provided with a threaded fitting 18F at the proximal end to connect to a suitable fluid valve, e.g., the Touhy-Borst Adapter 10 so that fluids can be injected into the dilator fluid passage 18G. A number of fluids can be injected during operation, including dye marker for enabling fluoroscopic imaging of the introducer 16 within the patient, saline to flush body fluids from and provide lubrication within the introducer 16 and, in some embodiments, cooled saline to maintain temperatures of the push wire and/or the filter below their martensitic-to-austenitic transition temperature. The dilator body 18A is coupled to a dilator tube 18B that extends longitudinally to provide a longitudinal passage 18G of approximately 661 millimeters from the dilator body 18A to the distal dilator end 18C. At the distal dilator end 18C, the dilator tube 18B can be provided with a generally truncated conic tip defined by the outer surface of the distal end 18C. The conic tip is utilized to allow the dilator to be inserted through valve 16E and the introducer sheath 16A. The conic tip 18C1 can be defined by a conic outer surface that extends at a conic angle 0 of about 4 degrees with respect to the longitudinal axis with an inside diameter ID of about 1 millimeter (about 0.041 inches) and an outside diameter OD of about 2.1 millimeters (about 0.084 inches).

A plurality of fluid communicating ports 18D may be provided through the wall of the dilator tube 18B in a generally spiral configuration to allow for injection of contrasting dye. Each fluid communicating port 18D can be of a suitable configuration such as, but not limited to, for example, circular, square, diamond. Preferably, six circular communicating ports 18D1, 18D2, 18D3, 18D4, 18D5, and 18D6 are provided with an opening diameter of about 0.037 inches, and each port is spaced apart from the adjacent port over a distance d of about 0.16 inches along the longitudinal axis A-A and angularly disposed about the longitudinal axis A-A over an interval of 60 degrees with respect to each adjacent port.

One or more radio-opaque marker band 18E may be coupled to the dilator body 18A by a suitable technique, such as, but not limited to, forming a radio-opaque material integrally with the dilator tube 18B or mounting a separate radio-opaque material onto or inside the dilator tube 18B. Preferably, two radio-opaque markers 18E are swaged onto the dilator tube 18B near the distal end 18C, with a first marker 18E1 located at approximately 28 millimeters from the tip 18C and a second marker 18E2 located at approximately 28 millimeters from the first marker 18E1. In these locations relative to the tip 18C, the radio-opaque markers 18E1 and 18E2 enable a clinician to approximate the inside diameter of a blood vessel under fluoroscopic imaging. In the exemplary embodiments, the ports 18D1-D6 are arranged in a spiral configuration between two radio-opaque marker bands.

Also preferably, the dilator tube 18B can be formed from a variety of biocompatible flexible materials, such as polyurethane, polyethylene, polyamide, polyether block amide (PEBA), nylon, and combinations thereof, preferably from a HDPE/LLDPE blend of polymer and 18-20% of barium sulfate by weight, with the barium sulfate providing the radio-opaque functionality.

When assembled, the dilator tube 18B slides inside the introducer sheath 16A such that the dilator tube tip 18C1 extends through the introducer tip 16A1. The introducer 16 and catheter dilator 18 can be packaged separately, such as in separate sterilized packages, so they can be unsealed and assembled by the clinician at the time of the procedure. Alternatively, the catheter dilator 18 can be inserted into the introducer 16 at the manufacturer and sealed together in a sterile package, such that the clinician can unpack and use the two components as a unit.

Figure 4:
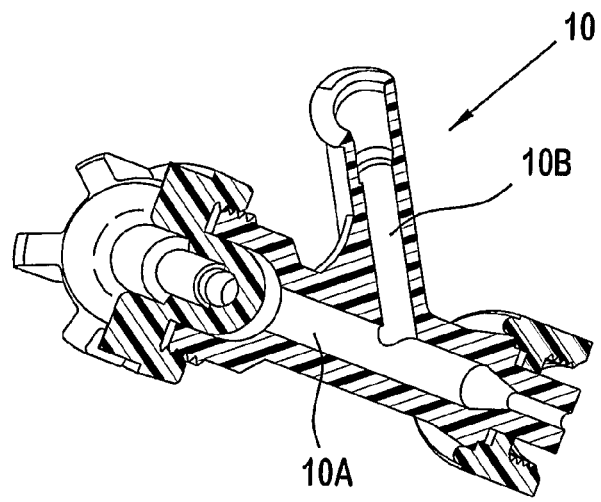

Referring to FIG. 4, the Touhy-Borst Adapter 10 may be provided with at least two passages. A first passage 10A allows for movements of the pusher rod. A second passage 10B allows for flow of saline into the introducer 16 to increase, in most cases, lubricity between the elongated pusher assembly 12 and the introducer 16 as the elongated pusher assembly 12 is moved along longitudinal axis A-A through the second passage 10B and the passage of the introducer 16. The saline solution also can be chilled before introduction into the Touhy-Borst Adapter 10.

Figure 5A:
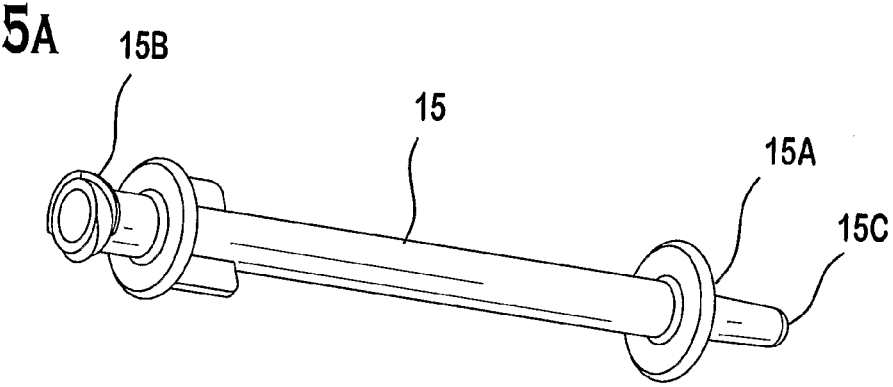
Figure 5B:
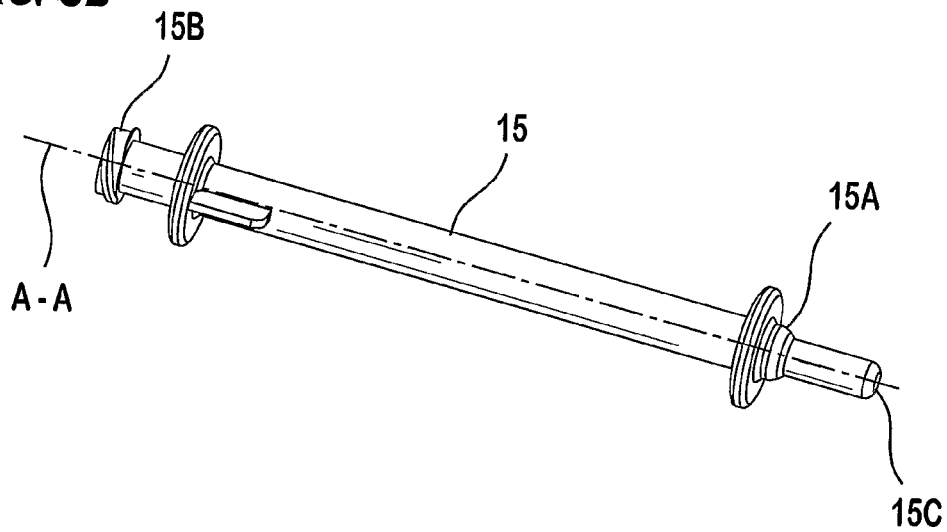

Referring to FIGS. 5A and 5B, a storage tube 15 for various blood filters (e.g., FIGS. 9A and 9B) can be introduced between the Touhy-Borst Adapter 10 and the introducer 16 in the delivery system 100. The storage tube 15 is provided with a suitable fitting (e.g., threaded, snap or luer fitting) at both ends. In the preferred embodiments, the storage tube 15 has a threaded fitting 15B at one end to connect with the Touhy-Borst Adapter 10 and a snap fitting 15A at the other end to connect with the introducer 16, as well as a taper section 15C for insertion into the preferably triple arcuate sectioned elastomeric seal 16E. Alternatively, one end can be provided with a snap-fitting and the other end can be provided with a threaded fitting. The storage tube 15 can be formed from any of a number suitable polymers and, preferably, polycarbonate.

Figure 6A:
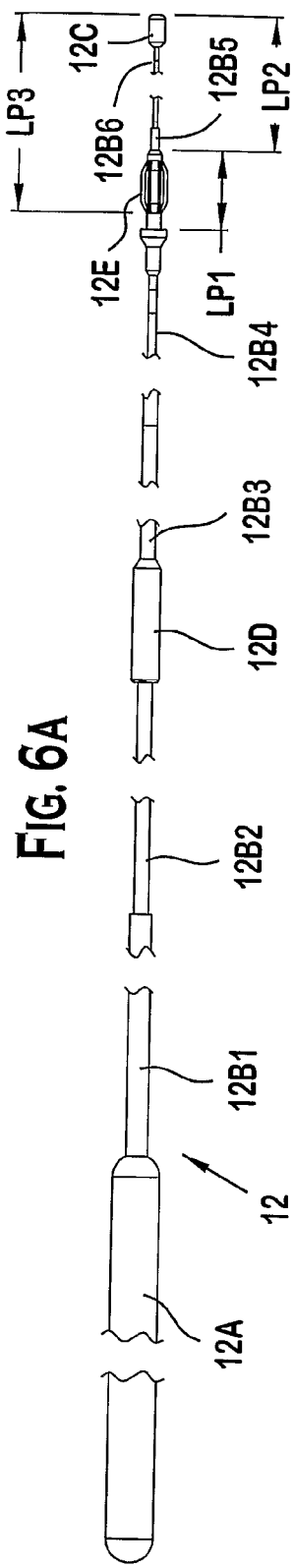

Referring to FIG. 6A, an embodiment of the elongated pusher assembly 12 is shown separate from other components of the delivery system 100. In particular, the pusher assembly 12 can be provided with a handle 12A coupled to an elongated member 12B with various cross-sectional areas 12B1, 12B2, 12B3, 12B4, 12B5, 12B6 and so on at various locations along the pusher assembly 12 from proximate the handle 12A to a pusher 12C. For example, near the handle 12A, the assembly 12 can be provided with a hollow stainless steel tube 12B1 connected to a suitable alloy material, including, for example, a shape memory alloy (e.g., Nitinol), wire on which various members can be disposed thereon such as a stop member or boss portion 12D, spline member 12E and the pusher member 12C. The pusher assembly 12 has a longitudinal length in the range of about 800 mm to about 1000 mm, preferably of about 907 mm. The handle 12A can be formed of a number of metallic, polymer or plastic materials, and is preferably formed from PEBA coupled to a stainless steel hollow section 12B1 having a diameter of about 0.041 inches. The handle 12A is coupled to a super-elastic shape-memory alloy wire having various diameters (e.g., shown at 12B2-12B6) smaller than the diameter of the stainless steel section 12B1 with a diameter at the distal end of about 0.013 inches connected to a generally cylindrical pusher 12C. The utilization of decreasing cross-sectional areas in the pusher assembly allows for flexibility at the distal end and pushability at the proximal end.

The terminal distal end of the generally cylindrical pusher member 12C is longitudinally spaced from a nearest portion of the spline member 12E at a distance of about 34 mm. The pusher member 12C is configured to push against the filter's hub 14D (illustrated in FIG. 8) as the pusher assembly 12 is advanced into the introducer 16. The spline member 12E is configured with a number of radially positioned splines that alternate with grooves in a first portion 12E, each spline being sized to accommodate one of the elongated portions of the anchor members 14B1, 14B2, 14B3, 14B4, 14B5, and 14B6, providing lateral positioning of the anchor member while the filter 14 is in the stored configuration. The pusher member 12C is separated from the spline member 12E by a flexible narrow cross section portion of the pusher wire 12B6 which provides a volume for accommodating both the anchor members 14b and the positioning members 14C of the filter 14. The distal end of the pusher member 12C is separated from the distal end of the spline member 12E by a distance LP2, which is separated from the boss 12E2 by distance LP1. Thus, the overall distance from the distal end of the pusher member 12C to the boss 12E2 of the spline member 12E is distance LP. In other words, LP=LP1+LP2 where LP1 is measured from the planar surface PS to the terminal end 12G and LP2 is measured from the terminal end 12G of the spline member 12E to distal end of the pusher member 12C. To facilitate deployment of the filter 14, the length LP and preferably LP3 is slightly longer than the length LF (FIG. 7A) of the filter 14 in the pre-stored or pre-deployed configuration inside the storage tube 15. This dimensional parameter is believed to impart a lateral force or preload unto the hub of the filter 14. As a consequence, the anchor members are stretched and the push wire portion 12B6 is compressed in the stored configuration. When the filter 14 is deployed and the introducer sheath 16A is retracted proximally sufficient to uncover the hook ends of the anchor members 14A, the anchor members move radially thereby releasing the preload force. Hence, the preload in pusher wire portion 12B6 provides a spring force that helps ensure that the anchoring members are released out of constrainment by the grooves (e.g., 12F1) of the spline member and introducer sheath 16A. The distances LP1, LP2, and LP3 depend upon the dimensions of the filter 14. In an embodiment suitable for use with the filter illustrated in FIGS. 7A, 7B, 9A and 9B, the length LP1 is about 6 millimeters and LP2 is about 34 millimeters so that the total length LP or LP3 is about 40 millimeters.

Figure 6B:
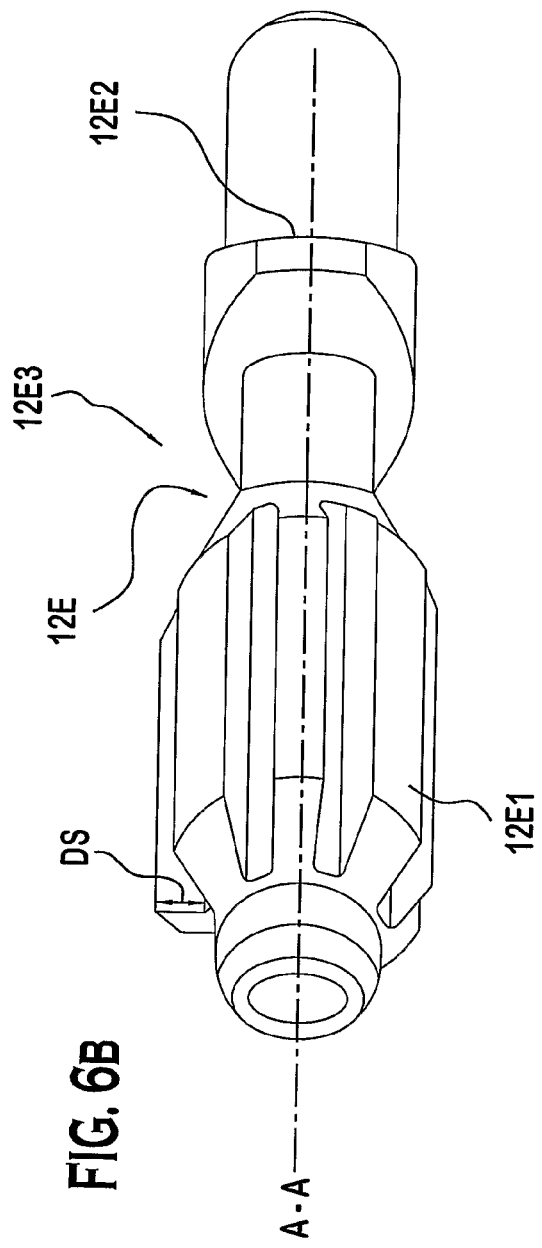
FIGS. 6B and 6C illustrate a splined member of FIG. 6A in two operating configurations.

Referring to FIG. 6B, the spline member 12E has a first boss portion 12E1 and a second boss portion 12E2 spaced apart from each other to define a circumferential gap 12E3 therebetween. The gap 12E3 can be a non-annular gap but preferably is an annular gap in the general shape of a toroid about the longitudinal axis A-A. The first boss 12E1 has a plurality of grooves 12F1-12F6 that extend longitudinally along the longitudinal axis and are disposed, preferably, arcuately about the longitudinal axis through the first boss 12E1. In a preferred embodiment, the longitudinal grooves 12F2 define splines 12SP where each spline extends with a length L of about 3.3 millimeters (about 0.13 inches) along the longitudinal axis at a depth DS of about 0.4 millimeters (about 0.015 inches) radially with respect to the outer surface of the splines 12SP, having a width of about 0.015 inches. Viewed another way, the first boss features a plurality of longitudinal projections (i.e., splines 12SP) spaced apart radially from each other and disposed about a generally cylindrical main surface to define a plurality of longitudinal grooves 12F1-12F6. One longitudinal groove 12F is provided for each anchor member 14B of the blood filter 14. In the assembled and pre-deployment configuration, the anchor members 14B are folded down so that a lower portion lies within a groove 12F as illustrated for one anchor member 14B positioned in groove 12F3 in FIG. 6C. So configured, the grooves 12F hold the anchor members 14B in place, providing lateral stability necessary to prevent anchor members from crossing and becoming entangled during storage and delivery. Similarly, the gap 12E3 provides room for the hook ends of the anchor members to be positioned so as to prevent interference or entanglement, as illustrated in FIG. 7B.

The second boss 12E2 of the spline member 12E can be a generally cylindrical member disposed about the generally cylindrical main surface. As shown in FIG. 6B, a first embodiment of the spline member 12E is provided with a non-circular stop member or second boss portion 12E2. Alternatively, another embodiment of the spline member 12E is provided with a generally circular stop member or boss portion 12E2. In an embodiment, the generally cylindrical boss member includes a generally planar surface PS disposed about the generally cylindrical surface CS and spaced apart from a nearest portion of the first boss 12E1 at a distance G of about 1.3 mm, or about 0.05 inches, along the longitudinal axis. The spline member 12E can be made of a suitable material including, for example, polymers, metal alloys such as Nitinol, titanium, or stainless steel. Preferably, the spline member 12E is made of type-303 stainless steel and processed with appropriate deburring and cleaning operations to render the piece suitable for surgical use.

Figure 6C:
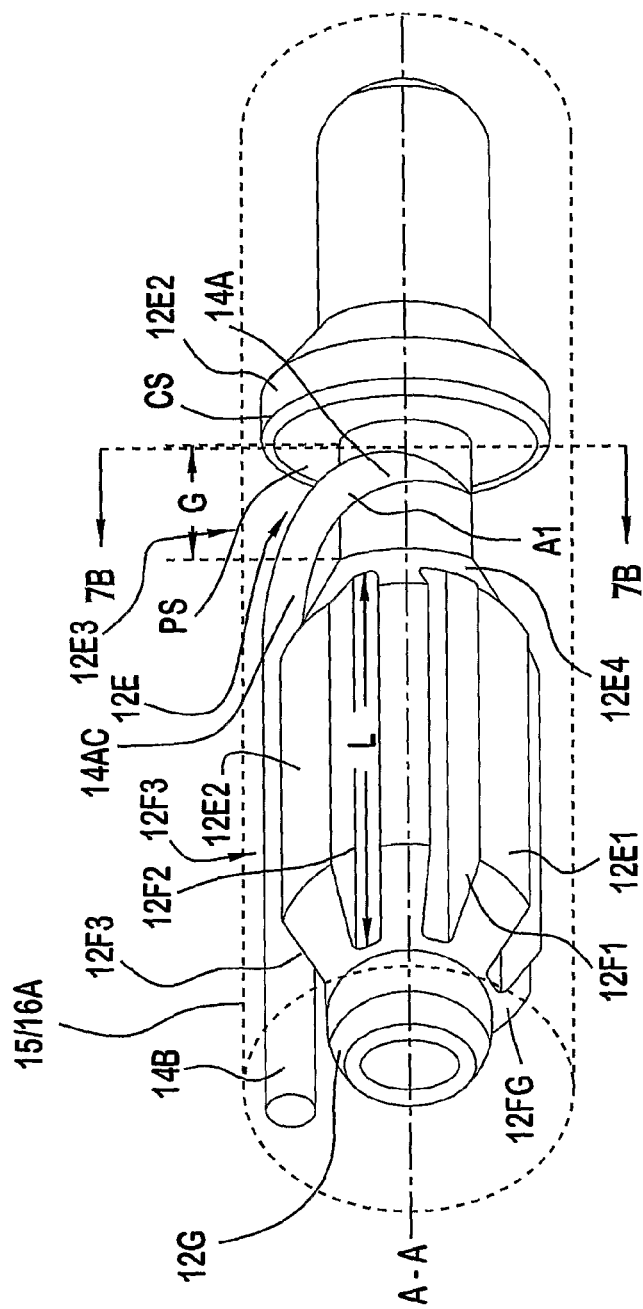

Although the latter embodiment of the spline member 12E in FIG. 6C is preferred, the former embodiment in FIG. 6B having a non-circular stop member or boss portion is believed to allow for the control of the spring force during deployment of the blood filter 14 in some applications of the delivery system 100. Additionally, the non-circular cross section of the second boss 12E2 shown in FIG. 6B permits fluids to pass between the spline member 12E and the walls of the introducer sheath 16A so saline flow can pass through the filter and so the spline member 12E does not function as a piston during insertion and withdrawal movements.

Referring to FIGS. 9A and 9B, two exemplary embodiments of the blood filter 14 are shown. Each filter 14 has some common features, For example, locator members 14C1, 14C2, 14C3, 14C4, 14C5, 14C6 and anchor members 14B1, 14B2, 14B3, 14B4, 14B5, and 14B6 are provided that extend in the same direction from a hub 14D1 or 14D2. Hooks 14A1, 14A2, 14A3, 14A4, 14A5, and 14A6, each having a smaller cross-sectional area than the cross-sectional area of each of the anchor members 14B1-14B6 are respectively connected to the anchor members 14B1-14B6. The spread of the anchor members 14B1-14B6, as measured through the longitudinal axis A-A of the filter 14 or the hub 14D1 or 14D2 is about 40 millimeters in a deployed (but not installed in the blood vessel) position. Differences include the overall length of the two embodiments in which the embodiment of FIG. 9A is about 2 millimeters longer than the embodiment of FIG. 9B in a stored configuration in the storage tube 15; this difference in length being due to the snareable hook on the filter 14 in FIG. 9A. The example blood filters 14 also include a hub 14D1, 14D2 which can serve as the attachment structure for the anchor and locator members. A radio-opaque material can be incorporated in the hub 14D1, 14D2 of the filter. Radio-opaque material can be in the form of an additional structure added to the hub, such as a cap, sleeve, shim, wire or braze included around or in the hub assembly. Alternatively, the hub itself can be fowled of a radio-opaque alloy.

Figure 9C:
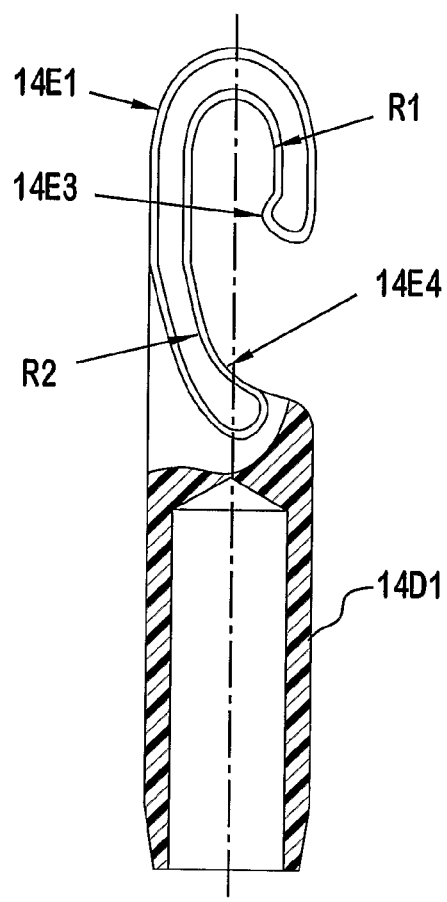
Figure 9D:
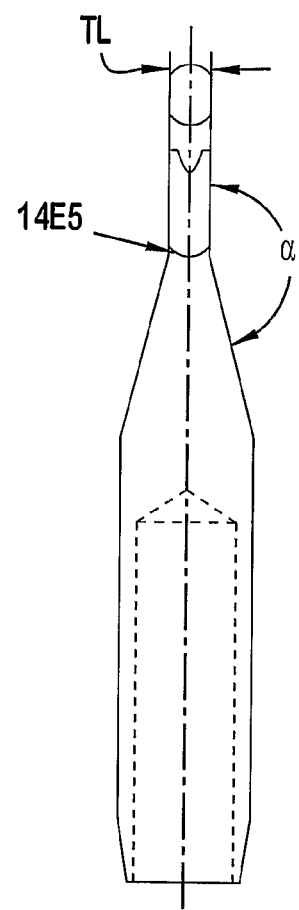

Referring to FIGS. 9C and 9D, details of the snareable tip 14E1 for the hub 14D1 are provided. Specifically, the snareable tip 14E1 is believed to allow, optionally, for repositioning (e.g., by capturing and pulling the filter into a catheter) or potentially complete removal of the filter. The snareable tip is provided with a protuberance 14E3 to ensure that a snare will tend to be retained proximate the radiused surface R1. To assist in the capture of a snare (not shown), second radiused surface R2 is included to provide a generally smooth guided entry into the first radiused surface R1. Assisting second radiused surface R2 are tapered side surfaces 14E5 having an included angle α of about 160 degrees. The thickness TL of the tip 14E1 is preferably about 0.5 millimeters (about 0.02 inches), the overall length of the tip and hub is preferably about 7.6 millimeters (about 0.3 inches), and the hub 14D1 is preferably generally circular with an outer diameter of about 1.8 millimeters (about 0.07 inches).

Additional details of the blood filter 14 are provided in U.S. Provisional Patent Application No. 60/680,601, filed May 12, 2005, as well as in International Application No. PCT/US2006/017889, filed May 9, 2006 that claims priority to the antecedent provisional patent application, which published as WO 2006/124405, each of which applications are hereby incorporated by reference in their entirety.

Figure 10:
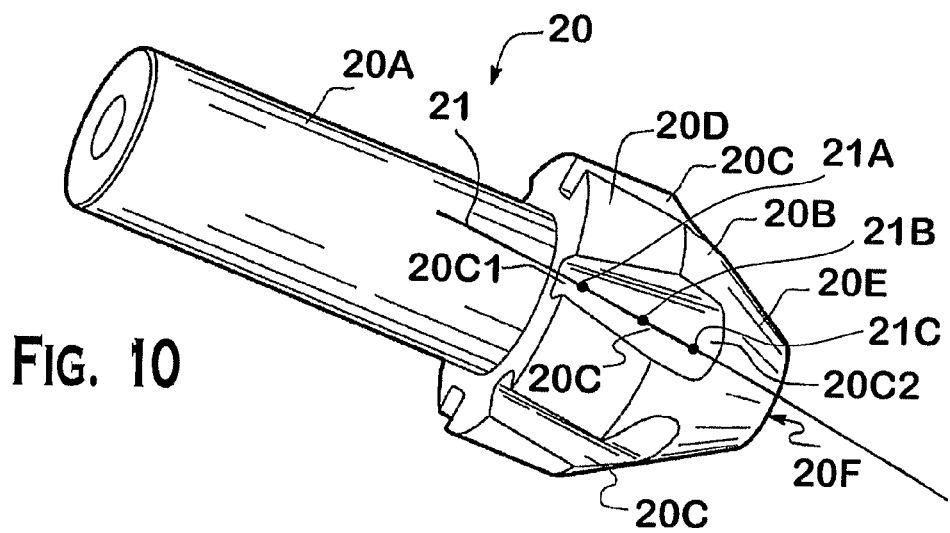
FIG. 10 illustrates an alternative embodiment of the spline member.
Figure 11:
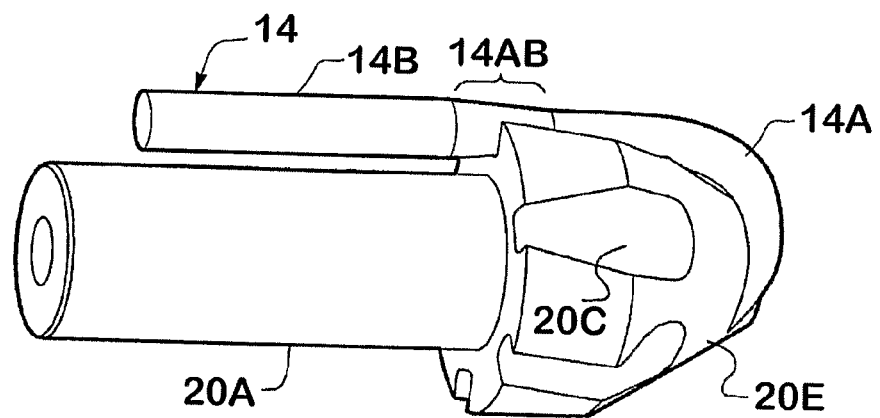
FIG. 11 illustrates a filter anchor member positioned about the spline member illustrated in FIG. 10.

An alternative embodiment for the splined member 20 is illustrated in FIGS. 10 and 11. Referring to FIG. 10, in this embodiment of the splined member 20, the spline portions 20C are provided within the boss 20B. In the embodiment illustrated in FIG. 10, the boss 20B features a first, distal conical surface 20D and a second, proximal conical surface 20E provided before a shaft portion 20A and an end, connector portion 20F. The end portion 20F can include a central bore that may be threaded to accept the distal end of the elongated pusher member 12B4. Grooves 20C provided in the boss 20B are configured to accommodate and radially position the anchor members 14B. In an embodiment illustrated in FIGS. 10 and 11, the grooves 20C are narrower at a distal end 20C1 than at the proximal end 20C2.

Referring to FIG. 11, the conical configuration of portions 20D and 20E are provided so that when the anchor 14 is positioned within the spline 20C, the hook 14A portion fits over the proximal conical portion 20E so that the diameter subtended by the hooks 14A positioned about the boss 20D is less than the interior diameter of the introducer 16. In an embodiment, where the anchors 14 have a narrower width (or cross section) in the hook portion 14A than the shank portion 14B, the narrower distal portion 20C1 of the splines 20D has a groove 20C whose width (as measured on an imaginary outermost circumference connecting the splines 20D) or cross section is smaller than the width or cross section of the anchor shank 14B. In this embodiment, the anchor 14 features a conical shaped portion 14AB where the cross section decreases from that of the shank portion 14B to the hook portion 14A. In other words, at least one anchor portion (e.g., 14B1, 14B2, 14B3, . . . 14B6) of a filter 14 can be located in at least one of the plurality of grooves 20D disposed between splines 20D where the anchor portion (having portions 14A and 14B) has a maximum width at portion 14B greater than a minimum width 20C1 of the groove. Since the narrow portion 20C1 of the spline 20C is wider than the cross section of the hook portion 14A but narrower than the anchor shank portion 14B, the narrow portion 20C1 will engage (e.g., in an interference fit) a portion of the anchor transition portion 14AB. When the anchors 14 are positioned within the grooves 20C in this embodiment, the anchor 14 cannot move in a proximal direction beyond the point where the anchor transition portion 14AB engage the narrow portion 20C1. In this manner, the spline 20C restrains the anchor 14 longitudinally. It should be noted that the narrower portion 20C1 does not have to be located at the proximal end of the boss 20B. Depending on the length of the hook portion 14A, the narrower portion 20C1 can be disposed at any one of a plurality of positions between 21A, 21B, and 21C.

Figure 7A:
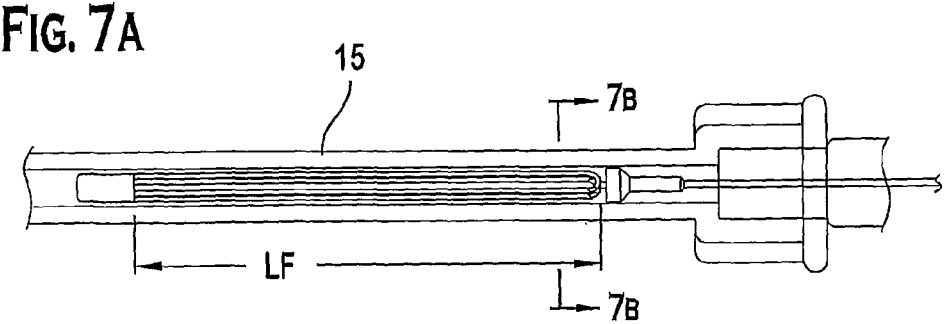
FIGS. 7A and 7B illustrate, respectively, a side view of a filter in a storage tube and coupled to the splined member of FIG. 6B and a sectioned view of the same.
Figure 7B:
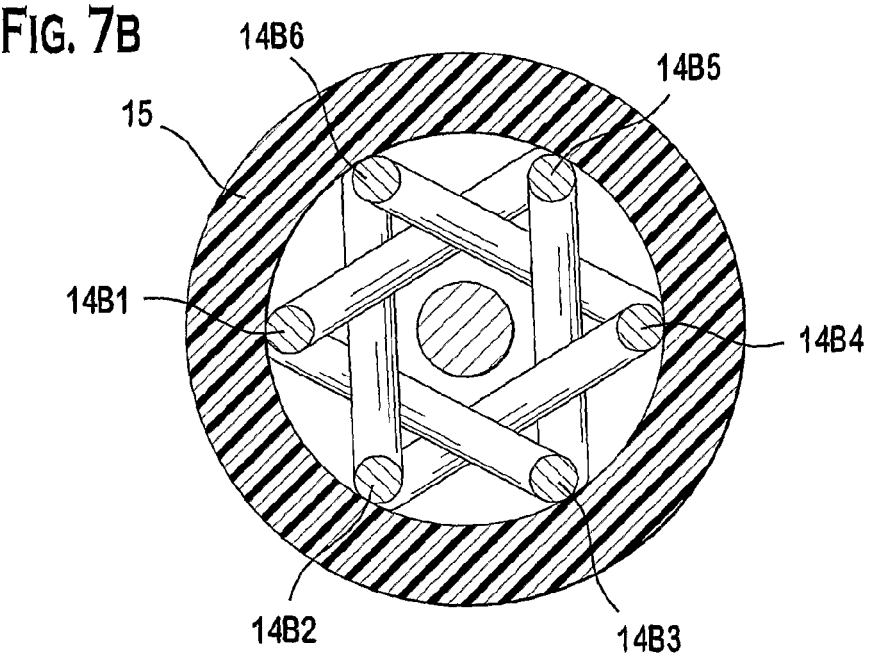

Several design features are believed to be important in advancing the state of the art. For example, the use of the splined member 12E is believed to be important in preventing a pull back of the blood filter 14 from the storage tube 15 toward the proximal direction. Specifically, the spline member 12E is provided with a gap 12E3 to store the hooks of the blood filter 14 in a pre-delivery configuration (FIGS. 6C, 7A, and 7B) that forms an interference fit between the hooks 14AC, the spline member 12E and the storage tube 15 and introducer sheath 16A. For clarity, only one anchor member 14B and Hook 14A are shown in FIG. 6C. However, the anchor members 14B1, 14B2, 14B3, 14B4, 14B5, and 14B6 on which the hooks 14A are respectively connected are in a spiral configuration as shown in the side view of FIG. 7A while the hooks are shown in the sectioned-view of FIG. 7B. The placement of the hooks, as shown in the example of FIGS. 6C and 7A, presses the anchor members against the wall of the storage tube 15 and introducer sheath 16A, with the of the hook tip 14B angled in a proximal direction and in contact with the wall as illustrated in FIG. 7B elements 14B1, 14B2, 14B3, 14B4, 14B5, and 14B6. When the filter 14 is advanced in the distal direction, the hook tips 14B slid easily along the wall of the storage tube 15 and introducer sheath 16A. However, if the filter 14 is moved in the proximal direction (towards the right side of FIG. 6C), the tapered surface 12E4 (FIG. 6C) causes a portion of the hook 14A to slide up on the tapered surface 12E4. Because at least the hook 14A is constrained between the spline member and the introducer sheath 16A, a portion of the hook 14A engages one of the wall of the storage tube 15 and introducer sheath 16A in a ratchet-like fashion, presenting a high resistance to motion in that distal direction. As a consequence of this configuration of the filter about the splined member 12E, approximately 5 pound-force is required to cause the filter 14 and pusher assembly 12 to move toward the user or operator (i.e., in a proximal direction) but generally little or no force for movement away from the user or operator (i.e., in a distal direction). That is, the placement of the hooks 14A in relation to the spline member 12E and the storage tube 15/introducer sheath 16A prevents proximal movements of the elongated assembly 12 if the force applied to the assembly 12 is less than a desired value. It should be noted that the desired force value can be selected as being more or less than approximately 5 pound force as a function of at least the cross-sectional area of the hooks 14, the configuration of the spline member 12E (e.g., the angle of tapered surface 12E4), the inside diameter of the storage tube 15 and introducer sheath 16A. This design feature is believed to prevent inadvertent dislodgement of the anchors from the spline member, which may cause crossing of the anchors.

Additionally, the use of the splined member in the various embodiments described herein is believed to alleviate the problem of the plurality of hooks crossing each other as they are mounted in the storage tube 15 or while the filter is being deployed via the introducer sheath 16A (regardless of whether the filter and system are being tested inside or outside of a host body). In particular, the longitudinal grooves 12F1-12F6 (which can be linear, curved or curvilinear) positioned circumferentially about the longitudinal axis A-A, in combination with the gap 12E3 allows the anchor members 14B and associated hooks 14A to be held in a generally precise configuration (FIG. 7B) while in storage and during delivery into a vein to virtually eliminate the entanglement or crossing of the hooks.

In particular, the use of the splined member 20, shown and described in relation to FIGS. 10 and 11, is believed to reduce a force needed by a clinician to deploy the filter 14 from the distal tip of the introducer during an implantation procedure. The use of spline member 20 reduces an interaction between hooks, sheath wall and marker band to reduce deployment force. Testing has demonstrated the axial force applied to the pusher is approximately 2 lb-force when the spline member 20 (FIG. 10) is utilized.

Further, the use of the complementary snap-fittings for the storage tube 15 and introducer body 16C along with the internal and external tapers 16F and 15C is believed to allow for precise coupling of the two components without having to align the storage tube with the body 16C and threading the two components together, which under some circumstances could result in cross-threading or interference with the tip of the filter 14 into the introducer sheath 16A.

By virtue of the delivery system 100, among other items, described and illustrated herein, a method of packaging a blood filter 14 is provided. As noted above, the filter 14 includes a plurality of anchor members 14B1-14B6 about a longitudinal axis; each of the anchor members 14B1-14B6 having a hook 14A and at least two of the anchor members 14B1-14B6 defining a span intersecting the longitudinal axis and between the at least two anchor members of about 40 millimeters. The method of packaging the filter 14 including hooks 14A having a cross sectional area A1 along the arcuate portion 14AC of the hook 14A that is greater than about 0.04 squared millimeters (or about 0.000057 squared inches), involves locating the curved portion 14AC of each hook in the annular gap 12E3 disposed between the first and second boss portions 12E1 and 12E2 of spline member 12E; and enclosing the filter 14, including the plurality of locators and hooks, and the boss portions in a generally tubular storage tube (e.g., storage tube 15 or introducer sheath 16A) having an outside diameter of less than about 10 French (about 3.3 millimeters) and preferably about 9 French (about 2.9 millimeters) and an inside diameter less than 9 French, preferably less than about 7 French (about 2.3 millimeters). By virtue of the configuration of the blood filter 14 with its hooks 14A, spline member 12E and storage tube 15, the enclosing step further includes preventing movement of the filter 14 relative to the generally tubular member 15 along the longitudinal axis upon application of axial force of less than 5 Pound-force in a proximal direction.

This assembly process for mounting the blood filter on the spline member 12E and loading it into the storage tube 15 is performed prior to shipment to the user or medical practitioner. In an embodiment, the hub 14D of the filter 14 is positioned on the distal end of the pusher member 12C of the pusher assembly 12. The hub is then inserted into the proximal end of the storage tube 15, and as it is advanced the positioning members 14C displaced radially inward to allow the filter 14 to advance into the storage tube 15. Then the anchor members 14A are displaced radially inward as the filter 14 is further advanced into the storage tube 15. As the filter 14 is advanced, the anchor members 14A are positioned one to a groove in the spline portion 12E1 of the spline member 12E, with the hooks 14A1-14A6 fitting into the gap 12E3 in a spiral fashion as illustrated in FIG. 7B. Finally, the filter 14 and pusher assembly 12 are advanced into the storage tube 15 so that the entire spline member 12E is encompassed within the storage tube 15 as illustrated in FIG. 6C. The assembly may further be facilitated by using a jig or other assembly tool to guide the filter members into proper position for loading into the storage tube 15.

To complete assembly, the storage tube 15 can be sealed on both ends to prevent contamination from entering, and the entire assembly of the pusher assembly 12, filter 14 and storage tube 15 sealed in sterile packaging. To avoid kinking of the pusher assembly 12 or lateral forces on the storage tube 15, the entire assembly can be packed in a linear manner within a foam form and hard outer package, such as cardboard or plastic. In a preferred embodiment, the entire assembly is packaged as two separate sterilized units with the introducer and dilator as one sterilized unit and the filter/pusher assembly in a separate sterilized unit.

Figure 6D:
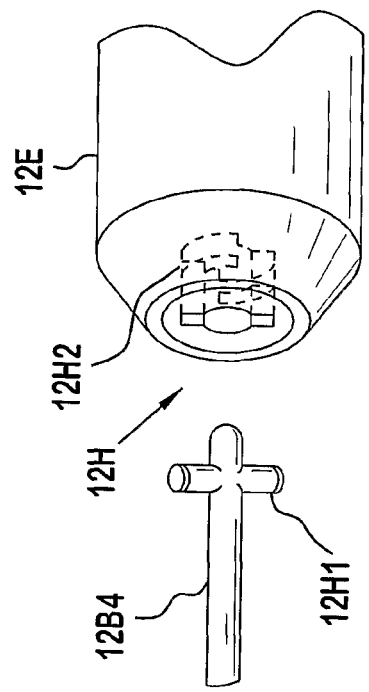
FIGS. 6D, 6E and 6F illustrate embodiments for coupling the spline member illustrated in FIGS. 6B and 6C to the push wire assembly illustrated in FIG. 6A.
Figure 6F:
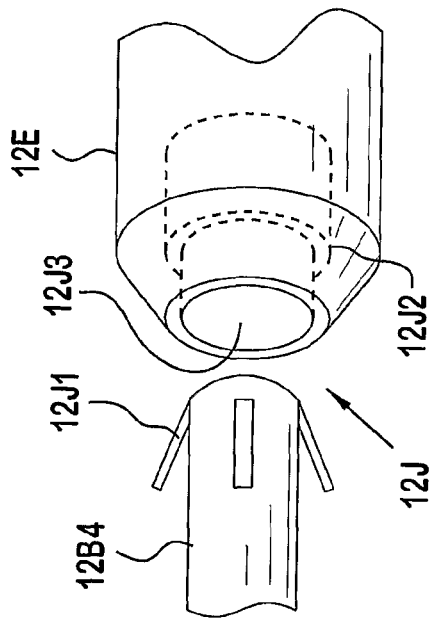
Figure 6E:
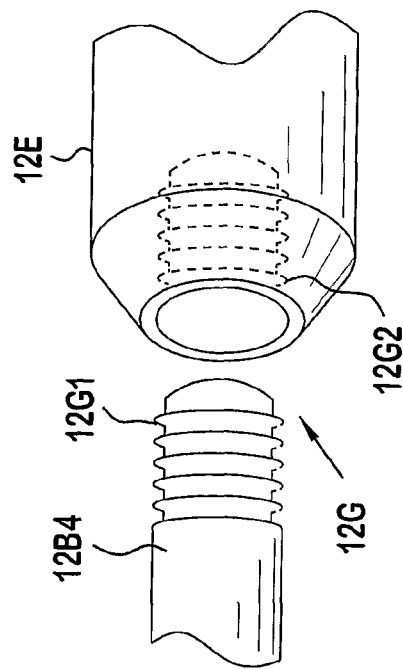

In an alternative embodiment of the pusher assembly, 12, the distal end from the spline member 12E through the pusher member 12C is configured as one piece, and the proximal portions of the pusher assembly, from handle 12A through wire 12B4, configured is one or more pieces, with a coupling mechanism provided for connecting the spline member 12E to the distal end of the push wire 12B4. This embodiment is illustrated in FIGS. 6D, 6E and 6F. As illustrated in these figures, a variety of connection couplings can be used to connect the pusher wire 12B4 to the spline member 12E. By way of example, connector embodiments may include a bayonet connector as illustrated in FIG. 6D, which features a bayonet coupler 16H including tangs 16H1 connected to the push wire 12B4 which engages a bayonet coupling 12H2 within the spline member 12E. Another example; a threaded connection 12G as illustrated in FIG. 6E, which may included a threaded tip 12G1 on the end of the push wire 12B4 which threads into a complementary threaded hole 12G2 in the spline member 12E. A further example is a spring and latch assembly 12J illustrated in FIG. 6 F, that can include spring latches 12J1 mounted on the distal end of the push wire 12B4 which expand into a latching recess 12J2 within the 12E when the distal end of the push wire 12B4 is pushed into the latch opening 12J3. These embodiments permit the filter-spline member/pusher member assembly to placed inside the storage tube 15, such as per the procedure described above, and sealed and stored (such as with caps on each end of the storage tube 15) separate from the long pusher assembly 12A-12B4. Disconnected from the push wire, the filter-spline member-pusher member assembly is less likely to be subjected to lateral forces during shipping, storage and handling. Further, damage to either the push wire 12 or the storage tube 15 does not require the other component to be disposed of. Further, the push wire 12 can be stored in a coiled fashion and uncoiled before assembling to the filter.

In operation for implanting a blood filter into a host, a suitable femoral venous vessel site in the host may be selected. Typically, this is the femoral vein on either the left or right side, depending upon the patient's size or anatomy, the clinician's preference and/or the location of a venous thrombosis. The site can be nicked with a blade and the vein punctured with a suitable entry needle, such as an 18 gage needle, or trocar. A Suitable guidewire, such as a J-tipped guidewire, is inserted into the needle and advanced into a distal vena cava or iliac vessel where a filter is to be delivered. Once the guidewire is in position, the entry needle is removed from the patient and slipped off the proximal end of the guide wire. Then the proximal end of the guidewire is inserted into the introducer distal tip 16A1. Saline or a suitable bio-compatible fluid is provided to the introducer valve 16D to remove air in the introducer 16, and then introducer tip 16A1 is inserted into the patient and advanced along the guidewire until it reaches the desired position in the vena cava or iliac vessel. Positioning of the introducer tip 16A1 within the vein at the site for delivering the filter may be confirmed by fluoroscopy, aided by the radio-opaque markers on or within the introducer 16. The dilator tube 18B is then inserted through the introducer body 16C until the dilator hub 18A is snap-fitted onto the coupling port 16B of the introducer 16. Contrasting agent or dye can also be provided to the ports 18D of the dilator tube 18B via the dilator body 18A to provide for visual imaging of the introducer tip 16A1 via suitable fluoroscopic imaging equipment. The guidewire and the dilator 18 can be removed once the user or physician has determined that the introducer tip 16A1 is at the desired location in the vein or vessel.

Saline infusion can be supplied to the Touhy-Borst Adapter 10. The filter 14, which is pre-stored in the storage tube 15, can be coupled to the coupling port 16B via the snap-fitting, and saline can be permitted to flow through the storage tube 15 to provide lubricity between various components of the delivery system 100. The saline may be chilled during portions of the procedure. Similarly, the saline may be warmed during portions of the procedure, such as just prior to releasing the filter into the vein, to help raise the filter and pusher assembly 12 components above the martensitic-to-austenitic transition temperature, causing the filter to seek its annealed shape. The introducer 16, storage tube 15 and elongated pusher assembly 12 are preferably held in a linear configuration to avoid kinking and minimize friction. The filter 14 is physically advanced from the storage tube 15 through the introducer 16 to a position near the distal tip 16A1 of the introducer 16. The advancement of the filter 14 can be accomplished by maintaining the introducer 16 stationary while pushing on the handle 12A of the elongated pusher assembly 12 in the distal direction. The filter 14 is maintained inside the introducer 16, i.e., undeployed at this point. Markings on the pusher assembly 12 may permit the clinician to know the position of the filter 14 with respect to the end of the introducer 16. Additionally, fluoroscopy may be used to track the position of the filter 14 within the introducer 16 and with respect to the patient. When the filter hub 14D approaches the distal end of the introducer 16, the filter is ready-to be deployed.

Figure 8:
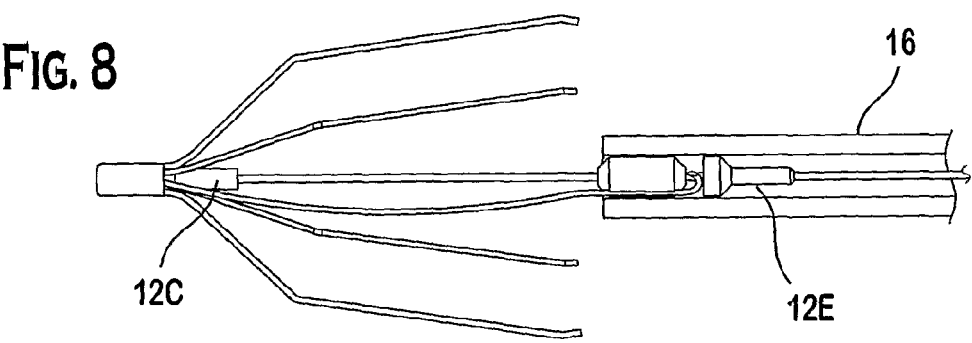
FIG. 8 illustrates the deployment of various locators of a filter as the filter would be deployed in a vessel of a mammalian body.

To deploy the filter 14, the elongated pusher assembly 12 is held stationary while the introducer sheath 16A is pulled back in the proximal direction. This causes the filter to remain in position within the vein, held in place by the pusher member 12C, while the introducer sheath 16A pulls back to release the locator members 14C. Since the locator members 14C are shorter than the anchoring members 14B, the locator members are released first, allowing them to spring out until they contact the walls of the vein. This action places lateral forces on the vein which causes immediate centering of the filter 14 within the vein. A simulation of the deployment of the filter 14 is shown in FIG. 8.

As the introducer 16 is further retracted proximally, the anchor members 14B1-14B6 become unconstrained by the introducer sheath 16A and are free to expand radially. Due to the preload in the push wire portion 12B6 which applies a force through the pusher pad 12C upon the hub of the filter, the filter is released out of the introducer sheath as soon as the hook portions 14A are released from the spline member 12E. Hooks 14A at the ends of the anchor members' 14B1-14B6 begin to dig or penetrate into the blood vessel wall to maintain the filter 14 at approximately the desired location.

Additional information on deployment of this type of filter referenced in the Information for Use is shown and described in U.S. patent application Ser. No. 09/640,865, filed on Aug. 18, 2000, pending, U.S. Pat. Nos. 6,258,026; and 6,007,558. Each of the previously mentioned application and patents is incorporated by reference herein in its entirety into this application.

In another embodiment, bio-active agents can be incorporated with the blood filter or filter delivery system, such as by way of a coating on parts of the filter delivery components (e.g., the pusher pad 12C or the tip of the introducer sheath 16A), or dissolvable structures on, within or attached to the filter delivery components. Alternatively, bio-active agents can be delivered to the region of the filter at the time of the filter emplacement by means of the introducer, either before or after delivery of the filter. Bio-active agent can be included as part of the filter delivery system in order to treat or prevent other conditions (such as infection or inflammation) associated with the filter, or to treat other conditions unrelated to the filter itself. More specifically, bio-active agents may include, but are not limited to: pharmaceutical agents, such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), and trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (e.g., breveldin); anti-inflammatory agents, such as adrenocortical steroids (cortisol, cortisone, fludrocortisones, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents, such as vascular endothelial growth factor (VEGF), fibroblast growth factor (FGF); angiotensin receptor blockers; nitric oxide donors; anti-sense oligionucleotides and combinations thereof; cell cycle inhibitors, such as mTOR inhibitors, and growth factor receptor signal transduction kinase inhibitors; retenoids; cyclin/CDK inhibitors; HMG co-enzyme reductase inhibitors (statins); and protease inhibitors.

While the present invention has been disclosed with reference to certain preferred embodiments, numerous modifications, alterations, and changes to the described embodiments are possible without departing from the sphere and scope of the present invention, which is described, by way of example, in the appended numbered paragraphs below. Accordingly, it is intended that the present invention not be limited to the described embodiments, but that it have the full scope defined by the language of at least the following paragraphs, and equivalents thereof.

What is claimed is:

1. A filter delivery system, comprising:
   a vena cava filter having a plurality of anchor members terminating in a hook, each anchor member having an anchor portion adjacent to the hook, the anchor portion transitioning from a first width equal to a maximum width of the anchor member to a second width less than the first width; and
   a pusher assembly including a spline member having a plurality of grooves, each groove narrowing in width to a minimum width that is less than the anchor portion first width, each groove engaging a section of the anchor portion in an interference fit.

2. The filter delivery system according to claim 1, wherein an end of each hook is positioned outside of the plurality of grooves.

3. The filter delivery system according to claim 2, wherein the spline member includes a first conical surface and a second conical surface.

4. The filter delivery system according to claim 3, wherein the plurality of grooves are defined in the first conical surface and the hook end of each anchor member is positioned over the second conical surface.

5. The filter delivery system according to claim 1, wherein the pusher assembly includes an elongated member, and wherein the spline member is disposed along a distal section of the elongated member.

6. The filter delivery system according to claim 5, wherein the pusher assembly includes a handle at a proximal end of the elongated member and a pusher pad at a distal end of the elongated member, and wherein the spline member is disposed between the handle and the pusher pad.

7. The filter delivery system according to claim 6, wherein the elongated member includes a flexible section connected directly to the pusher pad, the flexible section compressed along the longitudinal axis to provide a spring force for deployment of the vena cava filter.

8. The filter delivery system according to claim 1, wherein each anchor portion of the anchor member has a width less than a maximum width of the anchor member.

9. The filter delivery system according to claim 1, wherein the anchor portion has a frustoconical shape including a first diameter and a second diameter smaller than the first diameter, wherein the first diameter is equivalent to a maximum width of the anchor member, and wherein the anchor portion section engaged by the groove includes the second diameter.

10. The filter delivery system according to claim 1, further comprising an introducer having a coupling port connected to an elongated generally tubular member, a storage member coupled to the coupling port of the introducer and a Y-adaptor, wherein the pusher assembly has a distal end disposed in the storage member and a proximal end extending out of the Y-adapter.

* * * * *